(12) United States Patent
Wischik et al.

(10) Patent No.: US 12,310,973 B2
(45) Date of Patent: *May 27, 2025

(54) ADMINISTRATION AND DOSAGE OF DIAMINOPHENOTHIAZINES

(71) Applicant: WisTa Laboratories Ltd., Singapore (SG)

(72) Inventors: Claude Michel Wischik, Aberdeen (GB); Björn Olaf Schelter, Aberdeen (GB); Damon Jude Wischik, Cambridge (GB); John Mervyn David Storey, Aberdeen (GB)

(73) Assignee: WisTa Laboratories Ltd., Singapore (SG)

(*) Notice: Subject to any disclaimer, the term of this patent is extended or adjusted under 35 U.S.C. 154(b) by 64 days.

This patent is subject to a terminal disclaimer.

(21) Appl. No.: 18/131,570

(22) Filed: Apr. 6, 2023

(65) Prior Publication Data

US 2023/0346794 A1 Nov. 2, 2023

Related U.S. Application Data

(63) Continuation of application No. 17/961,765, filed on Oct. 7, 2022, now Pat. No. 12,128,051, which is a continuation of application No. 17/349,427, filed on Jun. 16, 2021, now Pat. No. 11,759,469, which is a continuation of application No. 16/320,148, filed as application No. PCT/EP2017/068749 on Jul. 25, 2017, now Pat. No. 11,065,256.

(30) Foreign Application Priority Data

Jul. 25, 2016 (GB) .................................. 1612863
Jun. 29, 2017 (GB) .................................. 1710382

(51) Int. Cl.
| | | |
|---|---|---|
| *A61K 31/5415* | (2006.01) | |
| *A23L 33/105* | (2016.01) | |
| *A23L 33/12* | (2016.01) | |
| *A23L 33/15* | (2016.01) | |
| *A23P 10/28* | (2016.01) | |
| *A23P 10/30* | (2016.01) | |
| *A61K 45/06* | (2006.01) | |
| *A61P 25/28* | (2006.01) | |
| *B65D 75/36* | (2006.01) | |

(52) U.S. Cl.
CPC ........ *A61K 31/5415* (2013.01); *A23L 33/105* (2016.08); *A23L 33/12* (2016.08); *A23L 33/15* (2016.08); *A23P 10/28* (2016.08); *A23P 10/30* (2016.08); *A61K 45/06* (2013.01); *A61P 25/28* (2018.01); *B65D 75/36* (2013.01); *A23V 2002/00* (2013.01); *B65D 2203/02* (2013.01)

(58) Field of Classification Search
CPC ... A61K 31/5415; A23L 33/12; A23L 33/105; A23P 10/28; A23P 25/28

USPC ....................................................... 514/224.8
See application file for complete search history.

(56) References Cited

U.S. PATENT DOCUMENTS

| | | | |
|---|---|---|---|
| 9,283,230 B2 | 3/2016 | Clunas et al. | |
| 10,842,796 B2 | 11/2020 | Wischik et al. | |
| 11,065,256 B2* | 7/2021 | Wischik | .................. A61P 25/14 |
| 11,759,469 B2* | 9/2023 | Wischik | .................. A61P 21/00 |
| | | | 514/224.8 |
| 12,128,051 B2* | 10/2024 | Wischik | ............. A61K 31/5415 |
| 2013/0184268 A1 | 7/2013 | Pahnke | |
| 2019/0192530 A1 | 6/2019 | Wischik et al. | |
| 2020/0016165 A1 | 1/2020 | Wischik et al. | |
| 2021/0236509 A1 | 8/2021 | Schelter et al. | |
| 2022/0008431 A1 | 1/2022 | Wischik et al. | |
| 2023/0031369 A1 | 2/2023 | Riedel et al. | |
| 2023/0115931 A1 | 4/2023 | Schelter et al. | |
| 2023/0165877 A1 | 6/2023 | Wischik et al. | |

FOREIGN PATENT DOCUMENTS

| | | |
|---|---|---|
| WO | WO 96/30766 A1 | 10/1996 |
| WO | WO 02/055720 A2 | 7/2002 |
| WO | WO 2002/059150 A2 | 8/2002 |
| WO | WO 2002/075318 A2 | 9/2002 |
| WO | WO 2003/101458 A1 | 12/2003 |
| WO | WO 2006/032879 A2 | 3/2006 |
| WO | WO 2007/110627 A2 | 10/2007 |
| WO | WO 2007/110629 A1 | 10/2007 |
| WO | WO 2007/110630 A1 | 10/2007 |
| WO | WO 2008/006979 A2 | 1/2008 |
| WO | WO 2008/007074 A2 | 1/2008 |
| WO | WO 2008/155533 A2 | 12/2008 |
| WO | WO 2009/044127 A1 | 4/2009 |
| WO | WO 2009/060191 A2 | 5/2009 |
| WO | WO 2010/078659 A1 | 7/2010 |

(Continued)

OTHER PUBLICATIONS

International Search Report and Written Opinion for Application No. PCT/EP2017/068749, mailed May 10, 2017.
International Preliminary Report on Patentability for Application No. PCT/EP2017/068749, mailed Feb. 7, 2019.
International Search Report and Written Opinion for Application No. PCT/EP2017/071437, mailed Nov. 24, 2017.

(Continued)

*Primary Examiner* — Yevgeny Valenrod
(74) *Attorney, Agent, or Firm* — Wolf, Greenfield & Sacks, P.C.

(57) ABSTRACT

The invention provides novel regimens for treatment of neurodegenerative disorders utilising methylthioninium (MT)-containing compounds. The regimens are based on novel findings in relation to the dosage of MT compounds, and their interaction with symptomatic treatments based on modulation of a acetylcholinesterase levels.

32 Claims, 7 Drawing Sheets

(56) References Cited

FOREIGN PATENT DOCUMENTS

Figure 1:
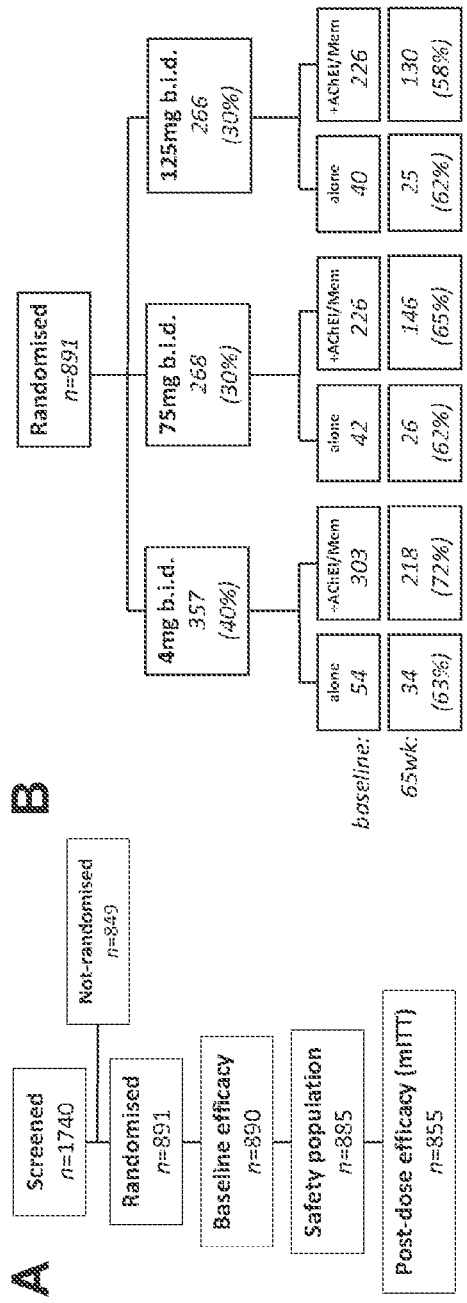

| WO | WO 2010/104394 A1 | 9/2010 |
|---|---|---|
| WO | WO 2011/036558 A2 | 3/2011 |
| WO | WO 2011/036561 A2 | 3/2011 |
| WO | WO 2012/072977 A2 | 6/2012 |
| WO | WO 2012/107706 A1 | 8/2012 |
| WO | WO 2018/019823 A1 | 2/2018 |
| WO | WO 2018/041739 A1 | 3/2018 |
| WO | WO 2020/020751 A1 | 1/2020 |

OTHER PUBLICATIONS

International Preliminary Report on Patentability for Application No. PCT/EP2017/071437, mailed Mar. 14, 2019.
International Search Report and Written Opinion for Application No. PCT/EP2019/069428, mailed Nov. 7, 2019.
International Preliminary Report on Patentability for Application No. PCT/EP2019/069428, mailed Feb. 4, 2021.
International Search Report and Written Opinion for Application No. PCT/EP2020/068422, mailed Sep. 28, 2020.
International Preliminary Report on Patentability for Application No. PCT/EP2020/068422, mailed Jan. 13, 2022.
Alda et al., Methylene blue treatment for residual symptoms of bipolar disorder: randomised crossover study. Br J Psychiatry. Jan. 2017;210(1):54-60. doi: 10.1192/bjp.bp.115.173930. Epub Jun. 9, 2016.
Al-Hilaly et al., Cysteine-Independent Inhibition of Alzheimer's Disease-like Paired Helical Filament Assembly by Leuco-Methylthioninium (LMT). J Mol Biol. Oct. 19, 2018;430(21):4119-4131. doi: 10.1016/j.jmb.2018.08.010. Epub Aug. 16, 2018.
Atamna et al., Mitochondrial pharmacology: electron transport chain bypass as strategies to treat mitochondrial dysfunction. Biofactors. Mar.-Apr. 2012;38(2):158-66. doi: 10.1002/biof.197. Epub Mar. 15, 2012.
Auchter et al., Methylene Blue Preserves Cytochrome Oxidase Activity and Prevents Neurodegeneration and Memory Impairment in Rats With Chronic Cerebral Hypoperfusion.Front Cell Neurosci. May 20, 2020;14:130. doi: 10.3389/fncel.2020.00130. eCollection 2020.
Baddeley et al., Complex disposition of methylthioninium redox forms determines efficacy in tau aggregation inhibitor therapy for Alzheimer's disease. J Pharmacol Exp Ther. Jan. 2015;352(1):110-8. doi: 10.1124/jpet.114.219352. Epub Oct. 15, 2014.
Bruchey et al., Behavioral, Physiological and Biochemical Hormetic Responses to the Autoxidizable Dye Methylene Blue. Am J Pharmacol Toxicol. Jan. 1, 2008;3(1):72-79. doi: 10.3844/ajptsp.2008.72.79.
Congdon et al., Tau-targeting therapies for Alzheimer disease. Nat Rev Neurol. Jul. 2018;14(7):399-415. doi: 10.1038/s41582-018-0013-z.
Douaud et al., Preventing Alzheimer's disease-related gray matter atrophy by B-vitamin treatment. Proc Natl Acad Sci U S A. Jun. 4, 2013;110(23):9523-8. doi: 10.1073/pnas.1301816110. Epub May 20, 2013.
Feldman et al., A phase 3 trial of the tau and TDP-43 aggregation inhibitor, leuco-methylthioninium-bis (hydromethanesulfonate) (LMTM), for behavioural variant frontotemporal dementia (bvFTD). J Neurochemistry. Jul. 18, 2016;138(1):255.
Gauthier et al., Efficacy and safety of tau-aggregation inhibitor therapy in patients with mild or moderate Alzheimer's disease: a randomised, controlled, double-blind, parallel-arm, phase 3 trial. Lancet. Dec. 10, 2016;388(10062):2873-2884. doi: 10.1016/S0140-6736(16)31275-2. Epub Nov. 16, 2016.
Gonzalez-Lima et al., Protection against neurodegeneration with low-dose methylene blue and near-infrared light. Front Cell Neurosci. May 12, 2015;9:179. doi: 10.3389/fncel.2015.00179. eCollection 2015.
Harrington et al., Cellular models of aggregation-dependent template-directed proteolysis to characterize tau aggregation inhibitors for treatment of Alzheimer's disease. J Biol Chem. Apr. 24, 2015;290(17):10862-75. doi: 10.1074/jbc.M114.616029. Epub Mar. 10, 2015.
Jaber et al., Addressing Alzheimer's Disease (AD) Neuropathology Using Anti-microRNA (AM) Strategies. Mol Neurobiol. Dec. 2019;56(12):8101-8108. doi: 10.1007/s12035-019-1632-0. Epub Jun. 10, 2019.
Kazim et al., Neural Regeneration as a Disease-Modifying Therapeutic Strategy for Alzheimer's Disease. Chapter 2 in: Neuroprotection in Alzheimer's Disease. 2017; 3-29. https://doi.org/10.1016/B978-0-12-803690-7.00002-8.
McGleenon et al., Acetylcholinesterase inhibitors in Alzheimer's disease. Br J Clin Pharmacol. 1999;48(4):471-480. doi: 10.1046/j.1365-2125.1999.00026.x.
Mecocci et al., Nutraceuticals in cognitive impairment and Alzheimer's disease. Front Pharmacol. Jun. 23, 2014;5:147. doi: 10.3389/fphar.2014.00147. eCollection 2014.
Melis et al., Different pathways of molecular pathophysiology underlie cognitive and motor tauopathy phenotypes in transgenic models for Alzheimer's disease and frontotemporal lobar degeneration. Cell Mol Life Sci. Jun. 2015;72(11):2199-222. doi: 10.1007/s00018-014-1804-z. Epub Dec. 19, 2014.
Melis et al., Effects of oxidized and reduced forms of methylthioninium in two transgenic mouse tauopathy models. Behav Pharmacol. Jun. 2015;26(4):353-68. doi: 10.1097/FBP.0000000000000133.
Naylor et al., A Controlled Trial of Methylene Blue in Severe Depressive Illness. Biol Psychiatry. May 1987;22(5):657-9. doi: 10.1016/0006-3223(87)90194-6.
Oz et al., Methylene blue and Alzheimer's disease. Biochem Pharmacol. Oct. 15, 2009;78(8):927-32. doi: 10.1016/j.bcp.2009.04.034. Epub May 9, 2009.
Panza et al., A critical appraisal of amyloid- B-targeting therapies for Alzheimer disease. Nat Rev Neurol. Feb. 2019;15(2):73-88. doi: 10.1038/s41582-018-0116-6.
Panza et al., Tau-Centric Targets and Drugs in Clinical Development for the Treatment of Alzheimer's Disease. Biomed Res Int. 2016;2016:3245935. doi: 10.1155/2016/3245935. Epub Jun. 26, 2016.
Pappas, Statistical Analysis Plan (Addendum)—Randomized Double-Blind, Placebo-Controlled, Parallel-Griup, 18-Month Safety and Efficacy Study of Leuco-methylthioninium bis(hydromethanesulfonate) in Subjects with Mild Alzheimer's Disease. Version 1.0. TauRx Therapeutics Ltd. TRx-237-005. Jul. 4, 2016. 4 pages.
Pappas, Statistical Analysis Plan—Randomized Double-Blind, Placebo-Controlled, Parallel-Griup, 18-Month Safety and Efficacy Study of Leuco-methylthioninium bis(hydromethanesulfonate) in Subjects with Mild Alzheimer's Disease. Version 2.0. TauRx Therapeutics Ltd. TRx-237-005. Jun. 20, 2016. 89 pages.
Rodriguez et al., Multimodal Randomized Functional MR Imaging of the Effects of Methylene Blue in the Human Brain. Radiology. Nov. 2016;281(2):516-526. doi: 10.1148/radiol.2016152893. Epub Jun. 28, 2016.
Schelter et al., Concentration-Dependent Activity of Hydromethylthionine on Cognitive Decline and Brain Atrophy in Mild to Moderate Alzheimer's Disease. J Alzheimers Dis. 2019;72(3):931-946. doi: 10.3233/JAD-190772.
Schelter et al., Meta-analysis of two tau aggregation inhibitor Phase 3 trials in mild Alzheimer's disease with low dose hydromethylthionine. JPAD. 2018; 5(1):S66.
Schirmer et al., "Lest we forget you—methylene blue . . .". Neurobiol Aging. Dec. 2011;32(12):2325.e7-16. doi: 10.1016/j.neurobiolaging.2010.12.012. Epub Feb. 12, 2011.
Shiells et al., Concentration-Dependent Activity of Hydromethylthionine on Clinical Decline and Brain Atrophy in a Randomized Controlled Trial in Behavioral Variant Frontotemporal Dementia. J Alzheimers Dis. 2020;75(2):501-519. doi: 10.3233/JAD-191173.
Smith, B vitamins can slow the disease process in early Alzheimer's disease. University of Oxford Impact case study (REF3b). Research Excellence Framework. 2014. 4 pages.
Stack et al., Methylene blue upregulates Nrf2/ARE genes and prevents tau-related neurotoxicity. Hum Mol Genet. Jul. 15, 2014;23(14):3716-32. doi: 10.1093/hmg/ddu080. Epub Feb. 20, 2014.

(56) References Cited

OTHER PUBLICATIONS

Telch et al., Effects of post-session administration of methylene blue on fear extinction and contextual memory in adults with claustrophobia. Am J Psychiatry. Oct. 2014;171(10):1091-8. doi: 10.1176/appi.ajp.2014.13101407.
Tsai et al., Therapy and clinical trials in frontotemporal dementia:past, present, and future. J Neurochem. Aug. 2016;138 Suppl 1:211-21. doi:10.1111/jnc.13640. Epub Jun. 15, 2016.
Tsai et al., Treatment of frontotemporal dementia. Curr Treat Options Neurol. Nov. 2014;16(11):319. doi: 10.1007/s11940-014-0319-0.
Ustyugo et al., New Therapeutic Property of Dimebon as a Neuroprotective Agent. Curr Med Chem. 2018;25(39):5315-5326. doi: 10.2174/0929867323666160804122746.
Wilcock et al., Potential of Low Dose Leuco-Methylthioninium Bis(Hydromethanesulphonate) (LMTM) Monotherapy for Treatment of Mild Alzheimer's Disease: Cohort Analysis as Modified Primary Outcome in a Phase III Clinical Trial. J Alzheimers Dis. 2018;61(1):435-457. doi: 10.3233/JAD-170560.
Wilkinson, Alzheimer'z drug 'halts' decline. BBC News Jul. 29, 2008. Accessed at http://news.bbc.co.uk/go/pr/fr/-/2/hi/health/7525115.stm on Sep. 21, 2017.
Wischik et al., Modeling prion-like processing of tau protein in Alzheimer's disease for pharmaceutical development. J Alzheimers Dis. 2018;62(3):1287-1303. doi: 10.3233/JAD-170727.
Wischik et al., Structural characterization of the core of the paired helical filament of Alzheimer disease. Proc Natl Acad Sci U S A. Jul. 1988;85(13):4884-8. doi: 10.1073/pnas.85.13.4884.
Yamashita et al., Methylene blue and dimebon inhibit aggregation of TDP-43 in cellular models. FEBS Lett. Jul. 21, 2009;583(14):2419-24. doi:10.1016/j.febslet.2009.06.042. Epub Jun. 26, 2009.
Zhao et al., Methylene blue exerts a neuroprotective effect against traumatic brain injury by promoting autophagy and inhibiting microglial activation. Mol Med Rep. Jan. 2016;13(1):13-20. doi: 10.3892/mmr.2015.4551. Epub Nov. 11, 2015.
Albert et al., The diagnosis of mild cognitive impairment due to Alzheimer's disease: recommendations from the National Institute on Aging-Alzheimer's Association workgroups on diagnostic guidelines for Alzheimer's disease. Alzheimers Dement. Author manuscript; available in PMC Mar. 25, 2012. Published in final edited form as: Alzheimers Dement. May 2011; 7(3): 270-279. Published online Apr. 21, 2011. doi: 10.1016/j.jalz.2011.03.008.
Arai et al., Phosphorylated and cleaved TDP-43 in ALS, FTLD and other neurodegenerative disorders and in cellular models of TDP-43 proteinopathy. Neuropathology. Apr. 2010;30(2):170-81. doi: 10.1111/j.1440-1789.2009.01089.x. Epub Jan. 19, 2010.
Benedetti et al., Increasing uncertainty in CNS clinical trials: the role of placebo, nocebo, and Hawthorne effects. Lancet Neurol. Jun. 2016;15(7):736-747. doi: 10.1016/S1474-4422(16)00066-1. Epub Apr. 19, 2016.
Boxer et al., The advantages of frontotemporal degeneration drug development (part 2 of frontotemporal degeneration: the next therapeutic frontier). Alzheimers Dement. Mar. 2013;9(2):189-98. doi: 10.1016/j.jalz.2012.03.003. Epub Oct. 10, 2012.
Callaway et al., Methylene blue improves brain oxidative metabolism and memory retention in rats. Pharmacol Biochem Behav. Jan. 2004;77(1):175-81. doi: 10.1016/j.pbb.2003.10.007.
Callaway et al., Methylene blue restores spatial memory retention impaired by an inhibitor of cytochrome oxidase in rats. Neurosci Lett. Oct. 31, 2002;332(2):83-6. doi: 10.1016/s0304-3940(02)00827-3.
Casey et al., Drugs for Alzheimer's disease: are they effective? P T. Apr. 2010;35(4):208-11.
Cummings et al., The "rights" of precision drug development for Alzheimer's disease. Alzheimers Res Ther. Aug. 31, 2019;11(1):76. doi: 10.1186/s13195-019-0529-5.
Deiana et al., Methylthioninium chloride reverses cognitive deficits induced by scopolamine: comparison with rivastigmine. Psychopharmacology (Berl). Jan. 2009;202(1-3):53-65. doi: 10.1007/s00213-008-1394-2. Epub Nov. 14, 2008.

Desmarais et al., Therapeutic trial design for frontotemporal dementia and related disorders. J Neurol Neurosurg Psychiatry. Apr. 2019;90(4):412-423. doi: 10.1136/jnnp-2018-318603. Epub Oct. 25, 2018.
Disanto et al., Pharmacokinetics of highly ionized drugs. II. Methylene blue—absorption, metabolism, and excretion in man and dog after oral administration. J Pharm Sci. Jul. 1972;61(7):1086-90. doi: 10.1002/jps.2600610710.
Disanto et al., Pharmacokinetics of highly ionized drugs. III. Methylene blue—blood levels in the dog and tissue levels in the rat following intravenous administration. J Pharm Sci. Jul. 1972;61(7):1090-4. doi: 10.1002/jps.2600610711.
Dolder et al., Use of psychostimulants in patients with dementia. Ann Pharmacother. Oct. 2010;44(10):1624-32. doi: 10.1345/aph.1P341. Epub Aug. 24, 2010.
Doody et al., Phase 3 trials of solanezumab for mild-to-moderate Alzheimer's disease. N Engl J Med. Jan. 23, 2014;370(4):311-21. doi: 10.1056/NEJMoa1312889.
Franzen et al., Diversity in Alzheimer's disease drug trials: The importance of eligibility criteria. Alzheimers Dement. Apr. 2022;18(4):810-823. doi: 10.1002/alz.12433. Epub Sep. 30, 2021.
Gonzalez-Lima et al., Extinction memory improvement by the metabolic enhancer methylene blue. Learn Mem. Sep.-Oct. 2004;11(5):633-40. doi: 10.1101/lm.82404.
Huang et al., Alzheimer mechanisms and therapeutic strategies. Cell. Mar. 16, 2012;148(6):1204-22. doi: 10.1016/j.cell.2012.02.040.
Irwin, Tauopathies as clinicopathological entities. Parkinsonism Relat Disord. Jan. 2016;22 Suppl 1(01):S29-33. doi: 10.1016/j.parkreldis.2015.09.020. Epub Sep. 8, 2015.
Jinwal et al., Chemical manipulation of Hsp70 ATPase activity regulates tau stability. J Neurosci. Sep. 30, 2009;29(39):12079-88. doi: 10.1523/JNEUROSCI.3345-09.2009.
Jutten et al., The Cognitive-Functional Composite is sensitive to clinical progression in early dementia: Longitudinal findings from the Catch-Cog study cohort. Alzheimers Dement (N Y). Apr. 17, 2020;6(1):e12020. doi: 10.1002/trc2.12020. eCollection 2020.
Jutten et al., Why a clinical trial is as good as its outcome measure: A framework for the selection and use of cognitive outcome measures for clinical trials of Alzheimer's disease. Alzheimers Dement. Feb. 2023;19(2):708-720. doi: 10.1002/alz.12773. Epub Sep. 10, 2022.
Kertesz, Behavioral and Psychological Symptoms and Frontotemporal Dementia (Pick's Disease). International Psychogeriatrics. 2000; 12(1): 183-187.
Kim et al., Data-driven prognostic features of cognitive trajectories in patients with amnestic mild cognitive impairments. Alzheimers Res Ther. Jan. 22, 2019;11(1):10. doi: 10.1186/s13195-018-0462-z.
Kumar, Potential medicinal plants for CNS disorders: an overview. Phytother Res. Dec. 2006;20(12):1023-35. doi: 10.1002/ptr.1970.
Martinez et al., Methylene blue alters retention of inhibitory avoidance responses. Physiological Psychology. 1978; 6(3): 387-390.
May et al., Reduction and uptake of methylene blue by human erythrocytes. Am J Physiol Cell Physiol. Jun. 2004;286(6):C1390-8. doi: 10.1152/ajpcell.00512.2003. Epub Feb. 18, 2004.
Mohamed et al., Age-related decline in brain and hepatic clearance of amyloid-beta is rectified by the cholinesterase inhibitors donepezil and rivastigmine in rats. ACS Chem Neurosci. Author manuscript; available in PMC: Jan. 20, 2017. Published in final edited form as: ACS Chem Neurosci. Mar. 30, 2015;6(5):725-736. doi: 10.1021/acschemneuro.5b00040.
Moody et al., Methylene blue excretion in depression. Biol Psychiatry. Dec. 1989;26(8):850-2. doi: 10.1016/0006-3223(89)90128-5.
Naylor et al., A two-year double-blind crossover trial of the prophylactic effect of methylene blue in manic-depressive psychosis. Biol Psychiatry. Aug. 1986;21(10):915-20. doi: 10.1016/0006-3223(86)90265-9.
No Author Listed, Clinical Trial ID NCT01689246. Safety and Efficacy Study Evaluating TRx0237 in Subjects with Mild to Moderate Alzheimer's Disease. Submitted: Sep. 20, 2012. Last updated: Mar. 14, 2018. Accessed at: https://clinicaltrials.gov/study/NCT01689246. [last accessed Dec. 20, 2024].

(56) References Cited

OTHER PUBLICATIONS

No Author Listed, EudraCT No. 2012-002866-11. Clinical Trial Results: Randomized, Double-Blind, Placebo-Controlled, Parallel-Group, 15-Month Trial of Leuco-methylthioninium bis(hydromethanesulfonate) in Subjects with Mild to Moderate Alzheimer's Disease. European Union Clinical Trials Registry. Published Feb. 8, 2020. Accessed at: https://www.clinicaltrialsregister.eu/ctr-search/trial/2012-002866-11/results. [last accessed: Dec. 20, 2024].

No Author Listed, TauRx Pharmaceuticals Press Release. Sep. 4, 2016. 3 pages.

Panza et al., Development of disease-modifying drugs for frontotemporal dementia spectrum disorders. Nat Rev Neurol. Apr. 2020;16(4):213-228. doi: 10.1038/s41582-020-0330-x. Epub Mar. 23, 2020.

Peter et al., Pharmacokinetics and organ distribution of intravenous and oral methylene blue. Eur J Clin Pharmacol. Jun. 2000;56(3):247-50. doi: 10.1007/s002280000124.

Pfaffendorf et al., The interaction between methylene blue and the cholinergic system. Br J Pharmacol. Sep. 1997;122(1):95-8. doi: 10.1038/sj.bjp.0701355.

Ramsay et al., Methylene blue and serotonin toxicity: inhibition of monoamine oxidase A (MAO A) confirms a theoretical prediction. Br J Pharmacol. Nov. 2007;152(6):946-51. doi: 10.1038/sj.bjp.0707430. Epub Aug. 27, 2007.

Riha et al., Memory facilitation by methylene blue: Dose-dependent effect on behavior and brain oxygen consumption. Eur J Pharmacol. Mar. 28, 2005;511(2-3):151-8. doi: 10.1016/j.ejphar.2005.02.001.

Salloway et al., Two phase 3 trials of bapineuzumab in mild-to-moderate Alzheimer's disease. New Eng J Med. Jan. 23, 2014;370(4):322-33. doi: 10.1056/NEJMoa1304839.

Schneider et al., Current Alzheimer's disease clinical trials: Methods and placebo outcomes. Alzheimers Dement. Sep. 2009;5(5):388-97. doi: 10.1016/j.jalz.2009.07.038.

Shearman et al., Changes in cerebral neurotransmitters and metabolites induced by acute donepezil and memantine administrations: A microdialysis study. Brain Res Bull. Mar. 31, 2006;69(2):204-13. Doi: 10.1016/j.brainresbull.2005.12.001. Epub Dec. 21, 2005.

Snyder et al., Assessing cognition and function in Alzheimer's disease clinical trials: Do we have the right tools? Alzheimers Dement. Nov. 2014; 10(6):853-60. doi: 10.1016/j.jalz.2014.07.158. Epub Nov. 15, 2014.

Sperling et al., Toward defining the preclinical stages of Alzheimer's disease: recommendations from the National Institute on Aging-Alzheimer's Association workgroups on diagnostic guidelines for Alzheimer's disease. Alzheimers Dement. May 2011; 7(3): 280-292. Published online Apr. 21, 2011. doi: 10.1016/j.jalz.2011.03.003.

Tariot et al., The Alzheimer's Prevention Initiative Autosomal-Dominant Alzheimer's Disease Trial: A study of crenezumab versus placebo in preclinical PSEN1 E280A mutation carriers to evaluate efficacy and safety in the treatment of autosomal-dominant Alzheimer's disease, including a placebo-treated noncarrier cohort. Alzheimers Dement (N Y). Mar. 8, 2018;4:150-160. doi: 10.1016/j.trci.2018.02.002. eCollection 2018.

Ustyugov et al., New therapeutic property of Dimebon as a neuroprotective agent. Curr Med Chem. 2018;25(39):5315-5326. doi: 10.2174/0929867323666160804122746.

Van Bebber et al., Methylene blue fails to inhibit Tau and polyglutamine protein dependent toxicity in zebrafish. Neurobiol Dis. Sep. 2010;39(3):265-71. doi: 10.1016/j.nbd.2010.03.023. Epub Apr. 8, 2010.

Venneri et al., Cerebral blood flow and cognitive responses to rivastigmine treatment in Alzheimer's disease. NeuroReport. Jan. 21, 2002;13(1):83-7. doi: 10.1097/00001756-200201210-00020.

Vercelletto et al., Memantine in Behavioral Variant Frontotemporal Dementia: Negative Results. J Alzheimers Dis. 2011;23(4):749-59. doi: 10.3233/JAD-2010-101632.

Vos et al., Prevalence and prognosis of Alzheimer's disease at the mild cognitive impairment stage. Brain. May 2015;138(Pt 5): 1327-38. doi: 10.1093/brain/awv029. Epub Feb. 17, 2015.

Weintraub et al., Measuring cognition and function in the preclinical stage of Alzheimer's disease. Alzheimers Dement (N Y). Feb. 13, 2018;4:64-75. doi: 10.1016/j.trci.2018.01.003. eCollection 2018.

Wilcock et al., Potential of low dose leuco-methylthioninium bis(hydromethanesulphonate) (LMTM) monotherapy for treatment of mild Alzheimer's disease: cohort analysis as modified primary outcome in a phase 3 clinical trial. J Alzheimers Dis. 2018;61(1):435-457. doi: 10.3233/JAD-170560.

Wischik et al. Isolation of a fragment of tau derived from the core of the paired helical filament of Alzheimer's disease. Proc Natl Acad Sci USA. Jun. 1988;85(12):4506-10. doi: 10.1073/pnas.85.12.4506.

Wischik et al., Quantitative analysis of tau protein in paired helical filament preparations: implications for the role of tau protein phosphorylation in PHF assembly in Alzheimer's disease. Neurobiol Aging. May-Jun. 1995;16(3):409-17; discussion 418-31. doi: 10.1016/0197-4580(95)97327-d.

Wischik et al., Rationale for tau aggregation inhibitor therapy in Alzheimer's disease and other tauopathies. Chapter 11 in: Emerging drugs and targets for Alzheimer's disease: vol. 1: Beta-amyloid, tau protein and glucose metabolism. Cambridge: Royal Society of Chemistry, eds. 2010: 210-32. https://doi.org/10.1039/9781849731065-00210.

Wischik et al., Selective inhibition of Alzheimer disease-like tau aggregation by phenothiazines. Proc Natl Acad Sci U S A. Oct. 1, 1996;93(20):11213-8. doi: 10.1073/pnas.93.20.11213.

Wischik et al., Tau aggregation inhibitor therapy: an exploratory phase 2 study in mild or moderate Alzheimer's disease. J Alzheimers Dis. 2015;44(2):705-20. doi: 10.3233/JAD-142874.

Wischik et al., Tau-aggregation inhibitor therapy for Alzheimer's disease. Biochem Pharmacol. Apr. 15, 2014;88(4):529-39. doi: 10.1016/j.bcp.2013.12.008. Epub Dec. 19, 2013.

Wrubel et al., Methylene blue facilitates the extinction of fear in an animal model of susceptibility to learned helplessness. Neurobiol. Neurobiol Learn Mem. Feb. 2007;87(2):209-17. doi: 10.1016/j.nlm.2006.08.009. Epub Oct. 2, 2006.

Zoellner et al., Enhancing extinction learning in posttraumatic stress disorder with brief daily imaginal exposure and methylene blue: a randomized controlled trial. J Clin Psychiatry. Jul. 2017;78(7):e782-e789. doi: 10.4088/JCP.16m10936.

* cited by examiner

ADMINISTRATION AND DOSAGE OF DIAMINOPHENOTHIAZINES

CROSS-REFERENCE TO RELATED APPLICATIONS

This application is a Continuation application of U.S. application Ser. No. 17/961,765, filed Oct. 7, 2022, which is a Continuation application of U.S. application Ser. No. 17/349,427, filed Jun. 16, 2021, which is a Continuation application of U.S. application Ser. No. 16/320,148, filed Jan. 24, 2019 and issued as U.S. Pat. No. 11,065,256, which is a National Stage filing under 35 U.S.C. 371 of International Patent Application Serial No. PCT/EP2017/068749, filed Jul. 25, 2017, which claims priority to Great Britain Application No. 1612863.9, filed Jul. 25, 2016, and Great Britain Application No. 1710382.1, filed Jun. 29, 2017. The contents of these applications are incorporated herein by reference in their entirety.

TECHNICAL FIELD

The present invention relates generally to methods and materials for use in the treatment or prophylaxis of diseases of protein aggregation, for example cognitive disorders, using diaminophenothiazines.

Background Art

Aberrant protein aggregation is believed to be a proximal cause of numerous disease states, which may be manifested as neurodegeneration, clinical dementia, and other pathological symptoms.

In general, the aberrant protein aggregation is that which arises from an induced conformational polymerisation interaction, i.e., one in which a conformational change of the protein, or in a fragment thereof, gives rise to templated binding and aggregation of further (precursor) protein molecules in a self-propagating manner.

Once nucleation is initiated, an aggregation cascade may ensue which involves the induced conformational polymerisation of further protein molecules, leading to the formation of toxic product fragments in aggregates which are substantially resistant to further proteolysis.

For example certain conditions of dementia may be characterised by a progressive accumulation of intracellular and/or extracellular deposits of proteinaceous structures such as β-amyloid plaques and neurofibrillary tangles (NFTs) in the brains of affected patients. The appearance of these lesions largely correlates with pathological neurofibrillary degeneration and brain atrophy, as well as with cognitive impairment (see, e.g., Mukaetova-Ladinska, E. B. et al., 2000, Am. J. Pathol., Vol. 157, No. 2, pp. 623-636).

Current approved treatments for Alzheimer's disease include acetylcholinesterase inhibitors (AChEIs) and the N-methyl-D-aspartate receptor antagonist memantine. These are symptomatic and do not address the underlying disease pathology. Therapies targeting the amyloid pathology have so far proved unsuccessful in late stage clinical trials (Geerts et al., 2013; Mullane and Williams, 2013). According to a recent Lancet Neurology Commission. "an effective treatment for AD is perhaps the greatest unmet medical need facing modern medicine", (Winblad et al., 2016) not least because the global economic cost of dementia is estimated to be $818 billion, or 0.65% of global gross domestic product (Alzheimer's Disease International, 2015).

NFTs (the pathology discovered by Alois Alzheimer, (Alzheimer, 1907)) are made up of paired helical filaments (PHFs), composed predominantly of a 12-kDa repeat-domain fragment of the microtubule-associated protein tau (Wischik et al., 1985; Wischik et al., 1988a,b). Numerous studies have confirmed a quantitative link for the spread of neurofibrillary tangle pathology and the quantity of aggregated tau with both the extent of clinical dementia and functional molecular imaging deficits in Alzheimer's disease (Arriagada et al., 1992; Brier et al., 2016; Giannakopoulos et al., 2003; Josephs et al., 2003; Maruyama et al., 2013). Since pathological aggregation of tau protein begins at least 20 years prior to any of the clinical manifestations, (Braak and del Tredici, 2013) targeting this pathology offers a rational approach to both treatment and prevention of AD and related tau aggregation disorders (Huang and Mucke, 2012; Wischik et al., 2014; Wischik et al., 2010).

The tau fragment originally identified as an intrinsic structural constituent of the PHF core has prion-like properties in vitro in that it captures normal tau protein with very high affinity (Lai et al., 2016) and converts it to a proteolytically stable replicate of itself (Wischik et al., 1996; Harrington et al., 2015) in a process which is self-propagating and autocatalytic. Phosphorylation is inhibitory to aggregation (Lai et al., 2016) and is unlikely to drive of the cascade (Mukaetova-Ladinska et al., 2000; Schneider et al., 1999; Wischik et al., 1995). Direct inhibition of tau aggregation represents a plausible point for therapeutic intervention.

Methylthioninium (MT) acts as a tau aggregation inhibitor (TAI) in vitro, (Wischik et al., 1996; Harrington et al., 2015) dissolves PHFs from Alzheimer's disease brain tissue, (Wischik et al., 1996) and reduces tau pathology and associated behavioural deficits in transgenic mouse tau models at brain concentrations consistent with human oral dosing. (Melis et al., 2015; Baddeley et al., 2015) MT has also been shown to inhibit other disease-associated protein aggregation (see e.g. WO2007/110629).

MT is a redox molecule and, depending on environmental conditions (e.g., pH, oxygen, reducing agents), exists in equilibrium between a reduced [leucomethylthioninium (LMT)] and oxidized form (MT$^+$).

WO96/30766 describes such MT containing compounds for use in the treatment and prophylaxis of various diseases, including AD and Lewy Body Disease. One example compound was methylthioninium chloride ("MTC") commonly known as methylene blue, which is the chloride salt of the oxidized form of methylthioninium (MT) i.e. MT$^+$.

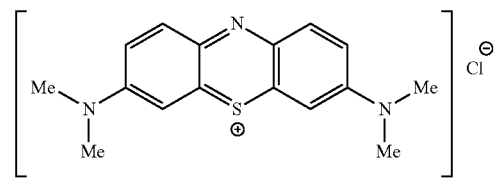

methyl-thioninium chloride
MTC

WO96/30766 describes, in the case of oral administration, a daily dosage of about 50 mg to about 700 mg, preferably about 150 mg to about 300 mg, divided in preferably 1-3 unit doses.

WO2007/110630 discloses certain specific diaminophenothiazine compounds related to MTC, including (so-called)

ETC, DEMTC, DMETC, DEETC, MTZ, ETZ, MTI, MTILHI, ETI, ETLHI, MTN, and ETN, which are useful as drugs, for example in the treatment of Alzheimer's disease.

WO2007/110630 describes dosage units comprising 20 to 300 mg of 3,7-diaminophenothiazine (DAPTZ) compounds described therein e.g. 30 to 200 mg, for example 30 mg, 60 mg, 100 mg, 150 mg, 200 mg. A suitable dose of the DAPTZ compound is suggested in the range of about 100 ng to about 25 mg (more typically about 1 μg to about 10 mg) per kilogram body weight of the subject per day e.g. 100 mg, 3 times daily, 150 mg, 2 times daily, 200 mg, 2 times daily. A dosage of 50 mg 3 or 4 times daily is also discussed.

A preliminary pharmacokinetic model for methylene blue, based on studies of urinary excretion data sets in humans, dogs and rats, was proposed by DiSanto and Wagner, J Pharm Sci 1972, 61:1086-1090 and 1972, 61:1090-1094 and Moody et al., Biol Psych 1989, 26: 847-858.

Peter et al. (2000) Eur J Clin Pharmacol 56: 247-250 provided a model which integrated blood level data, which contradicted the earlier data from DiSanto and Wagner as regards terminal elimination half-life.

May et al. (Am J Physiol Cell Physiol, 2004, Vol. 286. pp. C1390-C1398) showed that human erythrocytes sequentially reduce and take up MTC i.e. that MTC itself is not taken up by the cells but rather that it is the reduced from of MT that crosses the cell membrane. They also showed that the rate of uptake is enzyme dependent; and that both oxidised and reduced MT are concentrated in cells (reduced MT re-equilibrates once inside the cell to form oxidised MT).

Based on these and other disclosures, it is believed that orally administered MTC and similar drugs are taken up in the gut and enter the bloodstream, with unabsorbed drug percolates down the alimentary canal, to the distal gut. One important undesired side-effect is the effect of the unabsorbed drug in the distal gut, for example, sensitisation of the distal gut and/or antimicrobial effects of the unabsorbed drug on flora in the distal gut, both leading to diarrhoea.

MTC was tested clinically in a phase 2 study (Wischik et al., 2015). Although the minimum safe and effective dose was identified as 138 mg/day, a higher dose of 218 mg/day had limited efficacy due to absorption limitations, most likely due to the need for the $MT^+$ to be reduced to the leuco-MT (LMT) form to permit efficient absorption by passive diffusion.

WO2009/044127 disclosed the results of a phase 2 clinical trial, which indicated that MTC had two systemic pharmacological actions: cognitive effects and haematological effects, but that these actions were separable. Specifically the cognitive effects did not show a monotonic dose-response relationship, whereas the haematological effects did. It was proposed that two distinct species were responsible for the two types of pharmacological activity: MTC absorbed as the uncharged Leuco-MT form being responsible for the beneficial cognitive activity, and MTC absorbed as an oxidised dimeric species being responsible for the oxidation of haemoglobin. WO2009/044127 described how dosage forms could be used to maximise the bioavailability of the therapeutically active (cognitively effective) species whether dosing with oxidised or leuco-DAPTZ compounds.

Since it is the reduced form of MT that is taken up by cells, it has been proposed to administer a reduced form to patients. This may also reduce reliance on the rate limiting step of enzymatic reduction.

MTC, a phenothiazin-5-ium salt, may be considered to be an "oxidized form" in relation to the corresponding 10H-phenothiazine compound, N,N,N',N'-tetramethyl-10H-phenothiazine-3,7-diamine, which may be considered to be a "reduced form":

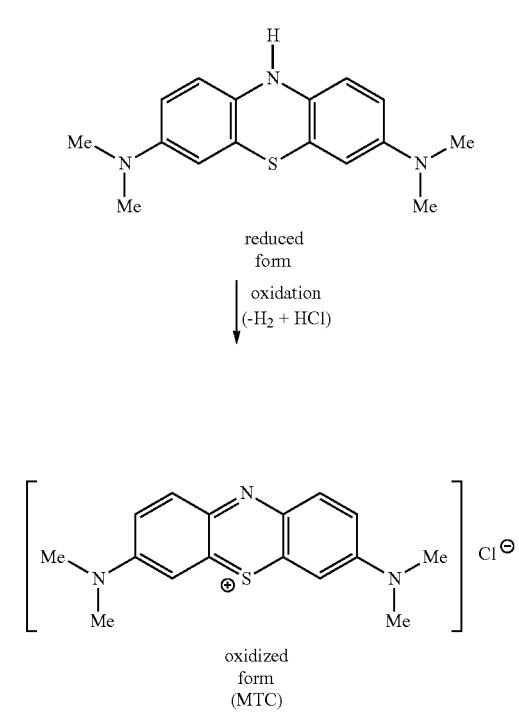

reduced form oxidation
(-H₂ + HCl)

oxidized form
(MTC)

The "reduced form" (or "leuco form") is known to be unstable and can be readily and rapidly oxidized to give the corresponding "oxidized" form.

WO 02/055720 discloses the use of reduced forms of certain diaminophenothiazines for the treatment of protein aggregating diseases, primarily tauopathies. Based on in vitro activity for the reduced forms of diaminophenothiazines therein, a suggested daily dosage was 3.2-3.5 mg/kg, and dosages of 20 mg t.d.s., 50 mg t.d.s. or 100 mg t.d.s., combined with 2× mg ratio of ascorbic acid in such a manner as to achieve more than 90% reduction prior to ingestion were also described.

WO2007/110627 disclosed certain 3,7-diamino-10H-phenothiazinium salts, effective as drugs or pro-drugs for the treatment of diseases including Alzheimer's disease. These compounds are also in the "reduced" or "leuco" form when considered in respect of MTC. These leucomethylthioninium compounds were referred to as "LMTX" salts, and included the following salts:

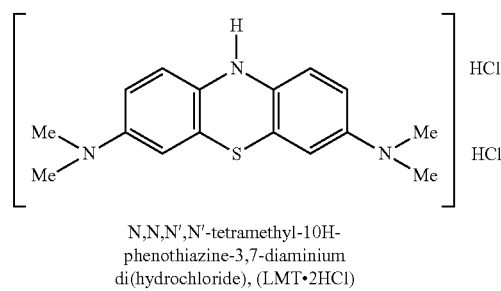

N,N,N',N'-tetramethyl-10H-
phenothiazine-3,7-diaminium
di(hydrochloride), (LMT·2HCl)

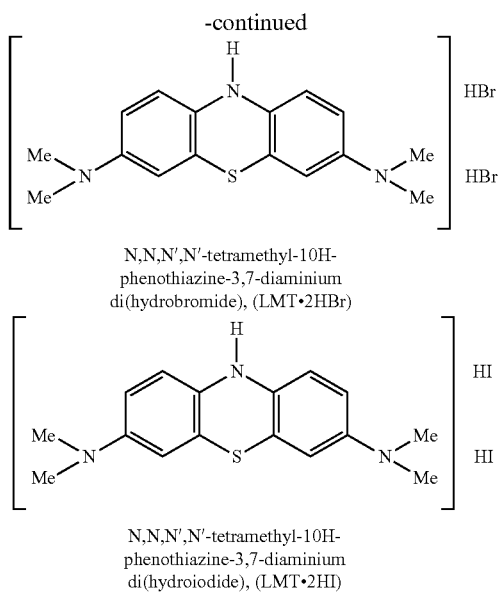

N,N,N',N'-tetramethyl-10H-
phenothiazine-3,7-diaminium
di(hydrobromide), (LMT·2HBr)

N,N,N',N'-tetramethyl-10H-
phenothiazine-3,7-diaminium
di(hydroiodide), (LMT·2HI)

WO2012/107706 described other LMTX salts having superior properties to the LMTX salts listed above, including leuco-methythioninium bis(hydromethanesulfonate) (LMTM):

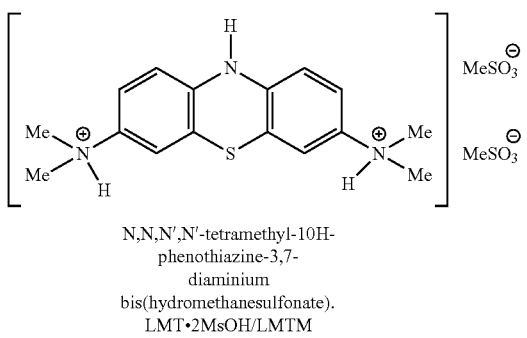

N,N,N',N'-tetramethyl-10H-
phenothiazine-3,7-
diaminium
bis(hydromethanesulfonate).
LMT·2MsOH/LMTM Specifically LMTM retains TAI activity in vitro and in vivo (Wischik et al, 1996; Harrington et al., 2015; Melis et al., 2015) has superior pharmaceutic properties in terms of solubility and pKa, and is not subject to the absorption limitations of the MT$^+$ form.[24] (Baddeley et al., 2015)

WO2007/110627 and WO2012/107706 describes dosage units comprising 20 to 300 mg of the DAPTZ compounds described therein e.g. 30 to 200 mg, for example 30 mg, 60 mg, 100 mg, 150 mg, 200 mg. A suitable dose of the DAPTZ compound is suggested in the range of about 100 ng to about 25 mg (more typically about 1 μg to about 10 mg) per kilogram body weight of the subject per day e.g. 100 mg, 3 times daily, 150 mg, 2 times daily, 200 mg, 2 times daily.

DISCLOSURE OF THE INVENTION

The present inventors have conducted a 15-month double-blind randomised controlled phase 3 trial in mild to moderate AD patient to test the safety and efficacy of LMTM.

Doses of LMTM at 75 mg and 125 mg given twice daily (b.i.d.) were compared with a control dose of 4 mg b.i.d. The control dosage was determined from prior repeat-dose phase 1 studies as the minimum needed to maintain blinding with respect to discolouration of excreta.

Unexpectedly, the 4 mg b.i.d. dose showed therapeutic benefits. The efficacy profiles were similar in mild and moderate subjects for most of the measured outcomes.

The reason for the efficacy of this low dose of MT compound, is unclear. It has previously been shown that the absorption and distribution of MT to the brain is complex, and likely to be mediated via red cells rather than plasma (Baddeley et al., 2015) providing a route which protects MT from first-pass metabolism. In the same study MT uptake into red cells was approximately 20-fold higher in vivo when as administered intravenously as LMTM compared with MTC, most likely due to direct red cell uptake of LMT by passive diffusion without need for prior reduction of MT$^+$ as is the case for MTC (Baddeley et al., 2015; May et al., 2004). Without wishing to be bound by theory, the results of the present study suggest that MT uptake and distribution are capacity-limited by the amount that red cells can take up whilst within the portal circulation.

Unlike an earlier phase 2 study, which was conducted in subjects not taking AD-labelled co-medications, patients in the phase 3 trial were permitted to enter whether or not they were not taking these medications, as it was considered infeasible for them to be restricted given their extensive use.

Unexpectedly, treatment benefit in AD (according to the trial criteria) was restricted to patients taking LMTM as monotherapy. By contrast, the decline seen at corresponding doses in patients taking LMTM in combination with AD-labelled treatments (acetylcholinesterase inhibitors [AChEIs] and\or memantine) who were the majority, was indistinguishable on all parameters from that seen in the control arm.

The reason for the loss of benefit on clinical and volumetric outcomes in AD when LMTM is combined with symptomatic AD treatments is unclear, although a possible contributory factor may be induction of the multidrug resistance protein 1 (MDR1), a transporter which is upregulated by AChEIs and memantine. This transporter may directly or indirectly lead to reduction of the levels of MT from the site of action.

Irrespective of the mechanism, the disclosure herein indicates that much lower doses of MT than previously envisaged can produce substantial clinical benefits whilst being well tolerated and having fewer side effects than the higher doses.

In respect of AD treatments, such treatments would preferably be a monotherapy, or at least introduced either prior to or following cessation of the currently available AD treatments AChEIs and memantine, Although the term "low dose" or "low dosage" has been used in relation to MT-containing compounds in prior art publications, there is no teaching or suggestion in those publications of the utility of the present invention.

For example:

Telch, Michael J., et al. "Effects of post-session administration of methylene blue on fear extinction and contextual memory in adults with claustrophobia." American Journal of Psychiatry 171.10 (2014): 1091-1098: this publication refers to the use of "low-dose methylene blue" on retention of fear extinction and contextual memory following fear extinction training. The paper reports that "Methylene blue is a diamino phenothiazine drug that at low doses (0.5-4 mg/kg) has neurometabolic-enhancing properties. The dosages used in the publication were 260 mg/day for adult participants, corresponding to a 4 mg/kg dose.

Gonzalez-Lima F and Auchter A (2015) "Protection against neurodegeneration with low-dose methylene blue and near-infrared light". Front. Cell. Neurosci. 9:179. doi:

10.3389/fncel.2015.00179: this publication discusses the cellular mechanisms mediating the neuroprotective effects of low doses of methylene blue and near-infrared light. It refers to earlier work citing 0.5-4 mg/kg of methylene blue as safe and effective.

Alda, Martin, et al. "Methylene blue treatment for residual symptoms of bipolar disorder: randomised crossover study." *The British Journal of Psychiatry* (2016): doi: 10.1192/bjp.bp115.173930: this publication described the use of a 15 mg "low dose" of methylene blue as a placebo in a 6 month trial. The "active dose" was 195 mg. In each case the dose was split three times daily.

Rodriguez. Pavel, et al. "Multimodal Randomized Functional MR Imaging of the Effects of Methylene Blue in the Human Brain." *Radiology* (2016): 152893: this publication also refers to the 'known' pharmacokinetic and side effects of "low-dose" (0.5-4.0 mg/kg) methylene blue, which are contrasted with the effects of dosages greater than 10 mg/kg. The dosages used in the publication were 280 mg/day for adult participants, approximating to a 4 mg/kg dose.

Naylor et al. (1986) "A two-year double-blind crossover trial of the prophylactic effect of methylene blue in manic-depressive psychosis". Biol. Psychiatry 21:915-920 and Naylor et al. (1987) A controlled trial of methylene blue in severe depressive psychosis. Biol. Psychiatry 22:657-659: these studies used 15 mg/day methylene, nominally as a placebo vs. a treatment of 300 mg/day methylene blue.

A further example dosage is 3 to 10 mg.
A further preferred dosage is 3.5 to 7 mg.
A further preferred dosage is 4 to 6 mg.

As explained below, when administering MT in the reduced (LMT) form, it may be desired to use a smaller total amount within the recited range. compared to the oxidised (MT*) form.

As explained below, when administering the MT dose split in a larger number of doses/day it may be desired to use a smaller total amount within the recited range, compared to a single daily dosing, or a smaller number of doses per day.

In other embodiments the neurodegenerative disorder may be AD.

As explained herein, in some embodiments the treatment will be a monotherapy, or at least will exclude co-medication with AChEIs and memantine, In other embodiments the neurodegenerative disorder may be a neurodegenerative disorder other than AD.

Also provided herein are methods of prophylactic treatment of neurodegenerative disorders of protein aggregation.

Also provided herein are novel dosage forms containing low unit doses of MT compounds, for example high purity MT compounds, for example MT$^+$ compounds or LMTX compounds.

These aspects and embodiments will now be described in more detail:

Methylthioninium Moiety

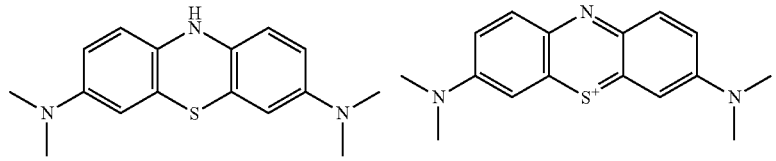

| | | |
|---|---|---|
| Structure | (structure shown) | (structure shown) |
| IUPAC | N3,N3,N7,N7-tetramethyl-10H-phenothiazine-3,7-diamine | N3,N3,N7,N7-tetramethylphenothiazin-5-ium-3,7-diamine |
| Composition | Formula Weight: 285.41(1) | Formula Weight: 284.40(1) |
| | Exact Mass: 285.1299683(1) | Exact Mass: 284.1215947(1) |
| | Formula: $C_{16}H_{19}N_3S$ | Formula: $C_{16}H_{18}N_3S$ |
| | Composition: C 67.33% H 6.71% N 14.72% S 11.23% | Composition: C 67.57% H 6.38% N 14.78% S 11.27% |
| Synonym | leucomethylthioninium (LMT) | oxidized methylthioninium (MT$^+$) |

However in the latter paper the authors proposed that the placebo dosage may act as an antidepressant.

Thus in one aspect there is disclosed a method of treatment of a neurodegenerative disorders of protein aggregation in a subject, which method comprises orally administering to said patient an methylthioninium (MT) containing compound, wherein said administration provides a total of between 0.5 and 20 mg of MT to the subject per day, optionally split into 2 or more doses.

The total dose may be from around any of 0.5, 1, 1.5, 2, 2.5, 3, 3.5, 4 mg to around any of 5, 6, 7, 8, 9, 10, 11, 12, 13, 14, 15, 16, 17, 18, 19, 20 mg.

An example dosage is 1 to 20 mg.
A further example dosage is 2 to 15 mg.

The MT$^+$-containing compounds used in the present invention can contain MT in either reduced or oxidised form. The "MT" is the active ingredient, which is to say that it is present to provide the recited therapeutic effect. Specifically, the compounds may comprise either of the MT moieties described above. The MT moieties per se described above are not stable. They will therefore be administered as MT compounds—for example LMT or MT$^+$ salts.

MT$^+$ salts will generally include one or more anionic counter ions (X$^-$) to achieve electrical neutrality. The compounds may be hydrates, solvates, or mixed salts of the MT$^+$ salt.

LMT containing compounds will generally be stabilised, for example by the presence of one or more protic acids e.g. two protic acids.

The MT content of such salts can be readily calculated by those skilled in the art based on the molecular weight of the compound, and the molecular weight of the MT moiety. Examples of such calculations are given herein.

LMT Compounds

Preferably the MT compound is an LMT compound.

Preferably the MT compound is an "LMTX" compound of the type described in WO2007/110627 or WO2012/107706.

Thus the compound may be selected from compounds of the following formula, or hydrates or solvates thereof:

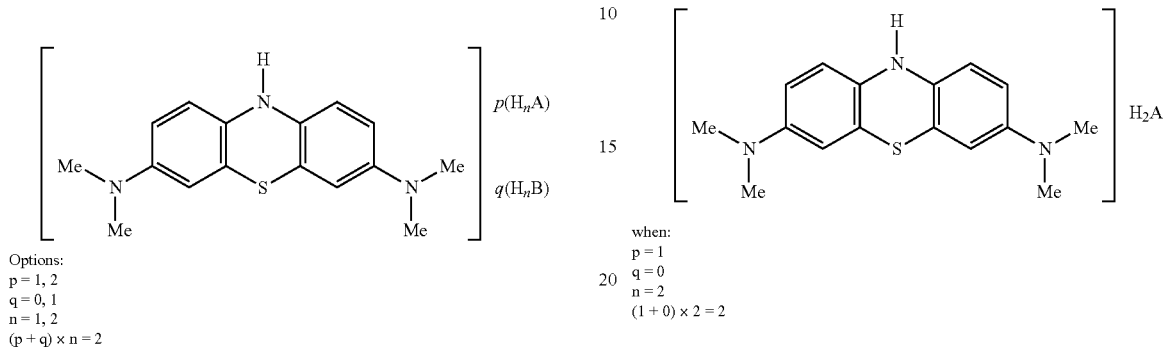

Options:
p = 1, 2
q = 0, 1
n = 1, 2
(p + q) × n = 2

Each of $H_nA$ and $H_nB$ (where present) are protic acids which may be the same or different.

By "protic acid" is meant a proton ($H^+$) donor in aqueous solution. Within the protic acid $A^-$ or $B^-$ is therefore a conjugate base. Protic acids therefore have a pH of less than 7 in water (that is the concentration of hydronium ions is greater than $10^{-7}$ moles per litre).

In one embodiment the salt is a mixed salt that has the following formula, where HA and HB are different monoprotic acids:

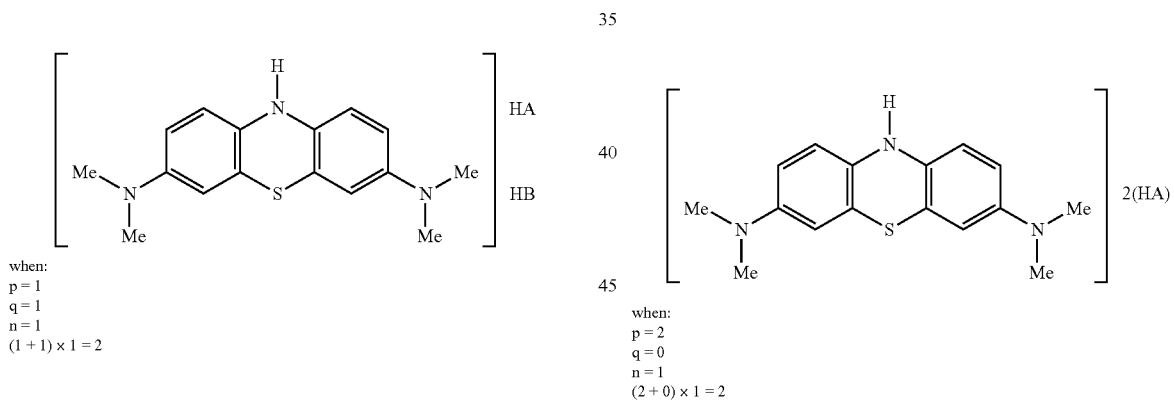

when:
p = 1
q = 1
n = 1
(1 + 1) × 1 = 2

However preferably the salt is not a mixed salt, and has the following formula:

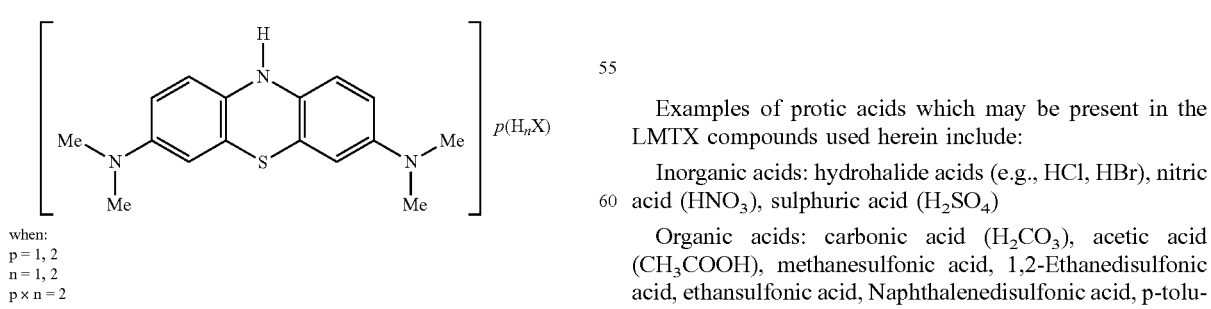

when:
p = 1, 2
n = 1, 2
p × n = 2 wherein each of $H_nX$ is a protic acid, such as a di-protic acid or mono-protic acid.

In one embodiment the salt has the following formula, where $H_2A$ is a di-protic acid:

[structure] $H_2A$ when:
p = 1
q = 0
n = 2
(1 + 0) × 2 = 2

Preferably the salt has the following formula which is a bis monoprotic acid:

[structure] 2(HA)

when:
p = 2
q = 0
n = 1
(2 + 0) × 1 = 2

Examples of protic acids which may be present in the LMTX compounds used herein include:

Inorganic acids: hydrohalide acids (e.g., HCl, HBr), nitric acid ($HNO_3$), sulphuric acid ($H_2SO_4$)

Organic acids: carbonic acid ($H_2CO_3$), acetic acid ($CH_3COOH$), methanesulfonic acid, 1,2-Ethanedisulfonic acid, ethansulfonic acid, Naphthalenedisulfonic acid, p-toluenesulfonic acid, Preferred acids are monoprotic acid, and the salt is a bis(monoprotic acid) salt.

A preferred MT compound is LMTM:

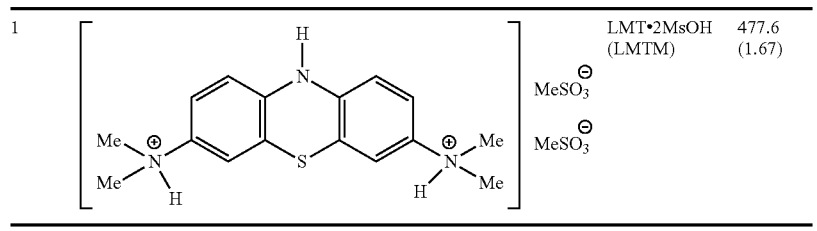

| 1 | | LMT·2MsOH (LMTM) | 477.6 (1.67) |

The anhydrous salt has a molecular weight of around 477.6. Based on a molecular weight of 285.1 for the LMT core, the weight factor for using this MT compound in the invention is 1.67. By "weight factor" is meant the relative weight of the pure MT containing compound vs. the weight of MT which it contains.

Other weight factors can be calculated for example MT compounds herein, and the corresponding dosage ranges can be calculated therefrom.

Therefore the invention embraces a total daily dose of around 0.8 to 33 mg/day of LMTM.

More preferably around 6 to 12 mg/day of LMTM total dose is utilised, which corresponds to about 3.5 to 7 mg MT.

Other example LMTX compounds are as follows. Their molecular weight (anhydrous) and weight factor is also shown:

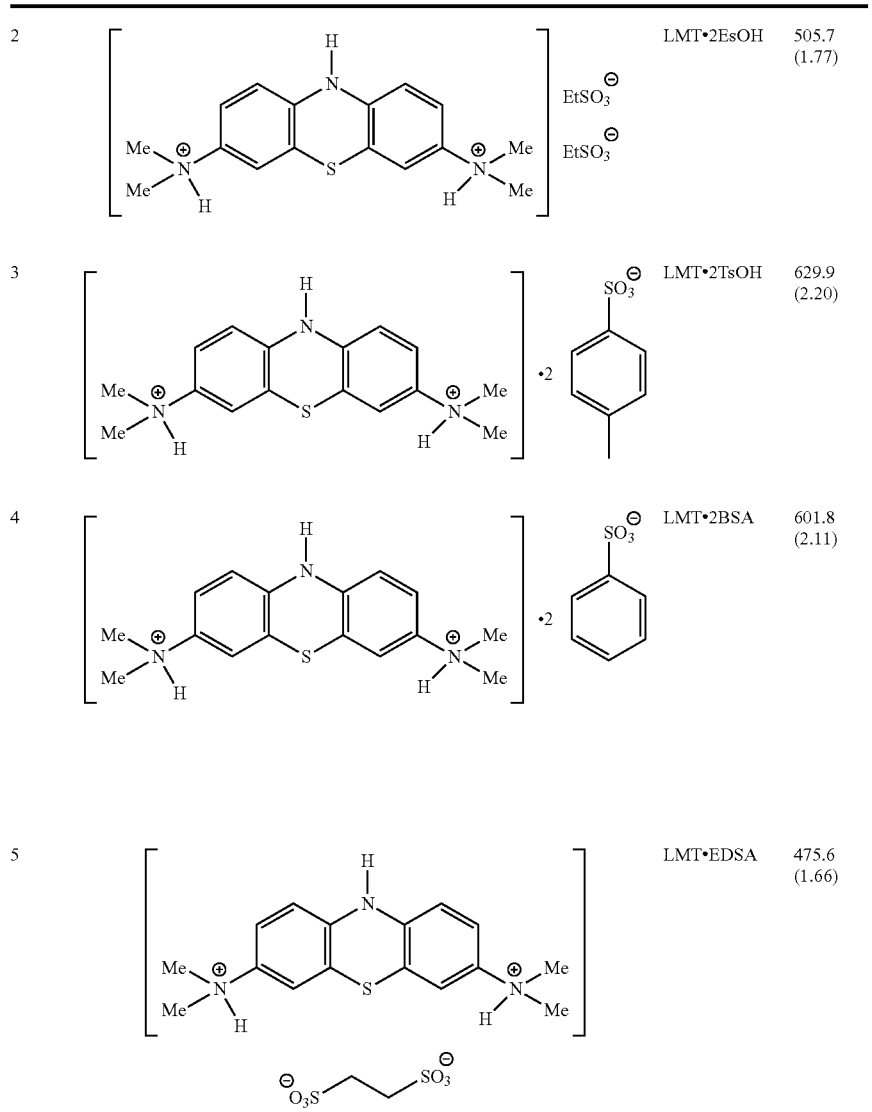

| 2 | LMT·2EsOH | 505.7 (1.77) |
| 3 | LMT·2TsOH | 629.9 (2.20) |
| 4 | LMT·2BSA | 601.8 (2.11) |
| 5 | LMT·EDSA | 475.6 (1.66) |

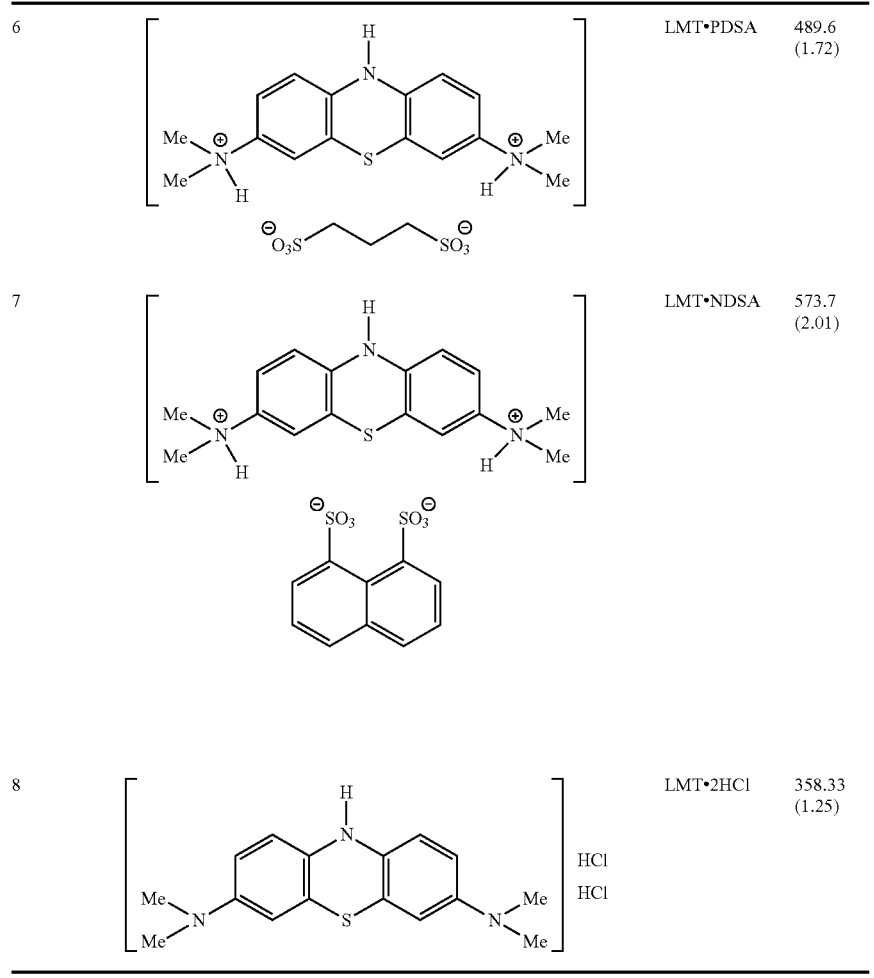

| | | | |
|---|---|---|---|
| 6 | | LMT·PDSA | 489.6 (1.72) |
| 7 | | LMT·NDSA | 573.7 (2.01) |
| 8 | | LMT·2HCl | 358.33 (1.25) |

The dosages described herein with respect to MT thus apply mutatis mutandis for these MT containing compounds, as adjusted for their molecular weight.

Oxidised MT Compounds

In another embodiment the MT compound is an MT$^+$ compound.

Preferably the MT compound is an MT$^+$ compound of the type described in WO96/30766 or WO2007/110630.

Thus the compound may be selected from compounds of the following formula, or hydrates, solvates, or mixed salts thereof:

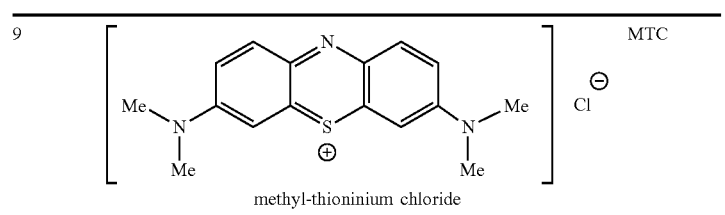

Where X$^-$ is an anionic counter ion.

In some embodiments of the present invention the MT$^+$ compound is MTC, for example a "high purity" MTC as described below.

In some embodiments of the present invention the MT$^+$ compound is not MTC.

9     MTC methyl-thioninium chloride

As explained in WO2011/036561 and WO2011/036558, MTC occurs in a number of polymorphic forms having different levels of hydration.

In some embodiments of the present invention, the MT$^+$ compound is a high purity MTC.

In this context 'high purity' is defined by one or more of the criteria set out below.

In some embodiments, the MTC has a purity of greater than 97%.

In some embodiments, the MTC has a purity of greater than 98%.

In some embodiments, the MTC has a purity of greater than 99%.

In some embodiments, the MTC has less than 2% Azure B as impurity.

In some embodiments, the MTC has less than 1% Azure B as impurity.

In some embodiments, the MTC has less than 0.5% Azure B as impurity.

In some embodiments, the MTC has less than 0.1% Azure B as impurity.

In some embodiments, the MTC has less than 0.15% Azure A as impurity.

In some embodiments, the MTC has less than 0.10% Azure A as impurity.

In some embodiments, the MTC has less than 0.05% Azure A as impurity.

In some embodiments, the MTC has less than 0.15% Azure C as impurity.

In some embodiments, the MTC has less than 0.10% Azure C as impurity.

In some embodiments, the MTC has less than 0.05% Azure C as impurity.

In some embodiments, the MTC has less than 0.13% MVB (Methylene Violet Bernstein) as impurity.

In some embodiments, the MTC has less than 0.05% MVB as impurity.

In some embodiments, the MTC has less than 0.02% MVB as impurity.

All percentage purities recited herein are by weight unless otherwise specified.

In some embodiments, the MTC has an elementals purity that is better than that specified by the European Pharmacopeia (EP).

As used herein, the term 'elementals purity' pertains to the amounts of the twelve (12) metals specified by the European Pharmacopeia: Al, Cd, Cr, Cu, Sn, Fe, Mn, Hg, Mo, Ni, Pb, and Zn. The current edition of the European Pharmacopeia (8$^{th}$ Edition, supplementum 8.8) specifies the following limits for these metals:

| European Pharmacopeia 8.8 (EP8.8) | |
|---|---|
| Element | Maximum content (µg/g) |
| Aluminium (Al) | 100 |
| Cadmium (Cd) | 1 |
| Chromium (Cr) | 100 |
| Copper (Cu) | 300 |
| Tin (Sn) | 10 |
| Iron (Fe) | 200 |
| Manganese (Mn) | 10 |
| Mercury (Hg) | 1 |
| Molybdenum (Mo) | 10 |
| Nickel (Ni) | 10 |
| Lead (Pb) | 10 |
| Zinc (Zn) | 100 |

In one embodiment, the MTC has an elementals purity (e.g. for each of Al, Cd, Cr, Cu, Sn. Fe, Mn, Hg, Mo. Ni, Pb, and Zn) which is equal to or better than (i.e. lower than) the EP8.8 values set out in the table above.

In one embodiment, the MTC has an elementals purity which is equal to or better than 0.9 times the EP8.8 values set out in the table above.

In one embodiment, the MTC has an elementals purity which is equal to or better than 0.8 times the EP8.8 values set out in the table above.

In one embodiment, the MTC has an elementals purity which is equal to or better than 0.7 times the EP8.8 values set out in the table above.

In one embodiment, the MTC has an elementals purity which is equal to or better than 0.5 times the EP8.8 values set out in the table above.

(For example, 0.5 times the EP8.8 values as set out above are 50 µg/g Al, 0.5 µg/g Cd, 50 µg/g Cr, etc.)

In one embodiment the MTC has a chromium level that is equal to or better than (i.e. lower than) 100 µg/g.

In one embodiment the MTC has a chromium level that is equal to or better than (i.e. lower than) 10 µg/g.

In one embodiment the MTC has a copper level that is equal to or better than (i.e. lower than) 300 µg/g.

In one embodiment the MTC has a copper level that is equal to or better than (i.e. lower than) 100 µg/g.

In one embodiment the MTC has a copper level that is equal to or better than (i.e. lower than) 10 µg/g.

In one embodiment the MTC has an iron level that is equal to or better than (i.e. lower than) 200 µg/g.

In one embodiment the MTC has an iron level that is equal to or better than (i.e. lower than) 100 µg/g.

All plausible and compatible combinations of the above purity grades are disclosed herein as if each individual combination was specifically and explicitly recited.

In particular embodiments, the MTC is a high purity MTC wherein 'high purity' is characterised by a purity of greater than 98% and one or more of the following:
 (i) less than 2% Azure B as impurity;
 (ii) less than 0.13% MVB (Methylene Violet Bernstein) as impurity; or
 (iii) an elementals purity better than the European Pharmacopeia limits of less than 100 µg/g Aluminium (Al); less than 1 µg/g Cadmium (Cd); less than 100 µg/g Chromium (Cr); less than 300 µg/g Copper (Cu); less than 10 µg/g Tin (Sn); less than 200 µg/g Iron (Fe); less than 10 µg/g Manganese (Mn); less than 1 µg/g Mercury (Hg); less than 10 µg/g Molybdenum (Mo); less than 10 µg/g Nickel (Ni); less than 10 µg/g Lead (Pb); and less than 100 µg/g Zinc (Zn).

In particular embodiments, the MTC is a high purity MTC wherein high-purity is characterised by a purity of greater than 98% and one or more of the following:
 (i) less than 1% Azure B as impurity;
 (ii) less than 0.15% Azure A as impurity;
 (iii) less than 0.15% Azure C as impurity;
 (iv) less than 0.13% Methylene Violet Bemthsen (MVB) as impurity;
 (v) an elementals purity better than the European Pharmacopeia limits of less than 100 µg/g Aluminium (Al); less than 1 µg/g Cadmium (Cd); less than 100 µg/g Chromium (Cr); less than 300 µg/g Copper (Cu); less than 10 µg/g Tin (Sn); less than 200 µg/g Iron (Fe); less than 10 µg/g Manganese (Mn); less than 1 µg/g Mercury (Hg); less than 10 µg/g Molybdenum (Mo); less than 10 µg/g Nickel (Ni); less than 10 µg/g Lead (Pb); and less than 100 µg/g Zinc (Zn).

In particular embodiments, the MTC is a high purity MTC wherein high-purity is characterised by a purity of greater than 98% and one or more of the following:

(i) less than 1% Azure B as impurity;
(ii) less than 0.15% Azure A as impurity;
(iii) less than 0.15% Azure C as impurity;
(iv) less than 0.05% Methylene Violet Bemthsen (MVB) as impurity; or
(v) an elementals purity better than the European Pharmacopeia limits of less than 100 µg/g Aluminium (Al); less than 1 µg/g Cadmium (Cd); less than 100 µg/g Chromium (Cr); less than 300 µg/g Copper (Cu); less than 10 µg/g Tin (Sn); less than 200 µg/g Iron (Fe); less than 10 µg/g Manganese (Mn); less than 1 µg/g Mercury (Hg); less than 10 µg/g Molybdenum (Mo); less than 10 µg/g Nickel (Ni); less than 10 µg/g Lead (Pb); and less than 100 µg/g Zinc (Zn).

In particular embodiments, the MTC is a high purity MTC wherein high-purity is characterised by at least 98% purity and less than 1% Azure B as impurity.

In particular embodiments, the MTC is a high purity MTC wherein high-purity is characterised by:

(i) at least 98% purity
(i) less than 1% Azure B as impurity; and
(ii) an elementals purity better than the European Pharmacopeia limits of less than 100 µg/g Aluminium (Al); less than 1 µg/g Cadmium (Cd); less than 100 µg/g Chromium (Cr); less than 300 µg/g Copper (Cu); less than 10 µg/g Tin (Sn); less than 200 µg/g Iron (Fe); less than 10 µg/g Manganese (Mn); less than 1 µg/g Mercury (Hg); less than 10 µg/g Molybdenum (Mo); less than 10 µg/g Nickel (Ni); less than 10 µg/g Lead (Pb); and less than 100 µg/g Zinc (Zn).

In particular embodiments, the MTC is a high purity MTC wherein high-purity is characterised by at least 98% purity and an elementals purity better than the European Pharmacopeia limits of less than 100 µg/g Aluminium (Al); less than 1 µg/g Cadmium (Cd); less than 100 µg/g Chromium (Cr); less than 300 µg/g Copper (Cu); less than 10 µg/g Tin (Sn); less than 200 µg/g Iron (Fe); less than 10 µg/g Manganese (Mn); less than 1 µg/g Mercury (Hg); less than 10 µg/g Molybdenum (Mo); less than 10 µg/g Nickel (Ni); less than 10 µg/g Lead (Pb); and less than 100 µg/g Zinc (Zn).

Methods for the production of 'high purity' diaminophenothiazinium compounds, including MTC, are described, for example, in WO2006/032879 and WO2008/007074 (WisTa Laboratories Ltd) and in WO2008/006979 (Provence Technologies).

A preferred MTC polymorph for use in the methods and compositions described herein is 'form A' described in WO2011/036561 which is a pentahydrate, at a "high purity" described above. That has a molecular weight of around 409.9. Based on a molecular weight of 284.1 for the $MT^+$ core, the weight factor for using this MT compound in the invention is 1.44.

Other weight factors can be calculated for example MT compounds herein, and the corresponding dosage ranges can be calculated therefrom.

Therefore the invention embraces a total daily dose of around 0.7 to 29 mg/day of $MTC \cdot 5H_2O$.

More preferably around 5 to 10 mg/day of $MTC \cdot 5H_2O$ total dose is utilised, which corresponds to about 3.5 to 7 mg MT.

Other example MT compounds are described in WO2007/110630. Their molecular weight (anhydrous) and weight factor is also shown:

| | Compound | Molecular weight | $MT^+$ anhydrous weight factor |
|---|---|---|---|
| 10 | $MTC \cdot 0.5ZnCl_2$ | 388.0 | 1.36 |
| 11 | MTI | 411.3 | 1.45 |
| 12 | MTI·HI | 539.2 | 2.73 |
| 13 | $MT \cdot NO_3$ | 346.4 | 1.22 |

The dosages described herein with respect to MT thus apply mutatis mutandis for these MT containing compounds, as adjusted for their molecular weight, and for choice of hydrate if used. For example $MTC \cdot 0.5ZnCl_2$ (also referred to as 'METHYLENE BLUE ZINC CHLORIDE DOUBLE SALT; CI 52015) may be obtained commercially as a monohydrate by several suppliers, which would have a molecular weight higher by 18, and correspondingly altered weight factor. MTI is reportedly available as a hemihydrate, Adsorption Factors As explained herein, the present inventors have determined that, unexpectedly, low doses of MT salts showed therapeutic benefits in a neurodegenerative disorder of protein aggregation. This was demonstrated using an example LMTX salt. This finding has implications for the dosing of both LMT and $MT^+$ salts.

The present inventors have determined that dosing with LMTX salts permits more efficient adsorption, compared with $MT^+$ salts. Typically MT adsorption may be around 1.5× greater when delivered as an LMTX salt as opposed to an $MT^+$ salts. This 1.5 factor may be termed herein an "adsorption factor".

Therefore in certain embodiments of the invention, the dosed amount of $MT^+$ salt may be higher than when using LMTX salt to achieve a similar plasma concentration.

Thus one preferred dosage of $MT^+$ salt may be about 5.25 to 10.5 mg MT, which is expected to provide a similar adsorbed dosage as 3.5 to 7 mg MT when delivered as LMTX.

Any of the MT compounds described herein, may be formulated with a reducing agent. In particular, $MT^+$ salts such as MTC may be formulated with a reducing agent such as ascorbate, and then lyophilized (as described in WO02/055720). This is expected to improve adsorption of the MT delivered by the compound.

In the various aspects of the invention described herein (as they relate to an MT-containing compound) this may optionally be any of those compounds described above:

In one embodiment, it is compound 1.
In one embodiment, it is compound 2.
In one embodiment, it is compound 3.
In one embodiment, it is compound 4.
In one embodiment, it is compound 5.
In one embodiment, it is compound 6.
In one embodiment, it is compound 7.
In one embodiment, it is compound 8.
In one embodiment, it is compound 9.
In one embodiment, it is compound 10.
In one embodiment, it is compound 11.
In one embodiment, it is compound 12.
In one embodiment, it is compound 13.

Or the compounds may be a hydrate, solvate, or mixed salt of any of these.

Accumulation Factors

As will be appreciated by those skilled in the art, for a given daily dosage, more frequent dosing will lead to greater accumulation of a drug.

The present inventors have derived estimated accumulation factors for MT as follows:

| Dosing | Observed plasma accumulation for MT | Relative accumulation |
|---|---|---|
| Once daily | 1.29$^{extrapolated}$ | 1 |
| Twice daily | 1.47 | 1.13 |
| Three-times daily | 1.65 | 1.28 |

For example, considering a total daily dose of 3.5 to 7 mg MT:

When given as a single daily dose, this may equate to an accumulation of MT in plasma of 4.5 to 8

When split b.i.d., this may equate to an accumulation of MT in plasma of 5.1 to 10.3

When split t.i.d., this may equate to an accumulation of MT in plasma of 5.8 to 11.6

Therefore in certain embodiments of the invention, the total daily dosed amount of MT compound may be lower, when dosing more frequently (e.g. twice a day [bid] or three times a day [tid]).

In one embodiment, LMTM is administered around 9 mg/once per day; 4 mg b.i.d.; 2.3 mg t.i.d (based on weight of LMTM)

In one embodiment, MTC:5H20 is administered around 10.6 mg/once per day; 6 mg b.i.d.; 2.8 mg t.i.d (based on weight of MTC:5H20).

Treatment and Prophylaxis

The term "treatment," as used herein in the context of treating a condition, pertains generally to treatment and therapy, whether of a human or an animal (e.g., in veterinary applications), in which some desired therapeutic effect is achieved, for example, the inhibition of the progress of the condition, and includes a reduction in the rate of progress, a halt in the rate of progress, regression of the condition, amelioration of the condition, and cure of the condition.

The term "therapeutically-effective amount," as used herein, pertains to that amount of a compound of the invention, or a material, composition or dosage from comprising said compound, which is effective for producing some desired therapeutic effect, commensurate with a reasonable benefit/risk ratio, when administered in accordance with a desired treatment regimen. The present inventors have demonstrated that a therapeutically-effective amount of an MT compound in respect of the diseases of the invention can be much lower than was hitherto understood in the art.

The invention also embraces treatment as a prophylactic measure is also included.

Thus the invention also provides
a method of prophylaxis of a neurodegenerative disorders of protein aggregation in a subject,
which method comprises orally administering to said patient an MT containing compound,
wherein said administration provides a total of between 0.5 and 20 mg of MT to the subject per day, optionally split into 2 or more doses.

The term "prophylactically effective amount," as used herein, pertains to that amount of a compound of the invention, or a material, composition or dosage from comprising said compound, which is effective for producing some desired prophylactic effect, commensurate with a reasonable benefit/risk ratio, when administered in accordance with a desired treatment regimen.

"Prophylaxis" in the context of the present specification should not be understood to circumscribe complete success i.e. complete protection or complete prevention. Rather prophylaxis in the present context refers to a measure which is administered in advance of detection of a symptomatic condition with the aim of preserving health by helping to delay, mitigate or avoid that particular condition.

Combination Treatments and Monotherapy

The term "treatment" includes "combination" treatments and therapies, in which two or more treatments or therapies for the same neurodegenerative disorder of protein aggregation, are combined, for example, sequentially or simultaneously. These may be symptomatic or disease modifying treatments.

The particular combination would be at the discretion of the physician.

In combination treatments, the agents (i.e., an MT compound as described herein, plus one or more other agents) may be administered simultaneously or sequentially, and may be administered in individually varying dose schedules and via different routes. For example, when administered sequentially, the agents can be administered at closely spaced intervals (e.g., over a period of 5-10 minutes) or at longer intervals (e.g., 1, 2, 3, 4 or more hours apart, or even longer periods apart where required), the precise dosage regimen being commensurate with the properties of the therapeutic agent(s).

An example of a combination treatment of the invention would be an agent which is MT-containing compound at the specified dosage in combination with an agent which is an inhibitor of amyloid precursor protein to beta-amyloid (e.g., an inhibitor of amyloid precursor protein processing that leads to enhanced generation of beta-amyloid).

In other embodiments the treatment is a "monotherapy", which is to say that the MT-containing compound is not used in combination (within the meaning discussed above) with another active agent for treating the same neurodegenerative disorder of protein aggregation in the subject.

As explained below, in the present invention, when treating AD at least, it is preferred that the treatment does not include administration of either or both of: an acetylcholinesterase inhibitor or an N-methyl-D-aspartate receptor antagonist. The MT-compound based treatment of AD may optionally be a monotherapy.

Duration of Treatment

For treatment of the neurodegenerative disorder of protein aggregation described herein, a treatment regimen based on the low dose MT compounds will preferably extend over a sustained period of time. The particular duration would be at the discretion of the physician.

For example, the duration of treatment may be:
At least 1, 2, 3, 4, 5, 6, 7, 8, 9, 10, 11, 12 months, or longer.
At least 2, 3, 4, 5 years, or longer.
Between 6 and 12 months.
Between 1 and 5 years.
Where the disorder is AD, duration may be such as to achieve any one or more of:
A 3, 4 or 5-point improvement on the 11-item Alzheimer's Disease Assessment Scale-cognitive subscale (ADAS-cog) over a 52-week period;
4, 5 or 6 point improvement on the 23-item Alzheimer's Disease Cooperative Study Activities of Daily Living (ADCS-ADL) over a 52-week period;
A reduction in the increase of Lateral Ventricular Volume (LVV), as measured by the Ventricular Boundary Shift Integral (VBSI) of 1 or 2 cm$^3$ over a 52-week period.
For prophylaxis, the treatment may be ongoing.

In all cases the treatment duration will generally be subject to advice and review of the physician.

Oral Dosage Forms

The MT compound of the invention, or pharmaceutical composition comprising it, is administered to a subject/patient orally.

Pharmaceutical Dosage Forms

Another aspect of the invention therefore provides a composition comprising a compound as described herein, and a pharmaceutically acceptable carrier or diluent.

In some embodiments, the composition is a pharmaceutical composition (e.g., formulation, preparation, medicament) comprising a compound as described herein, and a pharmaceutically acceptable carrier, diluent, or excipient.

The term "pharmaceutically acceptable," as used herein, pertains to compounds, ingredients, materials, compositions, dosage forms, etc., which are, within the scope of sound medical judgment, suitable for use in contact with the tissues of the subject in question (e.g., human) without excessive toxicity, irritation, allergic response, or other problem or complication, commensurate with a reasonable benefit/risk ratio. Each carrier, diluent, excipient, etc. must also be "acceptable" in the sense of being compatible with the other ingredients of the formulation.

In some embodiments, the composition is a pharmaceutical composition comprising at least one compound, as described herein, together with one or more other pharmaceutically acceptable ingredients well known to those skilled in the art, including, but not limited to, pharmaceutically acceptable carriers, diluents, excipients, adjuvants, fillers, buffers, preservatives, anti-oxidants, lubricants, stabilisers, solubilisers, surfactants (e.g., wetting agents), masking agents, colouring agents, flavouring agents, and sweetening agents.

In some embodiments, the composition further comprises other active agents, for example, other therapeutic or prophylactic agents.

Suitable carriers, diluents, excipients, etc. can be found in standard pharmaceutical texts. See, for example, Handbook of Pharmaceutical Additives, 2nd Edition (eds. M. Ash and I. Ash), 2001 (Synapse Information Resources, Inc., Endicott, New York, USA), Remington's Pharmaceutical Sciences, 20th edition, pub. Lippincott, Williams & Wilkins, 2000; and Handbook of Pharmaceutical Excipients, 2nd edition, 1994.

One aspect of the present invention pertains to a dosage unit (e.g., a pharmaceutical tablet or capsule) comprising an MT compound as described herein (e.g., obtained by, or obtainable by, a method as described herein; having a purity as described herein; etc.), and a pharmaceutically acceptable carrier, diluent, or excipient.

The "MT compound", although present in relatively low amount, is the active agent of the dosage unit, which is to say is intended to have the therapeutic or prophylactic effect in respect of a neurodegenerative disorder of protein aggregation. Rather, the other ingredients in the dosage unit will be therapeutically inactive e.g. carriers, diluents, or excipients. Thus, preferably, there will be no other active ingredient in the dosage unit, no other agent intended to have a therapeutic or prophylactic effect in respect of a disorder for which the dosage unit is intended to be used.

In some embodiments, the dosage unit is a tablet.

In some embodiments, the dosage unit is a capsule.

In some embodiments, said capsules are gelatine capsules.

In some embodiments, said capsules are HPMC (hydroxypropylmethylcellulose) capsules.

In some embodiments, the amount of MT in the unit is 0.5 to 10 mg.

An example dosage unit may contain 1 to 10 mg of MT.

A further example dosage unit may contain 2 to 9 mg of MT.

A further example dosage unit may contain 3 to 8 mg of MT.

A further preferred dosage unit may contain 3.5 to 7 mg of MT.

A further preferred dosage unit may contain 4 to 6 mg of MT.

In some embodiments, the amount is about 1, 1.5, 2, 2.5, 3, 3.5, 4, 5, 6, 7, 8, 9, 10 mg of MT.

Using the weight factors described or explained herein, one skilled in the art can select appropriate amounts of an MT containing compound to use in oral formulations.

As explained above, the MT weight factor for LMTM is 1.67. Since it is convenient to use unitary or simple fractional amounts of active ingredients, non-limiting example LMTM dosage units may include 1.5, 2, 2.5, 3, 3.5, 4, 5, 6, 7, 8, 9, 10, 15, 16, 17, 18 mg etc.

As explained above, the MT weight factor for MTC·5H$_2$0 is 1.44. Since it is convenient to use unitary or simple fractional amounts of active ingredients, non-limiting example MTC·5H$_2$0 dosage units may include 1.5, 2, 2.5, 3, 3.5, 4, 5, 6, 7, 8, 9, 10, 15, 18, 20 mg etc.

Nutraceutical Compositions

The "nutraceutical compositions" of the invention comprise a low dose of MT compound, as described herein, in combination with one or more nutrients in an edible form (for example an oral dosage form).

The novel nutraceutical compositions of the invention can find use as supplements to food and beverages, and as pharmaceutical compositions.

"Nutrients" as used herein refers to the components of nutraceutical compositions that serve a biochemical and/or physiological role in the human or animal body. "Nutrients" includes such substances as vitamins, minerals, trace elements, micronutrients, antioxidants and the like, as well as other bioactive materials, such as enzymes, or compounds biosynthetically produced by human or animal enzymes; as well as herbs and herbal extracts; fatty acids, amino acids and derivatives thereof.

"Edible form" denotes a composition that can be ingested directly or converted to an ingestible form, such as, by dissolving in water.

Alternatively, the nutraceutical composition can be in the form of a food or drink, such as a defined portion of a foodstuff (which term includes both food or drink) supplemented with the defined dosage of MT compound. These foodstuffs will typically comprise one or more of a fat, a protein, or a carbohydrate.

The term "nutraceutical" as used herein denotes a usefulness in both the nutritional and pharmaceutical field of application, and the disclosure herein relating to pharmaceutical dosage forms applies mutatis mutandis to the nutraceutical compositions.

Oral dosage forms particularly suitable for nutraceutical compositions are well known in the art and described in more detail elsewhere herein. They include powders, capsules, pills, tablets, caplets, gelcaps, and defined portions of edible food items. Liquid forms include solutions or suspensions. General examples of dosage forms and nutraceutical forms are given, for example in WO2010/078659.

Some examples of nutrients useful in the compositions of the present invention are as follows. Any combination of these nutrients is envisaged by the present invention:

Vitamins

It is reported that B-vitamin supplementation (folic acid [folate, vitamin $B_9$], vitamin $B_{12}$, vitamin $B_6$) can slow the atrophy of specific brain regions that are a key component of the AD process and that are associated with cognitive decline. This is particularly the case for elderly subjects with high homocysteine levels (Douaud, Gwenaëlle, et al. "Preventing Alzheimer's disease-related gray matter atrophy by B-vitamin treatment." Proceedings of the National Academy of Sciences 110.23 (2013): 9523-9528; see also Quadri, Pierluigi, et al. "Homocysteine, folate, and vitamin $B_{12}$ in mild cognitive impairment, Alzheimer disease, and vascular dementia." The American journal of clinical nutrition 80.1 (2004): 114-122; Rosenberg I H, Miller J W. Nutritional factors in physical and cognitive functions of elderly people. The American journal of clinical nutrition. 1992 Jun. 1:55 (6):1237S-1243S.).

It has been suggested that, along with other antioxidants (see below), vitamin C may have utility in protecting neural tissue, as well as potentially decreasing β-amyloid generation and acetylcholinesterase activity and prevents endothelial dysfunction by regulating nitric oxide (see e.g. Heo J H, Hyon-Lee, Lee K M. The possible role of antioxidant vitamin C in Alzheimer's disease treatment and prevention. American Journal of Alzheimer's Disease & Other Dementias. 2013 March; 28(2):120-5).

It has also been suggested that Vitamin E supplementation may have a role to play in AD treatment (see e.g. Mangialasche, Francesca, et al. "Serum levels of vitamin E forms and risk of cognitive impairment in a Finnish cohort of older adults." Experimental gerontology 48.12 (2013): 1428-1435).

Micronutrients, Antioxidants

Micronutrients or antioxidants, such as polyphenols, have been reported to have benefits in relation to protection or treatment of age-related diseases including neurodegenerative ones, particularly cognitive impairment and AD.

Micronutrients and\or antioxidants which may be utilised in the nutraceutical compositions described herein include the flavonoids shown in the Table below (reproduced from Mecocci, Patrizia, et al. "Nutraceuticals in cognitive impairment and Alzheimer's disease." Frontiers in pharmacology 5:147 (2014)):

Flavonoid Chemical Subgroups and Relative Food Sources:

| Groups | Molecules | Food source |
| --- | --- | --- |
| FLAVANOLS | Catechin, epicatechin, epigallocathechin, epigallocatechin gallate (EGCG) | Cocoa and chocolate, green tea, grapes |
| FLAVONOLS | Kaempferol, quercetin | Onions, apples, green tea, capers, leeks, broccoli |
| FLAVONES | Luteolin, apigenin | Celery, parsley, rosemary |
| ISOFLAVONES | Daidzein, genistein | Soy |
| FLAVANONES | Hesperetin, naringenin | Citrus fruit, tomatoes |
| ANTHOCYANIDINS | Pelargonidin, cyanidine, malvidin | Berry fruits, red wine |

Other micronutrients having potential utility in relation to protection or treatment of age-related diseases, and described by Mecocci et al include:

Non-flavonoid polyphenols: resveratrol and curcumin,
Carotenoids: lycopene, lutein, zeaxanthin, β-cryptoxanthin, α-carotene, and the most prominent carotenoid, β-carotene,
Crocin (the main chemical compound identified in saffron),
Diterpenes: for example carnosic and rosmarinic acids are two of the most important antioxidant compounds in rosemary.

Herbs and Plant Extracts

In addition to the plants described or cross-referenced above in relation to micronutrients and antioxidants, other plant extracts and herbs are reported to have benefit in CNS disorders—see Kumar, Vikas. "Potential medicinal plants for CNS disorders: an overview." Phytotherapy Research 20.12 (2006): 1023-1035. These include Ginkgo biloba, Hypericum perforatum (St John's wort). Piper methysticum Forst. (Family Piperaceae) also called kava kava, Valeiana offcinalis L. (Valerian), Bacopa monniera (which in India is locally known as Brahmi or Jalanimba). Convolvulus pluricaulis (also known as Shankhpushpi or shankapushpi)

Oils and Fats

It is reported that ω-3 polyunsaturated fatty acid (PUFA), for example, may be a promising tool for preventing age-related brain deterioration. Sources of PUFA such as (docosahexaenoic acid (DHA, 22:6) and eicosapentenoic acid (EPA, 20:5) include fish oils (Denis. I., et al. "Omega-3 fatty acids and brain resistance to ageing and stress: body of evidence and possible mechanisms." Ageing research reviews 12.2 (2013): 579-594.)

Immediate Release Dosage Units

The formulations and compositions (especially pharmaceutical compositions) may be prepared to provide for rapid or slow release; immediate, delayed, timed, or sustained release; or a combination thereof.

An immediate release product allows the ingredient or active moiety to dissolve in the gastrointestinal tract, without causing any delay or prolongation of the dissolution or absorption of the drug. Requirements for dissolution testing of immediate release products are set out in the Guidance for Industry (CDER 1997) "Dissolution testing for immediate release solid oral dosage forms", (CDER 1997) "Immediate release solid oral dosage forms—Scale up and Post approval Changes", ICH Guidance Q6A, Specifications: Test Procedures and Acceptance Criteria For New Drug Substances And New Drug Products. The most commonly employed dissolution test methods as described in the USP and European Pharmacopeia (6th edition) are the basket method (USP 1) and the paddle method (USP 2). The described methods are simple, robust, well standardized, and used worldwide. They are flexible enough to allow dissolution testing for a variety of drug products. The following parameters influencing the dissolution behaviour may for example be relevant for selecting the appropriate in vitro dissolution test conditions for an immediate release solid oral product: apparatus, stirring speed, dissolution medium and temperature. Because of the biopharmaceutical properties of MTC and its expected desirable absorption characteristics in the upper gastrointestinal tract, it was preferable to produce rapidly dissolving tablets of MTC.

Compositions according to the invention can be dissolution tested in a USP-2 apparatus in 900 ml of 0.1N HCl, with paddles rotating at 50-75 rpm. Compositions according to the invention exhibit at least the acceptance criteria cited for Stage 1 (S1) testing in the USP 32 (The United States Pharmacopeia, edited by the United States Pharmacopeial Convention, Inc., 12601 Twinbrook Parkway, Rockville, MD 20852; Published by Rand McNally, Inc., 32nd Edition, 2008):

Acceptance Criteria: Each tablet achieved 85% dissolution of MTC within 30 minutes after insertion of the coated tablet into the 0.1N HCl.

Thus in some embodiments, the MTC based formulations of the invention, when evaluated using this method, provide at least:

75% dissolution of MTC within 45 minutes after insertion of the coated tablet into the 0.1N HCl; or 85% dissolution of MTC within 30 minutes after insertion of the coated tablet into the 0.1N HCl;

85% dissolution of MTC within 15 minutes after insertion of the coated tablet into the 0.1N HCl.

Another aspect of the present invention pertains to methods of making a low dosage MT compound pharmaceutical composition comprising admixing at least one MT compound, as defined herein, together with one or more other pharmaceutically acceptable ingredients well known to those skilled in the art, e.g., carriers, diluents, excipients, etc. If formulated as discrete units (e.g., tablets, etc.), each unit contains a predetermined amount (dosage) of the compound.

The formulations may be prepared by any methods well known in the art of pharmacy. Such methods include the step of bringing into association the compound with a carrier which constitutes one or more accessory ingredients. In general, the formulations are prepared by uniformly and intimately bringing into association the compound with carriers (e.g., liquid carriers, finely divided solid carrier, etc.), and then shaping the product, if necessary.

In some embodiments, the pharmaceutically acceptable carrier, diluent, or excipient is or comprises one or both of a glyceride (e.g., Gelucire 44/14 @; lauroyl macrogol-32 glycerides PhEur. USP) and colloidal silicon dioxide (e.g., 2% Aerosil 200 ®; Colliodal Silicon Dioxide PhEur, USP).

Preferably the pharmaceutical compositions comprising a compound of the invention, in solid dosage form. The composition preferably further comprises at least one diluent suitable for dry compression. The pharmaceutical composition is characterised in that the compound exists in a substantially stable form.

The pharmaceutical composition will generally also include a lubricant. Examples of lubricants include magnesium stearate, calcium stearate, sodium stearyl fumarate, stearic acid, glycerylbehaptate, polyethylene glycol, ethylene oxide polymers (for example, those available under the registered trademark Carbowax from Union Carbide, Inc., Danbury, CT), sodium lauryl sulphate, magnesium lauryl stearate, mixtures of magnesium stearate with sodium lauryl sulphate, and hydrogenated vegetable oil. Preferred lubricants include calcium stearate, magnesium stearate and sodium stearyl fumarate. Most preferred as the lubricant is magnesium stearate. Lubricants generally comprise from about 0.5 to about 5.0% of the total (uncoated) tablet weight. The amount of lubricant employed is generally from about 1.0 to about 2.0%, preferably 0.5 to 2.0% w/w.

In addition to the diluent(s) and lubricant(s), other conventional excipients may also be present in the pharmaceutical compositions of the invention. Such additional excipients include disintegrants, binders, flavouring agents, colours and glidants. Some excipients can serve multiple functions, for example as both binder and tablet disintegrant.

A tablet disintegrant may be present in an amount necessary to achieve rapid dissolution. Disintegrants are excipients which oppose the physical forces of particle bonding in a tablet or capsule when the dosage form is placed in an aqueous environment. Examples of disintegrants include crosslinked polyvinylpyrrofidone (crospovidone), sodium starch glycolate, crosslinked sodium carboxymethyl cellulose (sodium croscarmellose), and pregelatinized starch. Generally the amount of disintegrant can be from 0 to about 25% w/w, more commonly from about 1% to about 15% w/w, and usually less than 10% or less than 5% w/w, of the composition.

Binders are excipients which contribute to particle adhesion in a solid formulation. Examples of binders include cellulose derivatives (carboxymethylcellulose, hydroxypropyl methylcellulose, hydroxypropyl cellulose, hydroxyethylcellulose, ethylcellulose, microcrystalline cellulose) and sugars such as lactose, sucrose, dextrose, glucose, maltodextrin, and mannitol, xylitol, polymethacrylates, polyvinylpyrrolidone, sorbitol, pregelatinized starch, alginic acids, and salts thereof such as sodium alginate, magnesium aluminum silicate, polyethylene glycol, carrageenan and the like. Generally, the amount of binder can vary widely, eg from 0% to 95% w/w of the composition. As noted above, excipients may serve multiple functions. For instance, the tabletting diluent may also serve as a binder.

Glidants are substances added to a powder to improve its flowability. Examples of glidants include magnesium stearate, colloidal silicon dioxide (such as the grades sold as Aerosil), starch and talc. Glidants may be present in the pharmaceutical composition at a level of from 0 to about 5% w/w. Again, however, it should be noted that excipients may serve multiple functions. The lubricant, for example magnesium stearate, may also function as a glidant.

Examples of colours that may be incorporated into the pharmaceutical compositions of the invention include titanium dioxide and/or dyes suitable for food such as those known as FD&C dyes and natural colouring agents. A colouring agent is unlikely to be used in the powder mixture that is compressed in accordance with the aspects of the invention discussed above, but may form part of a coating applied to the composition, as described below, in which case the colouring agent may be present in the film coat in an amount up to about 2.0% w/w.

The tablet is desirably coated with a conventional film coating which imparts toughness, ease of swallowing, and an elegant appearance to the final product. Many polymeric film-coating materials are known in the art. A preferred film-coating material is hydroxypropylmethylcellulose (HPMC) or polyvinyl alcohol-part hydrolysed (PVA). HPMC and PVA may be obtained commercially, for example from Colorcon, in coating formulations containing excipients which serve as coating aids, under the registered trademark Opadry. Opadry formulations may also contain talc, polydextrose, triacetin, polyethyleneglycol, polysorbate 80, titanium dioxide, and one or more dyes or lakes. Other suitable film-forming polymers may also be used, including hydroxypropylcellulose, vinyl copolymers such as polyvinyl pyrollidone and polyvinyl acetate, and acrylate-methacrylate copolymers. Use of a film coating is beneficial for ease of handling and because a blue coloured uncoated core may stain the inside of the mouth during swallowing. Coating also improves light stability of the dosage form.

Coating of the tablets may conveniently be carried out using a conventional coating pan. In preferred embodiments of the process, the coating pan is pre-heated using heated inlet air until the exhaust temperature reaches 35°–55° C., more preferably 40-50° C. This may typically require application of heated inlet air at an inlet temperature of 45-75° C., preferably 50-65° C., for 10-15 minutes. The tablet cores containing the active ingredient (e.g. LMTM) are then added to the coating pan and the aqueous film coat applied. The spray rate is controlled such that the bed temperature is maintained at 38-48° C., more preferably 42-44° C., until the desired weight gain (coating weight) has been achieved.

Subjects, Patients and Patient Groups

The subject/patient may be an animal, a mammal, a placental mammal, a rodent (e.g., a guinea pig, a hamster, a rat, a mouse), murine (e.g., a mouse), a lagomorph (e.g., a rabbit), avian (e.g., a bird), canine (e.g., a dog), feline (e.g., a cat), equine (e.g., a horse), porcine (e.g., a pig), ovine (e.g., a sheep), bovine (e.g., a cow), a primate, simian (e.g., a monkey or ape), a monkey (e.g., marmoset, baboon), a monotreme (e.g. platypus), an ape (e.g., gorilla, chimpanzee, orangutan, gibbon), or a human.

In preferred embodiments, the subject/patient is a human who has been diagnosed as having one of the cognitive or CNS disorders described herein, or (for prophylactic treatment) assessed as being susceptible to one of the neurodegenerative disorders of protein aggregation (e.g. cognitive or CNS disorder) described herein—for example based on familial or genetic or other data.

The patient may be an adult human, and the dosages described herein are premised on that basis (typical weight 50 to 70 kg). If desired, corresponding dosages may be utilised for subjects outside of this range by using a subject weight factor whereby the subject weight is divided by 60 kg to provide the multiplicative factor for that individual subject.

The low dosage treatments of the present invention increase the feasibility of purely prophylactic treatments, since the reduced concentration of active ingredients inevitably reduces risk of any adverse side effects (and increases the safety profile) and hence increases the risk/benefit ratio for such prophylactic treatments.

Thus, for example, for diagnosis of AD, and assessment of severity, the initial selection of a patient may involve any one or more of: rigorous evaluation by experienced clinician; exclusion of non-AD diagnosis as far as possible by supplementary laboratory and other investigations; objective evaluation of level of cognitive function using neuropathologically validated battery.

Diagnosis of AD and other disorders described herein can be performed by physicians by methods well known to those skilled in the art.

As explained herein, in the present invention it is preferred that the subject or patient group, if they are being treated in respect of AD, is one who is not receiving treatment with any of: an acetylcholinesterase inhibitor or an N-methyl-D-aspartate receptor antagonist. Examples of acetylcholinesterase inhibitors include Donepezil (Aricept™), Rivastigmine (Exelon™) or Galantamine (Reminyl™). An examples of an NMDA receptor antagonist is Memantine (Ebixa™, Namenda™).

Based on the findings described herein, these selection criteria are likely to be applicable when treating AD with MT$^+$ compounds even at higher doses than those described herein e.g. between 0.5 mg and 300 mg total daily dose per day.

Thus in one aspect the present invention provides a method of treatment (or prophylaxis) of AD in a subject,
which method comprises orally administering to said subject a methylthioninium (MT) containing compound,
with the proviso that said treatment does not include administration of either or both of an acetylcholinesterase inhibitor or an N-methyl-D-aspartate receptor antagonist.

Unless context demands otherwise, the disclosure made herein regarding the "low dose" treatments of neurodegenerative diseases more generally applies mutatis mutandis to these aspects of the invention.

For example the AD subject or patient group may be entirely naïve to these other treatments, and have not historically received one or both of them.

For example the AD subject or patient group may have historically received one or both of them, but ceased that medication at least 1, 2, 3, 4, 5, 6, 7 days, or 2, 3, 4, 5, 6, 7, 8, 12, or 16 weeks, or more preferably at least 1, 2, 3, 4, 5 or 6 months etc. prior to treatment with an MT compound according to the present invention.

Any aspect of the present invention may include the active step of selecting the AD subject or patient group according to these criteria, or selecting an AD subject or patient group who is or are receiving treatment with either or both an acetylcholinesterase inhibitor or an N-methyl-D-aspartate receptor antagonist, and discontinuing that treatment (instructing the subject or patient group to discontinue that treatment) prior to treatment with an MT compound according to the present invention.

Labels, Instructions and Kits of Parts

The unit dosage compositions described herein (e.g. a low dose MT containing compound plus optionally other ingredients, or MT composition more generally for treatment in AD) may be provided in a labelled packet along with instructions for their use.

In one embodiment, the pack is a bottle, such as are well known in the pharmaceutical art. A typical bottle may be made from pharmacopoeial grade HDPE (High-Density Polyethylene) with a childproof, HDPE pushlock closure and contain silica gel desiccant, which is present in sachets or canisters. The bottle itself may comprise a label, and be packaged in a cardboard container with instructions for us and optionally a further copy of the label.

In one embodiment, the pack or packet is a blister pack (preferably one having aluminium cavity and aluminium foil) which is thus substantially moisture-impervious. In this case the pack may be packaged in a cardboard container with instructions for us and label on the container.

Said label or instructions may provide information regarding the neurodegenerative disorders of protein aggregation (e.g. cognitive or CNS disorder) for which the medication is intended.

Where the medication is indicated for AD, said label or instructions may provide information instructing the user that the compositions should not be used in conjunction with any of: an acetylcholinesterase inhibitor or an N-methyl-D-aspartate receptor antagonist.

Said label or instructions may provide information regarding the maximum permitted daily dosage of the compositions as described herein—for example based on once daily, b.i.d., or t.i.d.

Said label or instructions may provide information regarding the suggested duration of treatment, as described herein.

Reversing and/or Inhibiting the Aggregation of a Protein

One aspect of the invention is the use of an MT compound or composition as described herein, to regulate (e.g., to reverse and/or inhibit) the aggregation of a protein, for example, aggregation of a protein associated with a neurodegenerative disease and/or clinical dementia. The aggregation will be associated with a disease state as discussed below.

Similarly, one aspect of the invention pertains to a method of regulating (e.g., reversing and/or inhibiting) the aggregation of a protein in the brain of a mammal, which aggregation is associated with a disease state as described herein, the treatment comprising the step of administering to said mammal in need of said treatment, a prophylactically or therapeutically effective amount of an MT compound or composition as described herein, that is an inhibitor of said aggregation.

Disease conditions treatable via the present invention are discussed in more detail below.

Methods of Treatment

Another aspect of the present invention, as explained above, pertains to a method of treatment comprising administering to a patient in need of treatment a prophylactically or therapeutically effective amount of a compound as described herein, preferably in the form of a pharmaceutical composition.

Use in Methods of Therapy

Another aspect of the present invention pertains to a compound or composition as described herein, for use in a method of treatment (e.g., of a disease condition) of the human or animal body by therapy.

Use in the Manufacture of Medicaments

Another aspect of the present invention pertains to use of an MT compound or composition as described herein, in the manufacture of a medicament for use in treatment (e.g., of a disease condition).

In some embodiments, the medicament is a composition e.g. a low-dose unit dose composition as described herein.

Diseases of Protein Aggregation

The compounds and compositions of the present invention are useful in the treatment or prophylaxis of diseases of protein aggregation.

Thus, in some embodiments, the disease condition is a disease of protein aggregation, and, for example, the treatment is with an amount of a compound or composition as described herein, sufficient to inhibit the aggregation of the protein associated with said disease condition.

The following Table lists various disease-associated aggregating proteins and the corresponding neurodegenerative disease of protein aggregation. The use of the compounds and compositions of the invention in respect of these proteins or diseases is encompassed by the present invention.

| | | Diseases of protein aggregation | | |
|---|---|---|---|---|
| Protein | Disease | Aggregating domain and/or mutations | Fibril subunit size (kDa) | Reference |
| | | Neurodegenerative disorders | | |
| Prion protein | Prion diseases | Inherited and sporadic forms | 27 | Prusiner (1998) |
| | (CJD, nvCJD, Fatal familial insomnia, Gerstmann-Straussler-Scheinker syndrome, Kuril) | PrP-27-30; many mutations. | 27 | Prusiner (1998) |
| | | Fibrillogenic domains: 113-120, 178-191, 202-218. | | Gasset et al. (1992) |
| Tau protein | Alzheimer's disease, Down's syndrome, FTDP-17, CBD, post-encephalitic parkinsonism, Pick's disease, parkinsonism with dementia complex of Guam | Inherited and sporadic forms | 10-12 | Wischik et al. (1988) |
| | | Truncated tau (tubulin-binding domain) 297-391. | 10-12 | Wischik et al. (1988) |
| | | Mutations in tau in FTDP-17. | | Hutton et al. (1998) |
| | | Many mutations in presenilin proteins. | | Czech et al. (2000) |
| Amyloid β-protein | Alzheimer's disease, Down's syndrome | Inherited and sporadic forms | 4 | Glenner & Wong, (1984) |
| | | Amyloid β-protein; 1-42(3). | 4 | Glenner & Wong, (1984) |
| | | Mutations in APP in rare families. | | Goate et al. (1991) |
| Huntingtin | Huntington's disease | N-termini of protein with expanded glutamine repeats. | 40 | DiFiglia et al. (1997) |
| Ataxin) | Spinocerebellar ataxias (SCA1, 2, 3, 7) | Proteins with expanded glutamine repeats. | | Paulson et al. (1999) |
| Atrophin | Dentatorubropallidoluysian atrophy (DRPLA) | Proteins with expanded glutamine repeats. | | Paulson et al. (1999) |

-continued

Diseases of protein aggregation

| Protein | Disease | Aggregating domain and/or mutations | Fibril subunit size (kDa) | Reference |
|---|---|---|---|---|
| | | Neurodegenerative disorders | | |
| Androgen receptor | Spinal and bulbar muscular atrophy | Proteins with expanded glutamine repeats. | | Paulson et al. (1999) |
| Neuroserpin | Familial encephalopathy with neuronal inclusion bodies (FENIB) | Neuroserpin; S49P, S52R. | 57 | Davis et al. (1999) |
| α-Synuclein | Parkinson's disease, dementia with Lewy bodies, multiple system atrophy | Inherited and sporadic forms | 19 | Spillantini et al. (1998) also PCT/GB2007/001105 |
| | | A53T, A30P in rare autosomal-dominant PD families. | | Polymeropoulos et al. (1997) |
| TDP-43 | FTLD-TDP | Several TDP-43 mutations | 10-43 | Mackenzie et al. (2010) |
| | Amyotrophic lateral sclerosis | Several TDP-43 mutations | 10-43 | Mackenzie et al. (2010) |
| Cystatin C | Hereditary cerebral angiopathy (Icelandic) | Cystatin C less 10 residues; L68Q. | 12-13 | Abrahamson et al. (1992) |
| Superoxide dismutase 1 | Amyotrophic lateral sclerosis | SOD1 mutations. | 16 | Shibata et al. (1996) |

As described in WO 02/055720. WO2007/110630, and WO2007/110627, diaminophenothiazines have utility in the inhibition of such protein aggregating diseases.

Thus it will be appreciated that, except where context requires otherwise, description of embodiments with respect to tau protein or tau-like proteins (e.g., MAP2; see below), should be taken as applying equally to the other proteins discussed herein (e.g., β-amyloid, synuclein, prion, etc.) or other proteins which may initiate or undergo a similar pathological aggregation by virtue of conformational change in a domain critical for propagation of the aggregation, or which imparts proteolytic stability to the aggregate thus formed (see, e.g., the article by Wischik et al. in "Neurobiology of Alzheimer's Disease", 2nd Edition, 2000, Eds. Dawbam, D. and Allen, S. J., The Molecular and Cellular Neurobiology Series, Bios Scientific Publishers, Oxford). All such proteins may be referred to herein as "aggregating disease proteins."

Likewise, where mention is made herein of "tau-tau aggregation", or the like, this may also be taken to be applicable to other "aggregating-protein aggregation", such as β-amyloid aggregation, prion aggregation, synuclein aggregation, etc. The same applies for "tau proteoiytic degradation" etc.

Preferred Aggregating Disease Target Proteins

Preferred embodiments of the invention are based on tau protein. The term "tau protein," as used herein, refers generally to any protein of the tau protein family. Tau proteins are characterised as being one among a larger number of protein families which co-purify with microtubules during repeated cycles of assembly and disassembly (see, e.g., Shelanski et al., 1973, Proc. Natl. Acad. Sci. USA, Vol. 70, pp. 765-768), and are known as microtubule-associated-proteins (MAPs). Members of the tau family share the common features of having a characteristic N-terminal segment, sequences of approximately 50 amino acids inserted in the N-terminal segment, which are developmentally regulated in the brain, a characteristic tandem repeat region consisting of 3 or 4 tandem repeats of 31-32 amino acids, and a C-terminal tail.

MAP2 is the predominant microtubule-associated protein in the somatodendritic compartment (see, e.g., Matus, A., in "Microtubules" [Hyams and Lloyd, Eds.] pp. 155-166, John Wiley and Sons, New York, USA). MAP2 isoforms are almost identical to tau protein in the tandem repeat region, but differ substantially both in the sequence and extent of the N-terminal domain (see, e.g., Kindler and Gamer, 1994, Mol. Brain Res., Vol. 26, pp. 218-224). Nevertheless, aggregation in the tandem-repeat region is not selective for the tau repeat domain. Thus it will be appreciated that any discussion herein in relation to tau protein or tau-tau aggregation should be taken as relating also to tau-MAP2 aggregation, MAP2-MAP2 aggregation, and so on.

In some embodiments, the protein is tau protein.

In some embodiments, the protein is a synuclein, e.g., α- or β-synuclein.

In some embodiments, the protein is TDP-43.

TAR DNA-Binding Protein 43 (TDP-43) is a 414 amino acid protein encoded by TARDBP on chromosome 1p36.2. The protein is highly conserved, widely expressed, and predominantly localised to the nucleus but can shuttle between the nucleus and cytoplasm (Mackenzie et al 2010). It is involved in transcription and splicing regulation and may have roles in other processes, such as: microRNA processing, apoptosis, cell division, stabilisation of messenger RNA, regulation of neuronal plasticity and maintenance of dendritic integrity. Furthermore, since 2006 a substantial body of evidence has accumulated in support of the TDP-43 toxic gain of function hypothesis in amyotrophic lateral sclerosis (ALS). TDP-43 is an inherently aggregation-prone protein and aggregates formed in vitro are ultrastructurally similar to the TDP-43 deposits seen in degenerating neurones in ALS patients (Johnson et al 2009). Johnson et al (2008) showed that when TDP-43 is overexpressed in a yeast model only the aggregated form is toxic. Several in vitro studies have also shown that C-terminal fragments of TDP-43 are more likely than full-length TDP-43 to form insoluble cytoplasmic aggregates that become ubiquitinated, and toxic to cells (Arai et al 2010; Igaz et al 2009; Nonaka et al 2009; Zhang et al 2009). Though Nonaka et al (2009) suggested that these cytoplasmic aggregates bind the endogenous full-length protein depleting it from the nucleus, Zhang et al (2009) found retention of normal nuclear expression, suggesting a purely toxic effect for the aggregates. Yang et al (2010) have described the capture of full-length TDP-43 within aggregates of C- and N-terminal fragments of TDP-43 in NSC34 motor neurons in culture. Neurite outgrowth, impaired as a result of the presence of such truncated fragments, could be rescued by overexpression of the full-length protein. Although the role of neurite outgrowth in vivo has not been established, this model would support the suggestion made by Nonaka and colleagues for a role of TDP-43 aggregation in ALS pathogenesis.

Mutant TDP-43 expression in cell cultures has repeatedly been reported to result in increased generation of C-terminal fragments, with even greater cytoplasmic aggregation and toxic effects than the wild-type protein (Kabashi et al 2008; Sreedharan et al 2008; Johnson et al 2009; Nonaka et al 2009; Arai et al 2010; Barmarda et al 2010; Kabashi et al 2010).

Where the protein is tau protein, in some embodiments of the present invention, there is provided a method of inhibiting production of protein aggregates (e.g. in the form of paired helical filaments (PHFs), optionally in neurofibrillary tangles (NFTs) in the brain of a mammal, the treatment being as described above.

Preferred Indications—Diseases of Protein Aggregation

In one embodiment the present invention is used for the treatment of Alzheimer's disease (AD)—for example mild, moderate or severe AD.

Notably it is not only Alzheimer's disease (AD) in which tau protein (and aberrant function or processing thereof) may play a role. The pathogenesis of neurodegenerative disorders such as Pick's disease and progressive supranuclear palsy (PSP) appears to correlate with an accumulation of pathological truncated tau aggregates in the dentate gyrus and stellate pyramidal cells of the neocortex, respectively. Other dementias include frontotemporal dementia (FTD); FTD with parkinsonism linked to chromosome 17 (FTDP-17); disinhibition-dementia-parkinsonism-amyotrophy complex (DDPAC); pallido-ponto-nigral degeneration (PPND); Guam-ALS syndrome; pallido-nigro-luysian degeneration (PNLD); cortico-basal degeneration (CBD) and others (see, e.g., the article by Wischik et al. in "Neurobiology of Alzheimer's Disease", 2nd Edition, 2000, Eds. Dawbam, D. and Allen, S. J., The Molecular and Cellular Neurobiology Series, Bios Scientific Publishers, Oxford; especially Table 5.1). All of these diseases, which are characterized primarily or partially by abnormal tau aggregation, are referred to herein as "tauopathies".

Thus, in some embodiments, the disease condition is a tauopathy.

In some embodiments, the disease condition is a neurodegenerative tauopathy.

In some embodiments, the disease condition is selected from Alzheimer's disease (AD), Pick's disease, progressive supranuclear palsy (PSP), fronto temporal dementia (FTD), FTD with parkinsonism linked to chromosome 17 (FTDP 17), frontotemporal lobar degeneration (FTLD) syndromes; disinhibition-dementia-parkinsonism-amyotrophy complex (DDPAC), pallido-ponto-nigral degeneration (PPND), Guam-ALS syndrome, pallido nigro luysian degeneration (PNLD), cortico-basal degeneration (CBD), dementia with argyrophilic grains (AgD), dementia pugilistica (DP) or chronic traumatic encephalopathy (CTE), Down's syndrome (DS), dementia with Lewy bodies (DLB), subacute sclerosing panencephalitis (SSPE), MCI, Niemann-Pick disease, type C (NPC), Sanfilippo syndrome type B (mucopolysaccharidosis Ill B), or myotonic dystrophies (DM). DM1 or DM2, or chronic traumatic encephalopathy (CTE).

In some embodiments, the disease condition is a lysosomal storage disorder with tau pathology. NPC is caused by mutations in the gene NPC1, which affects cholesterol metabolism (Love et al 1995) and Sanfilippo syndrome type B is caused by a mutation in the gene NAGLU, in which there is lysosomal accumulation of heparin sulphate (Ohmi et al. 2009). In these lysosomal storage disorders, tau pathology is observed and its treatment may decrease the progression of the disease. Other lysosomal storage disorders may also be characterised by accumulation of tau.

Use of phenothiazine diaminium salts in the treatment of Parkinson's disease and MCI is described in more detail in PCT/GB2007/001105 and PCT/GB2008/002066.

In some embodiments, the disease condition is Parkinson's disease, MCI, or Alzheimer's disease.

In some embodiments, the disease condition is Huntington's disease or other polyglutamine disorder such as spinal bulbar muscular atrophy (or Kennedy disease), and dentatorubropallidoluysian atrophy and various spinocerebellar ataxias.

In some embodiments, the disease condition is an FTLD syndrome (which may for example be a tauopathy or TDP-43 proteinopathy, see below).

In some embodiments, the disease condition is PSP or ALS.

TDP-43 proteinopathies include amyotrophic lateral sclerosis (ALS; ALS-TDP) and frontotemporal lobar degeneration (FTLD-TDP).

The role of TDP-43 in neurodegeneration in ALS and other neurodegenerative disorders has been reviewed in several recent publications (Chen-Plotkin et al 2010; Gendron et al 2010; Geser et al 2010; Mackenzie et al 2010).

ALS is a neurodegenerative disease, characterised by progressive paralysis and muscle wasting, consequent on the degeneration of both upper and lower motor neurones in the primary motor cortex, brainstem and spinal cord. It is sometimes referred to as motor neuron disease (MND) but there are diseases other than ALS which affect either either upper or lower motor neurons. A definite diagnosis requires both upper and lower motor neurone signs in the bulbar, arm and leg musculature with clear evidence of clinical progression that cannot be explained by any other disease process (Vijesekera and Leigh 2009).

Although the majority of cases are ALS-TDP, there are other cases where the pathological protein differs from TDP-43. Misfolded SOD1 is the pathological protein in ubiquitin-positive inclusions in ALS with SOD1 mutations (Seetharaman et al 2009) and in a very small subset (approximately 3-4%) of familial ALS, due to mutations in FUS (fused in sarcoma protein), the ubiquitinated pathological protein is FUS (Vance et al 2009; Blair et al 2010). FUS, like TDP-43, appears to be important in nuclear-cytoplasmic shuttling although the ways in which impaired nuclear import of FUS remains unclear. A new molecular classification of ALS, adapted from Mackenzie et al (2010), reflects the distinct underlying pathological mechanisms in the different subtypes (see Table below).

New Molecular Classification of ALS (modified from Mackenzie et al 2010). In the majority of cases, TDP-43 is the pathological ubiquitinated protein found in ALS.

| Ubiquitin-positive inclusions in ALS | | | |
|---|---|---|---|
| | Ubiquitinated disease protein | | |
| | TDP-43 | FUS | SOD1 |
| Clinico-pathologic subtype | ALS-TDP | ALS-FUS | ALS-SOD1 |
| Associated genotype | TARDBP | FUS | SOD1 |
| Frequency of ALS cases | Common | Rare | Rare |

Amyotrophic lateral sclerosis has been recognised as a nosological entity for almost a century and a half and it is recognised in ICD-10 is classified as a subtype of MND in ICD 10 (G12.2). Reliable clinical diagnostic are available for ALS, which differ little from Charcot's original description, and neuropathological criteria, reflecting the underlying molecular pathology, have also been agreed.

While ALS is classified pathologically into three subgroups, ALS-TDP, ALS-SOD1 and ALS-FUS, both latter conditions are rare. The largest study to date showed all sporadic ALS cases to have TDP-43 pathology (Mackenzie et al 2007). Only around 5% of ALS is familial (Byme et al 2010) and mutations in SOD1, the commonest mutations found in FALS, account for between 12-23% of cases (Andersen et al 2006). SOD1 may also be implicated in 2-7% of SALS. Mutations in FUS appear to be far less common, accounting for only around 3-4% of FALS (Blair et al 2010). So it can be reliably predicted that a clinical case of SALS will have TDP-43 based pathology. Similarly this can be reliably predicted in FALS due to mutations in TDP-43, which account for around 4% of cases (Mackenzie et al 2010). ALS with mutations in: VCP, accounting for 1-2% of FALS (Johnson et al 2010), ANG (Seilhean et al 2009), and CHMP2B (Cox et al 2010) have also been reported to be associated with TDP-43 positive pathology. Although SOD1. FUS and ATXN2 mutations have not been found to be associated with TDP-43 positive aggregates, it has however been reported that TDP-43 is implicated in the pathological processes putatively arising from these mutations (Higashi et al 2010; Ling et al 2010; Elden et al 2010).

It is therefore established that TDP-43 has an important, and potentially central role, in the pathogenesis of the vast majority of SALS cases and may be implicated in the pathogenesis of a significant proportion of FALS. ALS is now widely considered to be a TDP-43 proteinopathy (Neumann et al 2009) and numerous in vitro, and in vivo studies provide support to the hypothesis that toxic gain of function, due to TDP-43 aggregation is responsible for at least some of the neurotoxicity in the disease.

FTLD syndromes are insidious onset, inexorably progressive, neurodegenerative conditions, with peak onset in late middle age. There is often a positive family history of similar disorders in a first degree relative.

Behavioural variant FTD is characterised by early prominent change in social and interpersonal function, often accompanied by repetitive behaviours and changes in eating pattern. In semantic dementia there are prominent word finding problems, despite otherwise fluent speech, with degraded object knowledge and impaired single word comprehension on cognitive assessment. Progressive non-fluent aphasia presents with a combination of motor speech problems and grammatical deficits. The core clinical diagnostic features for these three FTLD syndromes are shown in the Table below and the full criteria in Neary et al (1998).

Clinical Profile and Core Diagnostic Features of FTLD Syndromes

| FTLD Syndrome -Clinical Profile | Core Diagnostic Features |
|---|---|
| Frontotemporal Dementia Character change and disordered social conduct are the dominant features initially and throughout the disease course. Instrumental functions of perception, spatial skills, praxis and memory are intact or relatively well preserved. | 1. Insidious onset and gradual progression 2. Early decline in social interpersonal conduct 3. Early impairment in regulation of personal conduct 4. Early emotional blunting 5. Early loss of insight |
| Semantic Dementia Semantic disorder (impaired understanding of word meaning and/or object identity) is the dominant feature initially and throughout the disease course. Other aspects of cognition, including autobiographic memory, are intact or relatively well preserved. | A) Insidious onset and gradual progression B) Language disorder characterised by 1. Progressive, fluent empty speech 2. Loss of word meaning manifest by impaired naming and comprehension 3. Semantic paraphasias and/or 4. Perceptual disorder characterised by 1. Prosopagnosia: impaired recognition of identity of familiar faces and/or 2. Associative agnosia: impaired recognition of object identity C) Preserved perceptual matching and drawing reproduction D) Preserved single word repetition E) Preserved ability to read aloud and write to dictation orthographically regular words |

-continued

| FTLD Syndrome -Clinical Profile | Core Diagnostic Features |
|---|---|
| Progressive Non-fluent Aphasia Disorder of expressive language is the dominant feature initially and throughout the disease course. Other aspects of cognition are intact or relatively well preserved. | A) Insidious onset and gradual progression B) Non-fluent spontaneous speech with at least one of the following: agrammatism, phonemic paraphasias or anomia |

The discovery that TDP-43-positive inclusions characterize ALS and FTLD-TDP (Neumann et at 2006) was quickly followed by the identification of missense mutations in the TARDBP gene in both familial and sporadic cases of ALS (Gitcho et al 2008; Sreedharan et al., 2008). So far, 38 different TARDBP mutations have been reported in 79 genealogically unrelated families worldwide (Mackenzie et al 2010). TARDBP mutations account for approximately 4% of all familial and around 1.5% of sporadic ALS cases.

As of December 2010, mutations in thirteen genes which are associated with familial and sporadic ALS have been identified. Linkage of ALS to five other chromosome loci has been demonstrated but thus far specific mutations have not been identified.

TDP-43 Proteinopathies

MT has a mode of action which targets and can reduce TDP-43 protein aggregation in cells, which is a pathological feature of the vast majority of both familial and sporadic ALS and is also characteristic of FTLD-P.

In addition laboratory data shows that methylthioninium inhibits the formation of TDP-43 aggregates in SH-SY5Y cells. Following treatment with 0.05 µM MT, the number of TDP-43 aggregates was reduced by 50%. These findings were confirmed by immunoblot analysis (Yamashita et al 2009).

The compounds and compositions of the invention may therefore be useful for the treatment of amyotrophic lateral sclerosis (ALS) and frontotemporal lobar degeneration (FTLD).

Huntington's Disease and Polyglutamine Disorders MT can reduce polyglutamine protein aggregation in cells, which is a pathological feature of Huntington's disease. Huntington's disease is caused by expansion of a translated CAG repeat located in the N-terminus of huntingtin. Wild-type chromosomes contain 6-34 repeats whereas, in Huntington's disease, chromosomes contain 36-121 repeats. The age of onset of disease correlates inversely with the length of the CAG tracts that code for polyglutamine repeats within the protein.

Laboratory data shows that methylthioninium inhibits the formation of aggregates of a huntingtin derivative containing a polyglutamine stretch of 102 residues in zebrafish (van Bebber et al. 2010). MT, when tested at 0, 10 and 100 µM, prevented the formation of such aggregates in zebrafish in a dose dependent manner.

The compounds and compositions of the invention may therefore be useful for the treatment of Huntington's disease and other polyglutamine disorders such as spinal bulbar muscular atrophy (or Kennedy disease), and dentatorubropallidoluysian atrophy and various spinocerebellar ataxias (Orr & Zoghbi, 2007).

Mitochondrial Diseases and Lafora Disease

The organ most frequently affected in mitochondrial disorders, particularly respiratory chain diseases (RCDs), in addition to the skeletal muscle, is the central nervous system (CNS). CNS manifestations of RCDs comprise stroke-like episodes, epilepsy, migraine, ataxia, spasticity, movement disorders, psychiatric disorders, cognitive decline, or even dementia (mitochondrial dementia). So far mitochondrial dementia has been reported in MELAS, MERRF, LHON, CPEO, KSS, MNGIE, NARP, Leigh syndrome, and Alpers-Huttenlocher disease (Finsterer, 2009). There are four complexes in the mitochondrial respiration chain, invoMng a series of electron transfers. Abnormal function of any of these complexes can result in mitochondrial diseases secondary to an abnormal electron transport chain and subsequent abnormal mitochondrial respiration. Complex Ill of the mitochondrial respiration chain acts to transfer electrons to cytochrome c.

Compounds and compositions of the invention may also be used to treat mitochondrial diseases which are associated with a deficient and/or impaired complex Ill function of the respiration chain. The compounds have the ability to act as effective electron carrier and/or transfer, as the thioninium moiety has a low redox potential converting between the oxidised and reduced form. In the event of an impaired and/or deficient function of Complex III leading to mitochondrial diseases, compounds of the invention are also able to perform the electron transportation and transfer role of complex Ill because of the ability of the thioninium moiety to shuttle between the oxidised and reduced form, thus acting as an electron carrier in place of sub-optimally functioning complex Ill, transferring electrons to cytochrome c.

Compounds and compositions of the invention also have the ability to generate an active thioninium moiety that has the ability to divert misfolded protein/amino acid monomers/oligomers away from the Hsp70 ADP-associated protein accumulation and/or refolding pathways, and instead rechannel these abnormal folded protein monomers/oligomers to the pathway that leads directly to the Hsp70 ATP-dependent ubiquitin-proteasome system (UPS), a pathway which removes these misfolded proteins/amino acid monomers/oligomers via the direct route (Jinwal et al. 2009).

Lafora disease (LD) is an autosomal recessive teenage-onset fatal epilepsy associated with a gradual accumulation of poorly branched and insoluble glycogen, termed polyglucosan, in many tissues. In the brain, polyglucosan bodies, or Lafora bodies, form in neurons. Inhibition of Hsp70 ATPase by MT (Jinwal et al. 2009) may upregulate the removal of misfolded proteins. Lafora disease is primarily due to a lysosomal ubiquitin-proteasomal system (UPS) defect because of a mutation in either the Laforin or Malin genes, both located on Chromosome 6, which result in inclusions that may accelerate the aggregation of misfolded tau protein. Secondary mitochondrial damage from the impaired UPS may further result in a suppressed mitochondrial activity and impaired electron transport chain leading to further lipofuscin and initiating the seizures that are characteristic of Lafora disease.

The MT moiety may disaggregate existing tau aggregates, reduce more tau accumulating and enhance lysosomal efficiency by inhibiting Hsp70 ATPase. MT may lead to a reduction in tau tangles by enhancing the ubiquitin proteasomal system removal of tau monomers/oligomers, through its inhibitory action on Hsp70 ATPase.

Thus compounds and compositions of the present invention may have utility in the treatment of Lafora disease.

Mixtures of Oxidised and Reduced MT Compounds

MT compounds for use in the present invention may include mixtures of the oxidised and reduced form.

In particular, the LMT-containing compounds may include oxidised (MT$^+$) compounds as 'impurities' during synthesis, and may also oxidize (e.g., autoxidize) after synthesis to give the corresponding oxidized forms. Thus, it is likely, if not inevitable, that compositions comprising the compounds of the present invention will contain, as an impurity, at least some of the corresponding oxidized compound. For example an "LMT" salt may include 10 to 15% of MT$^+$ salt.

When using mixed MT compounds the MT dose can be readily calculated using the molecular weight factors of the compounds present.

Salts and Solvates

Although the MT containing compounds described herein are themselves salts, they may also be provided in the form of a mixed salt (i.e., the compound of the invention in combination with another salt). Such mixed salts are intended to be encompassed by the term "and pharmaceutically acceptable salts thereof". Unless otherwise specified, a reference to a particular compound also includes salts thereof.

The compounds of the invention may also be provided in the form of a solvate or hydrate. The term 'solvate' is used herein in the conventional sense to refer to a complex of solute (e.g., compound, salt of compound) and solvent. If the solvent is water, the solvate may be conveniently referred to as a hydrate, for example, a mono-hydrate, a di-hydrate, a tri-hydrate, a penta-hydrate etc. Unless otherwise specified, any reference to a compound also includes solvate and any hydrate forms thereof.

Naturally, solvates or hydrates of salts of the compounds are also encompassed by the present invention.

A number of patents and publications are cited herein in order to more fully describe and disclose the invention and the state of the art to which the invention pertains. Each of these references is incorporated herein by reference in its entirety into the present disclosure, to the same extent as if each individual reference was specifically and individually indicated to be incorporated by reference.

Throughout this specification, including the claims which follow, unless the context requires otherwise, the word "comprise." and variations such as "comprises" and "comprising," will be understood to imply the inclusion of a stated integer or step or group of integers or steps but not the exclusion of any other integer or step or group of integers or steps.

It must be noted that, as used in the specification and the appended claims, the singular forms "a," "an," and "the" include plural referents unless the context clearly dictates otherwise. Thus, for example, reference to "a pharmaceutical carrier" includes mixtures of two or more such carriers, and the like.

Ranges are often expressed herein as from "about" one particular value, and/or to "about" another particular value. When such a range is expressed, another embodiment includes from the one particular value and/or to the other particular value. Similarly, when values are expressed as approximations, by the use of the antecedent "about," it will be understood that the particular value forms another embodiment.

Any sub-titles herein are included for convenience only, and are not to be construed as limiting the disclosure in any way.

The invention will now be further described with reference to the following non-limiting Figures and Examples. Other embodiments of the invention will occur to those skilled in the art in the light of these.

The disclosure of all references cited herein, inasmuch as it may be used by those skilled in the art to carry out the invention, is hereby specifically incorporated herein by cross-reference.

FIGURES

FIG. 1. (A) Screening, safety and efficacy populations. (B) Patient categorisation by randomised treatment, AD-approved co-medication status and withdrawal rates at 65 weeks.

Figure 2:
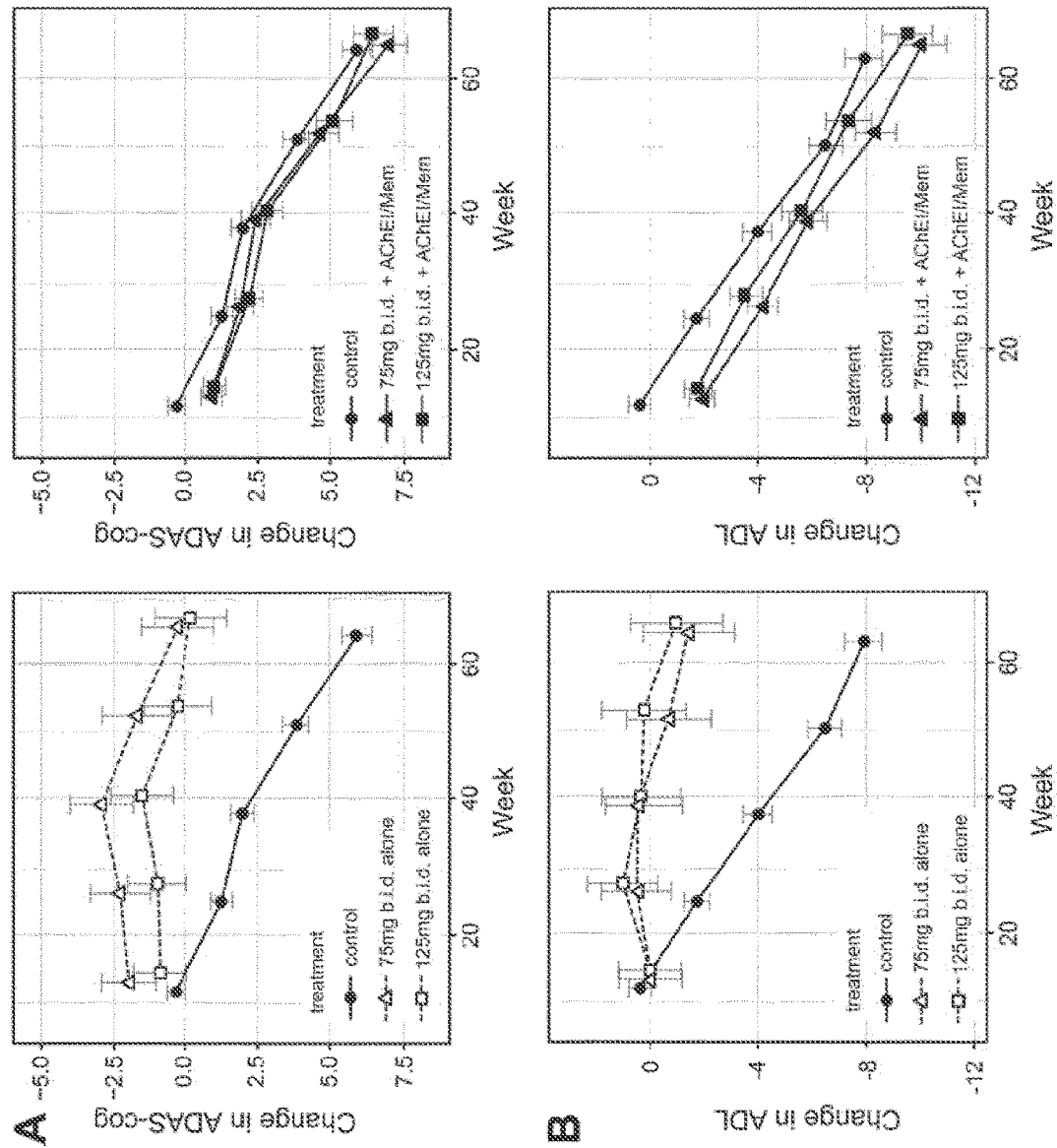

FIG. 2. Least squares estimates of change from baseline in (A) ADAS-cog and (B) ADCS-ADL using prespecified repeat of primary analysis with stratification factor AChEI/Mem as an interaction term in the model.

Figure 3:
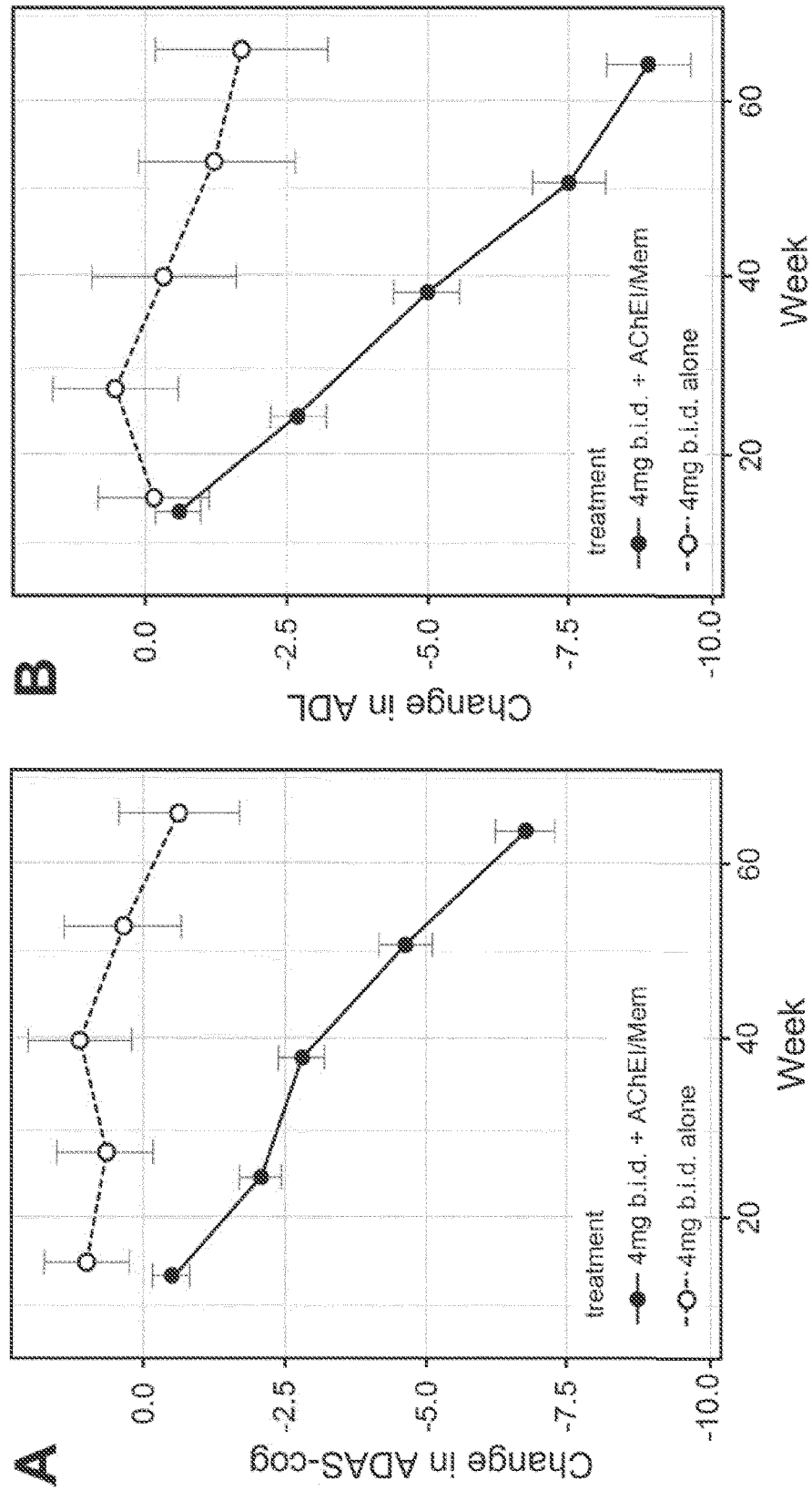

FIG. 3. Least squares estimates of change from baseline for (A) ADAS-cog and (B) ADCS-ADL in patients restricted to those randomised to the control arm and receiving 4 mg b.i.d. of LMTM, either alone or in combination with AD-labelled medications.

Figure 4:
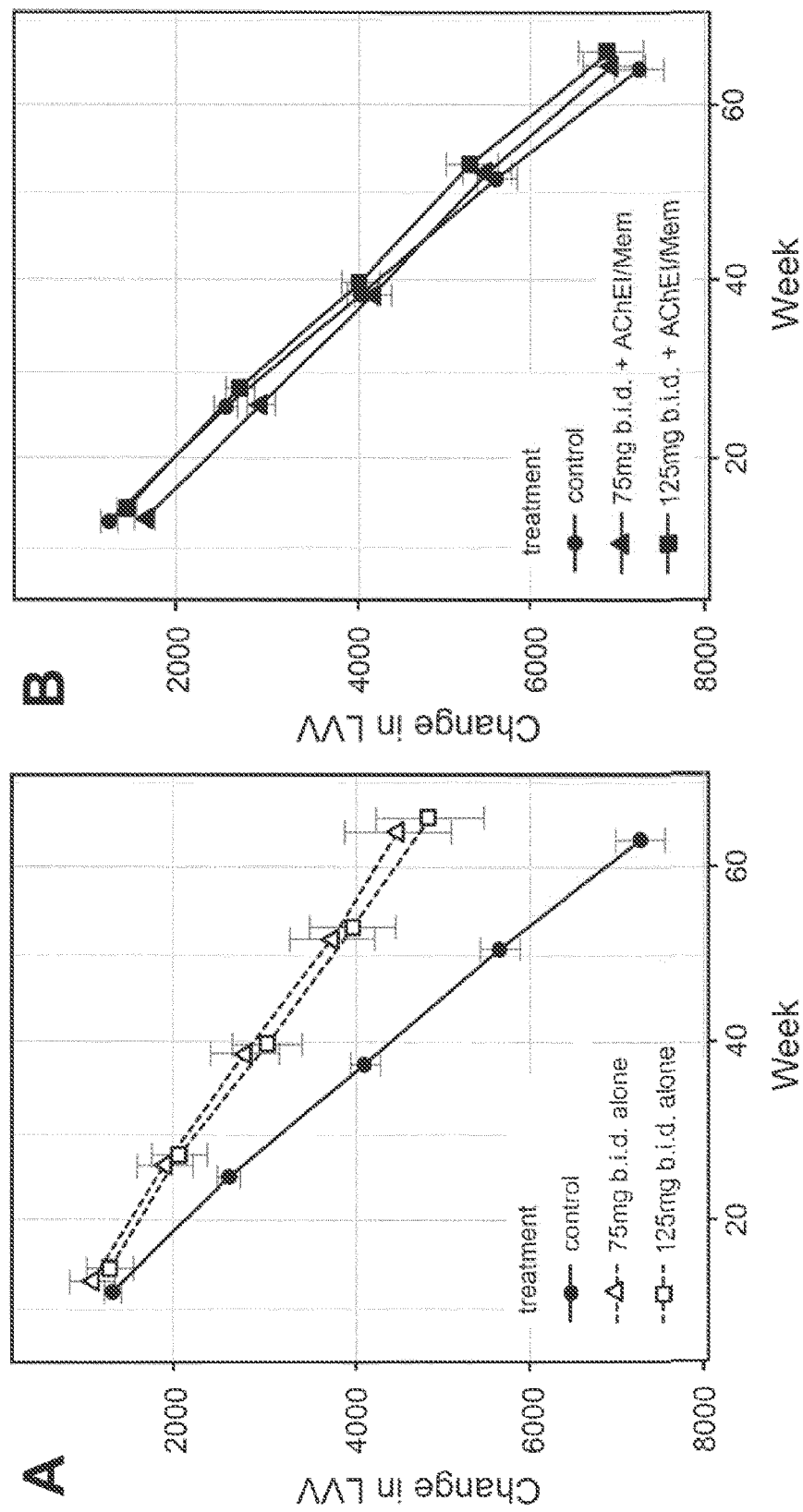

FIG. 4. Least squares estimates of LVV change overtime using prespecified repeat of primary analysis with stratification co-variate AChEI/Mem as an interaction term in the model.

Figure 5:
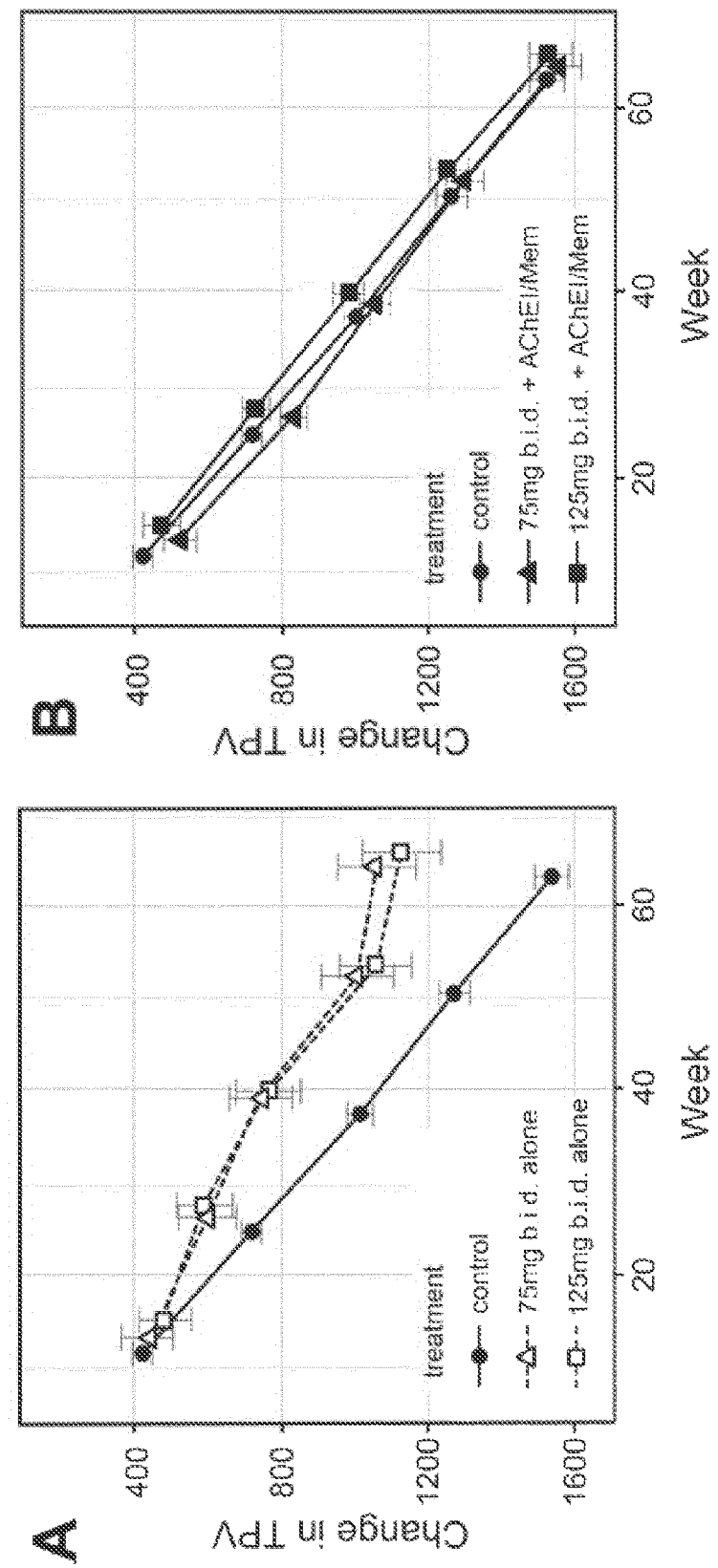

FIG. 5. Least squares estimates of TPV change from baseline using prespecified repeat of primary analysis with stratification factor AChEI/Mem as an interaction term in the model.

Figure 6:
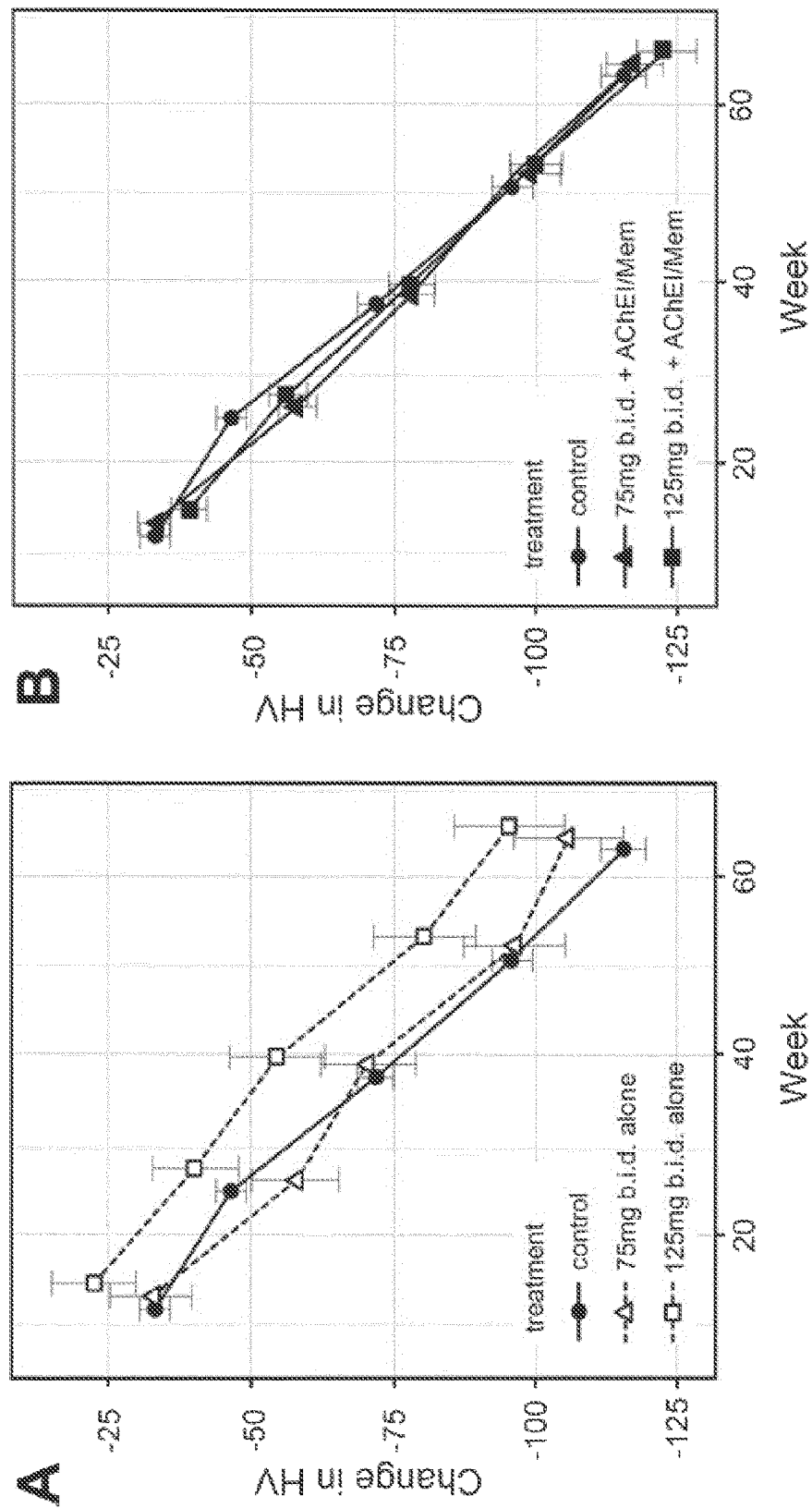

FIG. 6. Least squares estimates of HV change from baseline using prespecified repeat of primary analysis with stratification factor AChEI/Mem as an interaction term in the model.

Figure 7:
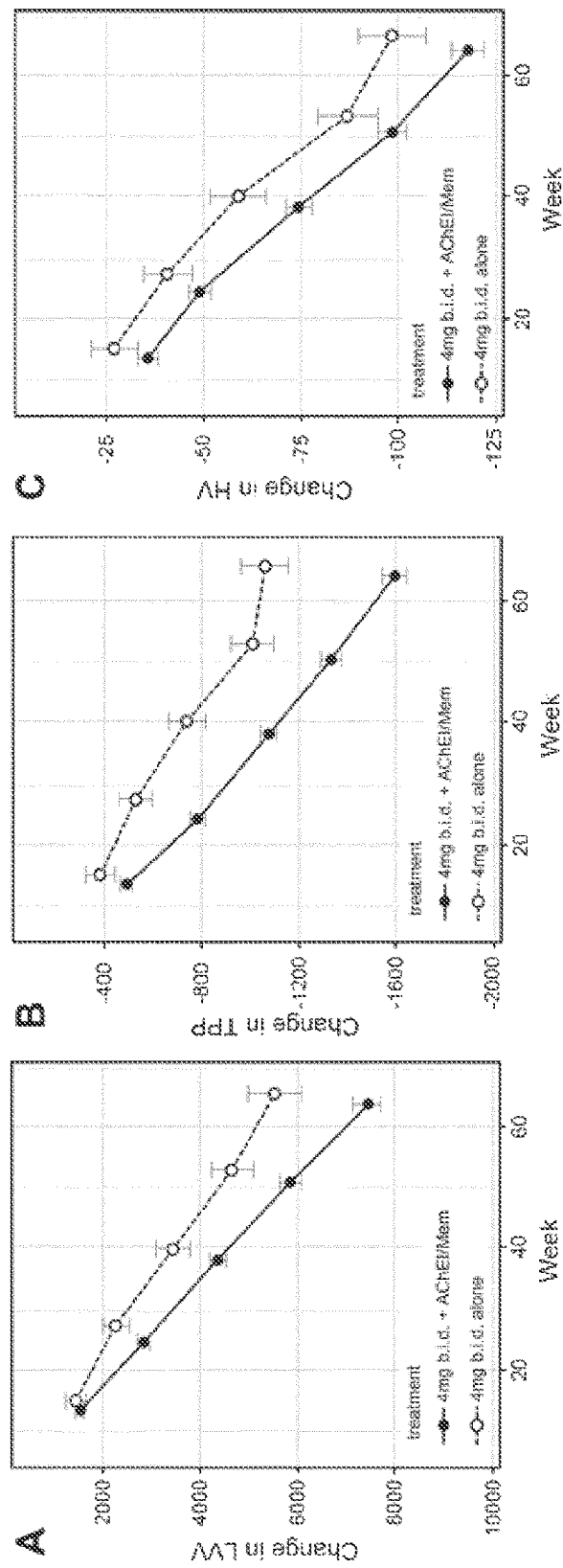

FIG. 7. Least squares estimates of responses for change from baseline in (A) LVV, (B) TPV and (C) HV in subjects restricted to those randomised to the control arm and receiving 4 mg b.i.d. of LMTM either alone or in combination with AD-labelled medications.

EXAMPLES

Example 1—Provision of MT-Containing Compounds

Methods for the chemical synthesis of the MT-containing compounds described herein are known in the art. For example:

Synthesis of compounds 1 to 7 can be performed according to the methods described in WO2012/107706, or methods analogous to those.

Synthesis of compound 8 can be performed according to the methods described in WO2007/110627, or a method analogous to those.

Synthesis of compound 9 (MTC) is well known in the art. Examples syntheses of highly pure MTC are provided in WO2006/032879 and WO2008/007074.

Synthesis of compounds 10 to 13 can be performed according to the methods described in WO2007/110630, or methods analogous to those.

Example 2—Formulation of MT-Containing Compounds

Methods for the chemical synthesis of the MT-containing compounds described herein are known in the art. Example methods using dry compression, for example, are provided in WO2012/072977.

Example 3—Phase 3 Clinical Trial in Mild to Moderate AD

Methods

Outcomes and Measures

The co-primary efficacy outcomes were change from baseline in 11-item Alzheimer's Disease Assessment Scale—cognitive subscale (ADAS-cog) and the 23-item Alzheimer's Disease Cooperative Study Activities of Daily Living (ADCS-ADL). Magnetic resonance imaging (MRI) volumetry was chosen as the principal secondary outcome to support a potential effect on the rate of brain atrophy (Fox et al., 1997; Ridha et al., 2008). Change in Lateral Ventricular Volume (LVV), as measured by the Ventricular Boundary Shift Integral (VBSI), (Salloway et al., 2014) was chosen as the principal measure as it provides high-contrast boundaries for measurement and is less affected by motion artefacts than whole brain or smaller structures. Key supportive topographical measures (temporo-parietal (TPV) and hippocampal volume (HV)) are also reported.

Patients

Patients were recruited at 115 sites across 16 countries between January 2013 and August 2014. Enrolment of approximately 833 patients was targeted, with 891 patients actually recruited, in order to obtain data on approximately 500 patients completing the study, assuming a 30-40% drop-out rate. Patients aged <90 meeting a diagnosis of all cause dementia and probable AD according to National Institute of Aging (NIA) and Alzheimer's Association (AA) criteria were included if they had a Clinical Dementia Rating (CDR) total score of 1 or 2 and Mini-Mental State Examination (MMSE) score of 14-26 inclusive. Adult caregiver(s) were required to participate. Concomitant use of AChEIs and/or memantine was permitted, provided the patient had been taking the medication(s) for 23 months, with no changes to the dosage for 26 weeks prior to screening. Concomitant use of serotonergic antidepressant medication was permitted, but patients were monitored closely using a targeted rating scale derived from 4 published diagnostic criteria (Alusik et al., 2014) due to a theoretical potential for serotonin syndrome (Ramsay et al., 2007). Patients were excluded from the study if they had a significant central nervous system disorder other than AD or significant focal or vascular intracranial pathology on brain magnetic resonance imaging (MRI) performed within 6 weeks prior to baseline. Because $MT^+$ in high doses can induce methaemoglobinaemia, subjects with glucose-6-phosphate dehydrogenase deficiency or who were otherwise at haematological risk were excluded. Other inclusion/exclusion criteria are provided in the Supplementary Materials.

Randomisadon and Masking

Patients were randomised at baseline to LMTM 75 mg b.i.d. or 125 mg b.i.d. (expressed as MT base equivalent) or control in a 3:3:4 ratio. The randomisation was stratified according to geographical region (3 levels: North America, Europe, rest of world), use of AD-labelled co-medications (2 levels, using or not using) and severity (2 levels, moderate MMSE 14-19 inclusive, mild MMSE 20-26 inclusive). Patients in the control arm received a dose of 4 mg b.i.d. to maintain blinding.

Ethical Conduct of the Study

All patients provided written informed consent prior to enrolling in the study; legally acceptable representatives provided consent on behalf of patients with reduced decision-making capacity. Adult caregivers also provided consent for their own involvement. The study was conducted in accordance with the Declaration of Helsinki and the International Conference on Harmonisation Guidelines for Good Clinical Practice, and approval of the study protocol and all related documents was obtained from the appropriate Independent Ethics Committees and Institutional Review Boards for all study sites. An independent Data and Safety Monitoring Board was established for oversight of accruing safety information. The trial is registered at www.clinicaltrials.gov (NCT01689246) and the European Union Clinical Trials Registry (2012-002866-11).

Clinical and Imaging Assessments

ADAS-cog and ADCS-ADL assessments were performed at baseline and every 13 weeks thereafter, with change at 65 weeks (the final on-treatment visit) the primary efficacy measures. These were repeated at the final off-treatment follow-up visit at Week 69. Secondary efficacy measures included Clinical Global Impression of Change (ADCS-CGIC, administered by an independent rater); MMSE, administered on screening and at Weeks 26, 52, 65 and 69. Brain MRI scans were performed at baseline/screening and every 13 weeks using a standardized protocol including volumetric 3D T1-weighted data consistent with ADNI recommendations, FLAIR, T2* Gradient Echo and T2-weighted sequences. Diffusion-Weighted Imaging was also available at screening in order to exclude patients with co-existing pathology that would lead to a diagnosis other than probable AD. Each site was first qualified ensuring standardised acquisition protocol, patient handling and data management. MRI data were centrally collected by Imaging Corelab (Bioclinica). Data were centrally reviewed by RadMD for eligibility and safety (Amyloid Related Imaging Abnormalities, or ARIA monitoring) on an on-going basis. Volumetric 3DT1 data were also reviewed centrally in order to measure (using a boundary shift integral (BSI) technique; Salloway et al., 2014) change in LVV as principal secondary outcome measure, and as exploratory endpoints temporo-parietal volume (TPV), whole brain volume (WBV) and hippocampal volume (HV, estimated as the mean of left and right) (Wischik et al., 2016). Additional exploratory endpoints included change in glucose uptake in the temporal lobe, assessed using $^{18}$F-fluorodeoxyglucose positron emission tomography (FDG-PET) performed during screening and at Weeks 39 and 65 in a subset of patients in sites with this imaging capability. Changes in cerebrospinal fluid biomarkers of Alzheimer's disease, including total tau, phospho-tau and amyloid-$\beta_{1\text{-}42}$, were explored using cerebrospinal fluid samples that were collected at baseline and Week 65 (or early termination visit). Lumbar punctures were performed only in subjects who were themselves able to provide consent specifically for this procedure.

Patients were monitored throughout for adverse events (AEs) and clinical laboratory testing, physical and neurological examinations and 12-lead electrocardiograms were performed at all clinic visits (screening, baseline and Weeks 2, 6, 13, 26, 39, 52, 65 and 69). Patients were also assessed at all visits for suicidal ideation and intent, and were systematically assessed for signs of serotonin toxicity.

Statistical Methods

The primary efficacy analyses of change from baseline in ADAS-cog and ADCS-ADL scores were conducted in the modified intent-to-treat (mITT) population (all randomised patients who took at least one dose of study treatment and had at least one post-baseline, on-treatment efficacy assessment). The primary analysis was specified as a mixed model repeated-measures (MMRM) analysis with an unstructured covariance matrix and no imputation for missing data. The model included categorical visit (5 levels corresponding to assessments at weeks 13, 26, 39, 52 and 65), treatment (3 levels corresponding to control, 75 mg b.i.d. and 125 mg b.i.d.), treatment-by-visit interaction, and the stratification variables as additive terms, and baseline ADAS-cog or ADCS-ADL as a covariate. A similar exploratory analysis was specified in the Statistical Analysis Plan (SAP) with the AChEI/Mem covariate as an interaction term with treatment and as an interaction term with visit. Westfall's method for multiple comparison correction was used in each step to ensure strong control of the familywise error with alpha 0.05 (Westfall et al., 1997) The same analyses were implemented for change in LW, WBV, TPV, HV and TPV.

Results

Patients

The patient disposition and trial design is shown in FIG. 1. Of 891 patients randomised, 885 received at least one dose of study drug and comprised the safety population, and 855 patients were in the mITT population FIG. 1(A). Patient disposition by randomised treatment and treatment with or without AChEI/Mem is shown in FIG. 1(B). The baseline demographics and clinical characteristics of the safety population are shown in Table 1. There were 618 patients completing the study to 65 weeks (with 579 remaining on treatment), an overall study withdrawal rate of 31%. MRI scans from all scheduled visits were available from 880 patients pre-treatment and 554 at 65 weeks. FDG-PET data were available from 101 patients at 65 weeks, of whom only 6 were not taking AChEI/Mem treatments.

TABLE 1

Patient baseline demographics and clinical characteristics (safety population)

| Characteristic | Control LMTM 4 mg b.i.d. n = 354 | LMTM 75 mg b.i.d. n = 267 | LMTM 125 mg b.i.d. n = 264 | Total n = 885 |
|---|---|---|---|---|
| Age (years) | | | | |
| Mean (SD) | 70.7 (8.5) | 71.0 (9.3) | 70.1 (9.3) | 70.6 (9.0) |
| Median (min; max) | 72.0 (40; 89) | 72.0 (39; 88) | 71.0 (32; 89) | 72.0 (32; 89) |
| Sex | | | | |
| Male, n (%) | 134 (38) | 93 (35) | 113 (43) | 340 (38) |
| Female, n (%) | 220 (62) | 174 (65) | 151 (57) | 545 (62) |
| Race | | | | |
| American Indian or Alaska Native, n (%) | 2 (0.6) | 3 (1.1) | 2 (0.8) | 7 (0.8) |
| Asian, n (%) | 41 (11.6) | 32 (12.0) | 30 (11.4) | 103 (11.6) |
| Black or African American, n (%) | 3 (0.8) | 3 (1.1) | 4 (1.5) | 10 (1.1) |
| White, n (%) | 307 (86.7) | 226 (84.6) | 225 (85.2) | 758 (85.6) |
| Other, n (%) | 1 (0.3) | 0 | 2 (0.8) | 3 (0.3) |
| Multiple Race, n (%) | 0 | 3 (1.1) | 1 (0.4) | 4 (0.5) |
| Years since diagnosis | | | | |
| Mean (SD) | 2.8 (2.4) | 2.9 (2.3) | 2.8 (2.2) | 2.8 (2.3) |
| Dementia severity | | | | |
| CDR 0.5, n (%) | 4 (1.1) | 1 (0.4) | 2 (0.8) | 7 (0.8) |
| CDR 1, n (%) | 261 (73.7) | 209 (78.3) | 192 (72.7) | 662 (74.8) |
| CDR 2, n (%) | 89 (25.1) | 57 (21.3) | 70 (26.5) | 216 (24.4) |
| MMSE | | | | |
| Mean (SD) | 18.6 (3.45) | 18.8 (3.44) | 18.5 (3.40) | 18.6 (3.43) |
| Median (min; max) | 18.0 (14; 26) | 19.0 (14; 26) | 18.0 (14; 26) | 18.0 (14; 26) |
| MMSE severity | | | | |
| MMSE ≥20, n (%) | 134 (38) | 105 (39) | 98 (37) | 337 (38) |
| MMSE <20, n (%) | 220 (62) | 162 (61) | 166 (63) | 548 (62) |
| ADAS-Cog: | | | | |
| Mean (SD) | 27.2 (10.1) | 26.5 (9.4) | 26.7 (9.7) | 26.9 (9.8) |
| Median (min; max) | 26.3 (7; 57) | 26.3 (8; 54) | 26.3 (8; 56) | 26.3 (7; 57) |
| ADCS-ADL: | | | | |
| Mean (SD) | 55.9 (12.7) | 58.0 (11.1) | 57.5 (12.7) | 57.0 (12.3) |
| Median (min; max) | 58.0 (17; 78) | 58.5 (16; 78) | 60.0 (13; 78) | 59.0 (13; 78) |
| Whole brain volume (cm$^3$) | | | | |
| Mean (SD) | 927 (108) | 922 (115) | 939 (101) | 929 (108) |
| Median (min; max) | 917 (681; 1,233) | 922 (602; 1,207) | 934 (682; 1,264) | 925 (602; 1,264) |

TABLE 1-continued

Patient baseline demographics and clinical characteristics (safety population)

| Characteristic | Control LMTM 4 mg b.i.d. n = 354 | LMTM 75 mg b.i.d. n = 267 | LMTM 125 mg b.i.d. n = 264 | Total n = 885 |
|---|---|---|---|---|
| Lateral ventricular volume ($cm^3$) | | | | |
| Mean (SD) | 52 (23) | 52 (26) | 51 (23) | 52 (24) |
| Median (min; max) | 49 (15; 154) | 44 (12; 160) | 47 (15; 138) | 47 (12; 160) |
| Hippocampal volume ($mm^3$) | | | | |
| Mean (SD) | 2.3 (0.6) | 2.7 (0.6) | 2.9 (0.6) | 2.8 (0.6) |
| Median (min; max) | 2.7 (1.4; 4.5) | 2.7 (1.4; 4.4) | 2.8 (1.5; 5.0) | 2.7 (1.4; 5.0) |
| AD-approved co-medications | | | | |
| AChEI only, n (%) | 183 (52) | 151 (57) | 150 (57) | 484 (55) |
| Memantine only, n (%) | 32 (9) | 16 (6) | 15 (6) | 63 (7) |
| AChEI and memantine, n (%) | 93 (26) | 60 (23) | 61 (23) | 214 (24) |
| CSF biomarkers (ng/L) | | | | |
| Total tau, mean (SD) [n] | 143.9 (68.4) [19] | 156.4 (72.5) [15] | 113.2 (54.7) [5] | 144.8 (68.2) [39] |
| Phospho-tau, mean (SD) [n] | 59.2 (25.3) [20] | 61.2 (20.3) [15] | 58.1 (12.8) [5] | 59.8 (21.9) [40] |
| Aβ1-42, mean (SD) [n] | 264.7 (96.6) [20] | 276.0 (85.9) [15] | 235.8 (62.1) [5] | 265.3 (88.0) [40] |
| APOE genotype | | | | |
| ε4 allele present, n (%) | 144 (47.5) | 91 (41.9) | 114 (52.5) | 349 (47.4) |
| ε4 allele absent, n (%) | 159 (52.5) | 126 (58.1) | 103 (47.5) | 388 (52.6) |

Efficacy Analyses of Primary Clinical Outcomes

Table 2 reports change in ADAS-cog and ADCS-ADL scores, decline in the control arm and difference with respect to control by treatment arm. The ADAS-cog decline at 12 months (3.85±0.47, mean±se) was indistinguishable from a meta-analysis of recent studies (4.58, 95% Cl: 3.69-5.47) at 12 months (Salloway et al., 2014; Doody et al., 2014). Likewise, the ADCS-ADL decline at 12 months (−6.51±0.63) was similar to that of the only available recent study (Doody et al., 2014) in mild/moderate AD (−5.79, 95% Cl: −7.10-−4.48).

As can be seen from Table 2, neither of the primary analyses yielded significant effects for either 75 mg b.i.d. or for 125 mg b.i.d. at 65 weeks. However, the AChEI/Mem factor was significant for both ADAS-cog and ADCS-ADL, with p-values 9.4e-05 and 0.0174 respectively after correction for multiple comparisons. This implies a mean additive treatment benefit in patients not taking AD treatments of −2.30 (95% Cl: −3.35-−1.25) ADAS-cog units and 2.00 (95% Cl: 0.65-3.35) ADCS-ADL units. Likewise, mild subjects had lower rates of progression for both ADAS-cog and ADCS-ADL overall (p values: 8.6e-04 and 9.6e-07, respectively). There was no overall effect of region on either outcome.

TABLE 2

Primary efficacy analyses for ADAS-cog (A) and ADCS-ADL (B) at 65 weeks. In this and in all following tables, "pval-adj" signifies the p values corrected for multiple comparisons using the Westfall procedure. All stratification covariates are additive terms.

| | Estimate | SE | 2.50% | 97.50% | p value | pval-adj |
|---|---|---|---|---|---|---|
| ADAS-cog | | | | | | |
| Control | 6.32 | 0.52 | 5.31 | 7.34 | | |
| 75 mg b.i.d. | −0.02 | 0.80 | −1.60 | 1.56 | 0.983 | 0.983 |
| 125 mg b.i.d. | −0.43 | 0.83 | −2.06 | 1.20 | 0.602 | 0.932 |
| Not using AChEI/Mem | −2.30 | 0.53 | −3.35 | −1.25 | 1.78e-05 | 9.4e-05 |
| Mild | −1.03 | 0.28 | −1.57 | −0.59 | 1.85e-04 | 8.6e-04 |
| North America | −0.08 | 0.26 | −0.58 | 0.43 | 0.769 | 0.947 |
| Rest of world | −0.47 | 0.44 | −1.32 | 0.39 | 0.285 | 0.724 |
| ADCS-ADL | | | | | | |
| Control | −8.22 | 0.72 | −9.63 | −6.82 | | |
| 75 mg b.i.d. | −0.93 | 1.12 | −3.12 | 1.26 | 0.407 | 0.866 |
| 125 mg b.i.d. | −0.34 | 1.16 | −2.61 | 1.93 | 0.770 | 0.948 |
| Not using AChEI/Mem | 2.00 | 0.69 | 0.65 | 3.35 | 0.00365 | 0.0174 |
| Mild | 1.62 | 0.31 | 1.02 | 2.23 | 2.0e-07 | 9.6e-07 |
| North America | 0.08 | 0.34 | −0.58 | 0.74 | 0.814 | 0.948 |
| Rest of world | −0.27 | 0.56 | −1.37 | 0.83 | 0.632 | 0.948 |

In order to understand better the role of the AChEI/Mem factor, a pre-specified analysis was undertaken which included this as an interaction term with visit and as an interaction term with LMTM treatment in the model rather than only as an overall additive term as in the primary model. The results by dose-arm and AChEI/Mem status are shown in Table 3 and FIG. 2 for both ADAS-cog and ADCS-ADL.

TABLE 3

Prespecified repeat of primary analysis of ADAS-cog and ADCS-ADL with stratification covariate AChEI/Mem as an interaction term in the model.

|  | Estimate | SE | 2.50% | 97.50% | p value | pval-adj |
|---|---|---|---|---|---|---|
| ADAS-cog |  |  |  |  |  |  |
| Control | 5.98 | 0.51 | 5.00 | 6.98 | 0.000 |  |
| 75 mg b.i.d. | −6.25 | 1.36 | −8.92 | −3.59 | 4.15e−06 | 1.5e−05 |
| 125 mg b.i.d. | −5.79 | 1.37 | −8.47 | −3.11 | 2.35e−05 | 6.8e−05 |
| 75 mg b.i.d. + AChEI/Mem | 1.02 | 0.81 | −0.58 | 2.61 | 0.212 | 0.362 |
| 125 mg bi.d. + AChEI/Mem | 0.50 | 0.84 | −1.15 | 2.14 | 0.555 | 0.555 |
| ADCS-ADL |  |  |  |  |  |  |
| Control | −7.92 | 0.70 | −9.29 | −6.55 | 0.000 |  |
| 75 mg b.i.d. | 6.48 | 1.84 | 2.87 | 10.09 | 4.3e−04 | 0.00138 |
| 125 mg b.i.d. | 6.93 | 1.86 | 3.29 | 10.57 | 1.9e−04 | 0.00711 |
| 75 mg b.i.d. + AChEI/Mem | −2.16 | 1.13 | −4.37 | 0.05 | 0.0553 | 0.103 |
| 125 mg bi.d. + AChEI/Mem | −1.62 | 1.17 | −3.91 | 0.68 | 0.167 | 0.167 |

Given the effect of AD treatments on the efficacy of LMTM given at higher doses, the same effect was explored further in post-hoc analyses restricted to subjects randomised to the control arm receiving 4 mg b.i.d. of LMTM. The results are shown in Table 4 and FIG. 3 for ADAS-cog and ADCS-ADL.

TABLE 4

Post-hoc analysis of ADAS-cog and ADCS-ADL restricted to subjects randomised to the control arm and receiving 4 mg b.i.d. with or without AD-labelled medications.

|  | Estimate | SE | 2.50% | 97.50% | p value |
|---|---|---|---|---|---|
| ADAS-cog |  |  |  |  |  |
| 4 mg b.i.d. + AChEI/Mem | 6.79 | 0.53 | 5.75 | 7.83 |  |
| 4 mg b.i.d. | −5.90 | 1.14 | −8.13 | −3.66 | 2.3e−07 |

TABLE 4-continued

Post-hoc analysis of ADAS-cog and ADCS-ADL restricted to subjects randomised to the control arm and receiving 4 mg b.i.d. with or without AD-labelled medications.

|  | Estimate | SE | 2.50% | 97.50% | p value |
|---|---|---|---|---|---|
| ADCS-ADL |  |  |  |  |  |
| 4 mg b.i.d. + AChEI/Mem | −8.90 | 0.73 | −10.34 | −7.47 |  |
| 4 mg b.i.d. | 7.19 | 1.55 | 4.15 | 10.23 | 3.5e−06 |

MRI Volumetric Analysis of Lateral Ventricular Volume (LW), Temporo-Parietal Volume (TPV) and Hippocampal Volume (HV)

Using the same initial analysis model as for the primary clinical outcomes, no effect of treatment was seen (data not shown). In the prespecified analysis model with the AChEI/Mem factor as an interaction term in the model, results similar to those shown for the clinical outcomes were found for LVV, with p values 4.0e−05 and 3.8e−04, respectively for the 75 mg b.i.d. or 125 mg b.i.d. doses. The results were similar in the TPV analysis, with p values 2.4e−04 and 0.00160 for 75 mg b.i.d. and 125 mg b.i.d. doses respectively. In the HV analysis, only the 125 mg b.i.d. dose taken alone approached nominal significance (p=0.0558) in the mixed mild/moderate population. The data are shown in Table 5 and FIGS. 4, 5 and 6.

TABLE 5

Prespecified repeat of primary analysis of LVV, TPV and HV (mm$^3$) with stratification co-variate AChEI/Mem as an interaction term in the model.

|  | Estimate | SE | 2.50% | 97.50% | p value | pval-adj |
|---|---|---|---|---|---|---|
| LVV |  |  |  |  |  |  |
| Control | 7,187 | 279 | 6,641 | 7,733 |  |  |
| 75 mg b.i.d. | −2,707 | 659 | −3,999 | −1,416 | 4.0e−05 | 1.9e−04 |

TABLE 5-continued

Prespecified repeat of primary analysis of LVV, TPV and HV (mm$^3$) with stratification co-variate AChEI/Mem as an interaction term in the model.

|  | Estimate | SE | 2.50% | 97.50% | p value | pval-adj |
|---|---|---|---|---|---|---|
| 125 mg b.i.d. | −2,347 | 660 | −3,641 | −1,052 | 3.8e−04 | 0.00124 |
| 75 mg b.i.d. + AChEI/Mem | −273 | 443 | −1,141 | 596 | 0.538 | 0.733 |
| 125 mg b.i.d. + AChEI/Mem | −306 | 453 | −1,194 | 583 | 0.500 | 0.733 |
| TPV |  |  |  |  |  |  |
| Control | −1529 | 46 | −1620 | −1438 |  |  |
| 75 mg b.i.d. | 472 | 117 | 244 | 701 | 5.2e−05 | 2.4e−04 |
| 125 mg b.i.d. | 405 | 117 | 176 | 634 | 5.2e−04 | 0.00160 |
| 75 mg b.i.d. + AChEI/Mem | −39 | 74 | −183 | 106 | 0.597 | 0.825 |
| 125 mg b.i.d. + AChEI/Mem | −12 | 75 | −160 | 135 | 0.869 | 0.869 |
| HV |  |  |  |  |  |  |
| Control | −115.3 | 4.0 | −123.1 | −108.5 |  |  |
| 75 mg b.i.d. | 9.5 | 10.4 | −10.8 | 29.8 | 0.360 | 0.571 |
| 125 mg b.i.d. | 20.0 | 10.4 | −0.5 | 40.5 | 0.0558 | 0.187 |
| 75 mg b.i.d. + AChEI/Mem | −2.0 | 6.4 | −14.5 | 10.5 | 0.754 | 0.754 |
| 125 mg b.i.d. + AChEI/Mem | −7.4 | 6.5 | −20.2 | 5.3 | 0.253 | 0.555 |

The effect of AD-labelled co-medications on the LVV, TPV and HV efficacy of low dose LMTM was explored further in the post-hoc analysis restricted to subjects randomised to the control arm receiving LMTM 4 mg b.i.d. either alone or in combination with AChEI/Mem. The results are shown in Table 6 and FIG. 7.

TABLE 6

Post-hoc analysis of LVV, TPV and HV (mm$^3$) restricted to subjects randomized to the control arm and receiving 4 mg b.i.d. of LMTM either alone or in combination with AD-labelled medications.

|  | Estimate | SE | 2.50% | 97.50% | p value |
|---|---|---|---|---|---|
| LVV |  |  |  |  |  |
| 4 mg b.i.d. + AChEI/Mem | 7,426 | 289 | 6860 | 7,993 |  |
| 4 mg b.i.d. | −1,894 | 549 | −2,972 | −818 | 0.000564 |
| TPV |  |  |  |  |  |
| 4 mg b.i.d. + AChEI/Mem | −1,596 | 48 | −1,691 | −1,501 |  |
| 4 mg b.i.d. | 534 | 98 | 342 | 725 | 4.9e−08 |
| HV |  |  |  |  |  |
| 4 mg b.i.d. + AChEI/Mem | −117.8 | 4.1 | −125.9 | −109.7 |  |
| 4 mg b.i.d. | 19.5 | 8.7 | 2.3 | 36.6 | 0.0259 |

Mild and Moderate AD

The same analyses were repeated in mild and moderate subjects separately as disease severity was a highly significant covariate in the primary model (Table 7). The results for treatment with LMTM as monotherapy are shown only for the 75 mg b.i.d. and 125 mg b.i.d. doses compared with the control arm as randomised. The analysis of the 4 mg b.i.d. dose was restricted to subjects randomised to the control arm and receiving 4 mg b.i.d. with or without AChEI/Mem.

TABLE 7

Analyses of ADAS-cog, ADCS-ADL, LVV, TPV and HV in mild AD and moderate AD with stratification covariate AChEI/Mem as an interaction term in the model. Treatment with LMTM alone is compared with the control arm as randomised for the 75 mg b.i.d. and 125 mg b.i.d. doses. The analysis of the 4 mg b.i.d. dose was restricted to subjects randomised to the control arm and taking or not taking AD-labelled co-medications.

|  | Estimate | SE | 2.50% | 97.50% | p value |
|---|---|---|---|---|---|
| ADAS-cog |  |  |  |  |  |
| Mild AD |  |  |  |  |  |
| Control | 2.27 | 0.77 | 0.77 | 3.77 |  |
| 75 mg b.i.d. | −8.89 | 1.76 | −12.37 | −5.41 | 5.5e−07 |

TABLE 7-continued

Analyses of ADAS-cog, ADCS-ADL, LVV, TPV and HV in mild
AD and moderate AD with stratification covariate AChEI/Mem
as an interaction term in the model. Treatment with
LMTM alone is compared with the control arm as randomised
for the 75 mg b.i.d. and 125 mg b.i.d. doses. The analysis
of the 4 mg b.i.d. dose was restricted to subjects
randomised to the control arm and taking or not taking AD-labelled co-medications.

|  | Estimate | SE | 2.50% | 97.50% | p value |
|---|---|---|---|---|---|
| 125 mg b.i.d. | −5.03 | 1.81 | −8.58 | −1.47 | 0.00557 |
| 4 mg b.i.d. + AChEI/Mem | 3.24 | 0.80 | 1.67 | 4.81 |  |
| 4 mg b.i.d. | −6.41 | 1.55 | −9.44 | −3.37 | 3.5e−05 |
| Moderate AD |  |  |  |  |  |
| Control | 7.89 | 0.68 | 6.55 | 9.23 |  |
| 75 mg b.i.d. | −2.01 | 1.94 | −5.81 | 1.80 | 0.301 |
| 125 mg b.i.d. | −5.75 | 1.92 | −9.51 | −1.98 | 0.00277 |
| 4 mg b.i.d. + AChEI/Mem | 8.49 | 0.71 | 7.09 | 9.88 |  |
| 4 mg b.i.d. | −4.74 | 1.58 | −7.83 | −1.65 | 0.00267 |
| ADCS-ADL |  |  |  |  |  |
| Mild AD |  |  |  |  |  |
| Control | −3.20 | 0.96 | −5.08 | −1.33 |  |
| 75 mg b.i.d. | 4.65 | 2.35 | 0.04 | 9.25 | 0.0480 |
| 125 mg b.i.d. | 7.77 | 2.39 | 3.10 | 12.44 | 0.00112 |
| 4 mg b.i.d. + AChEI/Mem | −3.86 | 1.01 | 5.83 | −1.88 |  |
| 4 mg b.i.d. | 5.20 | 2.03 | 1.23 | 9.17 | 0.0103 |
| Moderate AD |  |  |  |  |  |
| Control | −10.93 | 0.95 | −12.80 | −9.07 |  |
| 75 mg b.i.d. | 6.89 | 2.67 | 1.66 | 12.13 | 0.00989 |
| 125 mg b.i.d. | 5.53 | 2.66 | 0.31 | 10.75 | 0.0377 |
| 4 mg b.i.d. + AChEI/Mem | −11.91 | 0.99 | −13.85 | −9.97 |  |
| 4 mg b.i.d. | 7.70 | 2.20 | 3.39 | 12.01 | 4.6e−04 |
| LVV |  |  |  |  |  |
| Mild AD |  |  |  |  |  |
| Control | 5,789 | 374 | 5,056 | 6,522 |  |
| 75 mg b.i.d. | −2,549 | 835 | −4,185 | −913 | 0.00226 |
| 125 mg b.i.d. | −2,695 | 841 | −4,343 | −1,047 | 0.00135 |
| 4 mg b.i.d. + AChEI/Mem | 6,167 | 389 | 5,355 | 6,879 |  |
| 4 mg b.i.d. | −2,655 | 695 | −4,021 | −1,297 | 1.3e−04 |
| Moderate AD |  |  |  |  |  |
| Control | 8,023 | 372 | 7,293 | 8,753 |  |
| 75 mg b.i.d. | −2,251 | 925 | −4,065 | −438 | 0.0150 |
| 125 mg b.i.d. | −1,703 | 916 | −3,499 | 92 | 0.0630 |
| 4 mg b.i.d. + AChEI/Mem | 8,143 | 386 | 7,386 | 8,901 |  |
| 4 mg b.i.d. | −940 | 777 | −2,463 | 583 | 0.226 |
| TPV |  |  |  |  |  |
| Mild AD |  |  |  |  |  |
| Control | −1,309 | 73 | −1,452 | −1,166 |  |
| 75 mg b.i.d. | 392 | 170 | 60 | 726 | 0.0208 |
| 125 mg b.i.d. | 439 | 170 | 106 | 772 | 0.00978 |
| 4 mg b.i.d. + AChEI/Mem | −1,398 | 76 | −1,547 | −1,249 |  |
| 4 mg b.i.d. | 722 | 144 | 440 | 1,005 | 5.5e−07 |
| Moderate AD |  |  |  |  |  |
| Control | −1,649 | 59 | −1,764 | −1,534 |  |
| 75 mg b.i.d. | 469 | 155 | 164 | 773 | 0.00257 |
| 125 mg b.i.d. | 293 | 154 | −9 | 895 | 0.0570 |
| 4 mg b.i.d. + AChEI/Mem | −1,697 | 61 | −1,817 | −1,576 |  |
| 4 mg b.i.d. | 370 | 129 | 116 | 623 | 0.00425 |

TABLE 7-continued

Analyses of ADAS-cog, ADCS-ADL, LVV, TPV and HV in mild
AD and moderate AD with stratification covariate AChEI/Mem
as an interaction term in the model. Treatment with
LMTM alone is compared with the control arm as randomised
for the 75 mg b.i.d. and 125 mg b.i.d. doses. The analysis
of the 4 mg b.i.d. dose was restricted to subjects
randomised to the control arm and taking or not taking AD-labelled co-medications.

|  | Estimate | SE | 2.50% | 97.50% | p value |
|---|---|---|---|---|---|
| HV |  |  |  |  |  |
| Mild AD |  |  |  |  |  |
| Control | −115.8 | 6.6 | −126.7 | −100.8 |  |
| 75 mg b.i.d. | 16.9 | 16.0 | −14.7 | 48.1 | 0.267 |
| 125 mg b.i.d. | 40.5 | 16.0 | 9.2 | 71.9 | 0.0113 |
| 4 mg b.i.d. + AChEI/Mem | −119.5 | 6.9 | −113.1 | −106.0 |  |
| 4 mg b.i.d. | 46.7 | 13.9 | 19.6 | 73.9 | 7.5e−04 |
| Moderate AD |  |  |  |  |  |
| Control | −116.9 | 4.9 | −126.5 | −107.3 |  |
| 75 mg b.i.d. | 3.6 | 13.6 | −23.1 | 30.4 | 0.789 |
| 125 mg b.i.d. | 2.2 | 13.7 | −24.8 | 29.1 | 0.875 |
| 4 mg b.i.d. + AChEI/Mem | −116.6 | 5.1 | −126.6 | 106.6 |  |
| 4 mg b.i.d. | −2.4 | 11.2 | −24.4 | 19.6 | 0.829 |

Comparison at Baseline of Patients Taking or not-Taking AD-Labelled Medications

Given the differences in outcomes according to whether LMTM was taken as monotherapy or not, differences at baseline between these groups were analysed according to clinical severity (Table 8). No difference was found in age or sex distribution. There was a significant regional difference in mild (but not moderate) patients, in that patients not prescribed AD-labelled co-medications were found to be at sites located predominantly in Russia, Eastern Europe (Poland and Croatia) and Malaysia. There was no difference in baseline ADAS-cog or MMSE. Mild patients not taking these medications were marginally worse on the ADCS-ADL scale, but there was no difference for moderate patients. In terms of the MRI parameters at baseline, mild (but not moderate) patients not taking these medications had a slightly larger HV and LW, but there was no difference in WBV, TPV or in extent of vascular pathology burden as indicated by Fazekas score at baseline (Murray et al., 2005). Likewise no differences were found for baseline bilirubin or creatinine clearance would might suggest differences in metabolism or excretion of LMTM.

TABLE 8

Differences at baseline between patients taking or not taking AD-labelled co-medications.

|  | Mild (not taking) | Mild (taking) | p-value | Moderate (not taking) | Moderate (taking) | p-value |
|---|---|---|---|---|---|---|
| Sex |  |  | 0.142 |  |  | 0.759 |
| Age | 70.6 (5.8) | 71.7 (8.3) | 0.251 | 72.2 (9.8) | 70.1 (8.6) | 0.555 |
| Region |  |  | 0.00763 |  |  | 0.212 |
| ADAS-cog | 20.1 (5.6) | 20.2 (7.1) | 0.366 | 33.2 (9.8) | 31.2 (9.2) | 0.846 |
| ADCS-ADL | 60.7 (7.3) | 61.6 (9.7) | 0.00106 | 47.7 (16.6) | 53.2 (12.8) | 0.147 |
| MMSE | 22.3 (1.8) | 22.2 (2.2) | 0.705 | 16.5 (1.7) | 16.4 (1.9) | 0.585 |
| WBV | 946,295 (97,194) | 950,840 (116,924) | 0.664 | 925,032 (111,971) | 912,214 (100,101) | 0.357 |
| TPV | 41,841 (6,065) | 41,911 (5,733) | 0.488 | 38,208 (5,366) | 38,069 (5,101) | 0.229 |
| HV | 3,153 (647) | 2,775 (534) | 7.2e−05 | 2,654 (610) | 2738 (508) | 0.0893 |
| LVV | 37,975 (17,346) | 51,732 (24,072) | 0.00196 | 56,541 (25,660) | 53,719 (23,021) | 0.600 |
| Fazekas score |  |  | 0.149 |  |  | 0.463 |
| Creatinine clearance | 66.0 | 67.2 | 0.701 | 68.6 | 65.9 | 0.332 |
| Bilirubin | 0.51 | 0.56 | 0.235 | 0.53 | 0.52 | 0.772 |

Safety Outcomes

The gastrointestinal and urinary tracts were the body systems most commonly affected by adverse events. These were also the most common reasons for discontinuing high dose LMTM (9% and 3% of patients, respectively); in comparison, only 1-2% of control patients discontinued for these events. Of note, the incidence of gastrointestinal adverse events was about two-fold higher in patients also receiving acetylcholinesterase inhibitors (data not shown). The treatment emergent adverse events occurring in ≥5% on high dose LMTM and greater than in the control arm are shown in Table 9.

TABLE 9

Most common treatment emergent adverse events occurring in ≥5% on 75 mg b.i.d. or 125 mg b.i.d. LMTM and greater than in control arm.

| MedDRA System Organ Class/ Preferred term | Control 4 mg b.i.d. (n = 354) | High dose LMTM 75 mg b.i.d. (n = 267) | High dose LMTM 125 mg b.i.d. (n = 264) |
|---|---|---|---|
| At least one TEAE | 296 (83.6%) | 224 (83.9%) | 229 (86.7%) |
| Blood and lymphatic system disorders | 17 (4.8%) | 29 (10.9%) | 25 (9.5%) |
| Anemia | 10 (2.8%) | 22 (8.2%) | 15 (5.7%) |
| Gastrointestinal disorders | 87 (24.6%) | 105 (39.3%) | 111 (42.0%) |
| Diarrhea | 33 (9.3%) | 63 (23.6%) | 67 (25.4%) |
| Nausea | 14 (4.0%) | 22 (8.2%) | 19 (7.2%) |
| Vomiting | 2 (0.6%) | 25 (9.4%) | 18 (6.8%) |
| Infections and infestations | 88 (24.9%) | 83 (31.1%) | 76 (28.8%) |
| Urinary tract infection | 29 (8.2%) | 29 (10.9%) | 26 (9.8%) |
| Investigations | 80 (22.6%) | 87 (32.6%) | 80 (30.3%) |
| Blood folate decreased | 21 (5.9%) | 18 (6.7%) | 19 (7.2%) |
| Renal and urinary disorders | 29 (8.2%) | 61 (22.8%) | 65 (24.6%) |
| Dysuria | 3 (0.8%) | 7 (2.6%) | 27 (10.2%) |
| Pollakiuria | 6 (1.7%) | 15 (5.6%) | 18 (6.8%) |
| Urinary incontinence | 9 (2.5%) | 18 (6.7%) | 12 (4.5%) |
| Respiratory, thoracic and mediastinal disorders | 28 (7.9%) | 32 (12.0%) | 22 (8.3%) |
| Cough | 12 (3.4%) | 14 (5.2%) | 11 (4.2%) |

Adverse events of special interest (AESIs) were identified based on the known pharmacology of the MT moiety (specifically, ARIA). When the various adverse event terms are grouped, anaemia-related terms were reported in 22% of patients receiving high dose LMTM (as compared to 16% receiving control). The maximum mean changes in haemoglobin from baseline were at 6 weeks and were respectively (in g/L) −0.01 (95% CI: −0.23-0.21. p-value=0.914), −0.47 (95% CI: −0.73-−0.22, p-value=6.4e-04) and −0.93 (95% CI: −1.18-−0.68, p-value=1.2e-12) g/L at doses of 4, 75 and 125 mg b.i.d. respectively. There was no case of haemolytic anemia. Twenty two percent of patients entered the study taking an SSRI (selective serotonin reuptake inhibitor). Only 2 patients had transient symptoms consistent with serotonergic excess but the temporal course and presentation were not consistent with serotonin toxicity; both patients were treated with LMTM 75 mg b.i.d. and neither received a concomitant serotonergic drug. In total, 8 patients developed ARIA during the study (<1%), with no dose relationship.

Based on the Columbia Suicide Severity Rating Scale, 26 patients had transient responses indicating a wish to be dead. There was one suicide attempt. With respect to other significant events, 9 patients who participated in the study died, the most common reasons being progression of AD or cancer; none was related to treatment. A total of 97 patients had one or more other non-fatal serious adverse events (SAEs), consistent with the nature of the patient population and evenly distributed between the three treatment groups. These were possibly related to treatment in only 14% of the cases, the most common being convulsion (all 4 occurring in the control arm).

TABLE 10

Significant treatment emergent adverse events

| Category | Control 4 mg b.i.d. (n = 354) | High dose LMTM 75 mg b.i.d. (n = 267) | High dose LMTM 125 mg b.i.d. (n = 264) |
|---|---|---|---|
| Deaths, n (%) | 3 (0.8) | 3 (1.1) | 3 (1.1) |
| Adverse Events of Special Interest (AESIs) | | | |
| Methemoglobinemia, hemolytic anemia, and/or Heinz bodies, n (%) | 1 (0.3) | 0 (0) | 1 (0.4) |
| "Serotonin syndrome", n (%) | 0 (0) | 2 (0.7) | 0 (0) |
| ARIA, n (%) | 3 (0.8) | 4 (1.5) | 1 (0.4) |
| Other SUSARs, n (%) | 2 (0.6) | 2 (0.7) | 4 (1.5) |

Discussion

The purpose of the present study was to confirm the efficacy reported in the earlier phase 2 study using a total daily dose of 150 mg/day and to determine whether 250 mg/day could achieve superior benefit using a newly developed stabilised reduced form of MT as LM™. The study used a low dose of LMTM (4 mg b.i.d.) in the control arm rather than a true placebo to ensure blinding with respect to discolouration of excreta. The rates of decline on the ADAS-cog and ADCS-ADL scales seen in the control arm were linear and indistinguishable from those reported in recent studies. The same was found to be true for the rate of progression of brain atrophy in the mild AD group measured by change of LW in comparison with data available from the ADNI program (Frisoni et al., 2010; Nestor et al., 2008) These comparisons support the face validity of the present study.

The AChEI/Mem factor was defined as a stratification variable, along with baseline severity and geographical region, thereby ensuring that the randomised treatment arms were equally represented in all three strata. It was assumed that it would be sufficient to account for the AChEI/Mem effect by including it as an additive term in the model, along with the other stratification factors. The primary efficacy analysis as prespecified did not, however, demonstrate statistical significance on either of the primary efficacy outcomes at either 75 mg b.i.d. or 125 mg b.i.d. using this model. The same analysis showed that the AChEI/Mem factor was a statistically significant determinant of efficacy, such that those not taking AD-labelled drugs experienced a mean overall benefit relative to controls of −2.30 ADAS-cog units and 2.00 ADCS-ADL units, effects that remained statistically significant in the whole-population analysis after full correction for multiple comparisons. Since the baseline values were by definition zero, such an overall benefit could only occur if the intended active treatments produced a difference in the rate of progression relative to controls in patients taking LMTM as monotherapy.

To confirm this, the effect of LMTM treatment in the whole population was re-examined using a prespecified analysis model in which the AChEI/Mem term was included as an interaction term with visit and an interaction term with LMTM treatment, rather than only as an additive term. This analysis confirmed that treatment benefit was restricted to patients taking LMTM as monotherapy. LMTM at doses of 75 mg b.i.d. or 125 mg b.i.d. produced treatment effects of −6.25 and −5.79 ADAS-cog units respectively at 65 weeks, or 103%±23% and 83%±23% (mean±SE) of the decline over 65 weeks seen in the control arm. The corresponding effect sizes on the ADCS-ADL scale were 6.48 and 6.92, or 82%±23% and 88%±23% of the decline seen over 65 weeks in the control arm. An identical profile was found for MRI measures of progression of neocortical atrophy, with reductions of 38%±9% and 33%±9% in LVV and increases of 31%±8% and 26%±8% in TPV for the 75 mg b.i.d. and 125 mg b.i.d. doses. All of these effects were statistically robust after appropriate correction for multiple comparisons. By contrast, the decline seen at the same doses in patients taking LMTM in combination with AD-labelled treatments, who were the majority, was indistinguishable on all parameters from that seen in the control arm.

Given that the higher dose did not result in greater efficacy, we examined whether differential efficacy for LMTM as monotherapy or not might also be present at the 4 mg b.i.d. dose originally intended as a urinary and faecal discolourant. A post hoc analysis showed that 4 mg b.i.d. as monotherapy showed effects of −5.90 ADAS-cog units, 7.19 ADCS-ADL units, as well as benefits in LVV and TPV similar to those seen at the higher doses relative to patients taking the same dose in combination with standard AD treatments, and in whom the decline was again indistinguishable from the decline seen either in the control arms of recently reported studies or ADNI data.

The efficacy profiles were also similar in mild and moderate subjects. The only difference was that, in hippocampus, benefit was seen in mild patients (increased by 35.5 mm$^3$) but not in moderate patients. This is consistent with the known staging of tau aggregation pathology, whereby damage in medial temporal lobe structures occurs earlier and is more severe than in neocortex. The general concordance of benefit on the volumetric measures of rate of progression of brain atrophy by LVV, TPV and HV, particularly in mild AD, argues against the possibility that the LVV measure is simply reporting treatment-related fluid shifts. Therefore TAI therapy has potential to benefit patients at both the mild and moderate stages of the disease, and not just at more advanced stages of AD as has been supposed. Indeed, the mean treatment benefit for LMTM monotherapy relative to control was 240%±41% and 156%±39% on the ADAS-cog and ADCS-ADL in mild patients.

The benefit seen with LMTM monotherapy at doses of 4, 75 and 125 mg b.i.d. is comparable to that seen on the ADAS-cog scale at 12 months in the phase 2 study where MTC was also given as monotherapy at 47 mg MT t.i.d. (Wischik et al., 2015). We have recently reported that the absorption and distribution of MT to the brain is complex, and likely to be mediated via red cells rather than plasma, (Baddeley et al., 2015) providing a route which protects MT from first-pass metabolism. In the same study MT uptake into red cells was approximately 20-fold higher in vivo when as administered intravenously as LMTM compared with MTC, most likely due to direct red cell uptake of LMT by passive diffusion without need for prior reduction of MT$^+$ as is the case for MTC (Baddeley et al., 2015; May et al., 2004). The results of the present study suggest that MT uptake and distribution are capacity-limited by the amount that red cells can take up whilst within the portal circulation.

The reason for the loss of benefit on clinical and volumetric outcomes when LMTM is combined with symptomatic AD treatments remains to be explained, and studies are ongoing which aim to understand this better. To date, an interference at the site of action at the high affinity tau-tau binding site has been ruled out in vitro in both cell-free and cellular assays (Harrington et al., 2015). Likewise a direct effect on dissolution of LMTM tablets or complexing of LMTM with the AD medications or their excipients has been ruled out (unpublished data). The interference does not occur in certain other neurodegenerative disorders of protein aggregation (unpublished data), implying that the interference effect shown in AD is not applicable to all MT treatments of neurodegenerative disorders and may indeed be disease-specific. One possible contributory factor may be induction of the multidrug resistance protein 1 (MDR1), a transporter which is upregulated by AChEIs and memantine (Mohamed et al., 2015, 2016). We have shown that MT is a pH-dependent substrate for this pathway (unpublished data). The net effect could be enhanced efflux of MT from the brain, enhanced liver uptake leading to conjugation and inactivation of MT and faecal excretion, and also enhanced excretion of MT via the kidney. This may lower the concentration of MT at the site of action below a critical level required for efficacy in AD. Further studies to confirm this or other hypotheses are in progress.

The overall safety of LMTM as monotherapy is consistent with prior experience with MTC (Wischik et al., 2015). Adverse events affecting the gastrointestinal and urinary systems were the most common, and were also the most common reason for discontinuing high dose LMTM. Reporting of reductions in red cell indices was greater in patients receiving higher doses of LMTM, consistent with effects previously described for MTC, (Baddeley et al., 2015) although there was no significant reduction in haemoglobin at the 4 mg b.i.d. dose. Although 22% of patients were taking SSRIs, only 2 patients had transient symptoms meeting any of the criteria for serotonin toxicity, but neither of these was taking an SSRI (or any other serotonergic drug). Out of the 9 deaths that occurred during the study, none was related to treatment. Eight developed ARIA during the study (<1%) but there was no dose relationship. This frequency is consistent with the placebo rates reported in recent trials (Doody et al., 2014).

In conclusion, the results herein demonstrate the potential benefits of adding a tau-based approach to those currently available or planned for the treatment of diseases such as mild and moderate AD. A dose of LMTM as low as 4 mg b.i.d. as monotherapy may be the optimal dose in mild AD, able to produce substantial clinical benefits whilst being well tolerated and having fewer side effects than the higher doses. Such treatment would need to be introduced either prior to or following cessation of the currently available AD treatments, as the combination appears to eliminate benefit.

Example 4—Further Phase 3 Clinical Trial in Mild AD

Objectives

To examine the potential efficacy of LMTM as monotherapy in non-randomised observational cohort analyses as modified primary outcomes in an 18-months Phase 3 trial in mild AD.

Methods

Mild AD patients (n=800) were randomly assigned to 100 mg twice a day or 4 mg twice a day.

The Statistical Analysis Plan was revised in light of Example 3 (which completed earlier) prior to database lock and unblinding, to compare the 100 mg twice a day as monotherapy subgroup (n=79) versus 4 mg twice a day as randomised (n=396), and 4 mg twice a day as monotherapy (n=76) versus 4 mg twice a day as add-on therapy (n=297), with strong control of family-wise type I error.

Results

The revised analyses were statistically significant at the required threshold of p<0.025 in both comparisons on the co-primary clinical efficacy endpoints (ADAS-cog and ADCS-ADL), MRI atrophy and glucose uptake. Whole brain atrophy progressed initially as expected for mild AD in both add-on and monotherapy groups, but diverged significantly after 9 months of treatment, with the final atrophy rate in monotherapy patients typical of normal elderly controls. Differences at baseline between monotherapy and add-on patients did not account for significant differences in favour of monotherapy. Treatment response to LMTM as add-on was inversely correlated with relative basal forebrain atrophy.

CONCLUSIONS

The as-randomised analyses of two Phase 3 trials using LMTM are described herein: the first in mild to moderate AD (Example 3) and the second in mild AD (this Example). Both studies were originally designed to compare higher doses of LMTM in the range 150-250 mg/day with a low dose of 4 mg twice a day intended as a urinary discolourant to maintain blinding. It was assumed that this low dose would be ineffective, since a dose of 69 mg MT/day as MTC was found to have minimal efficacy in the Phase 2 study.

Neither Phase 3 trial study showed any difference on primary or secondary outcomes between the high doses and 4 mg twice a day. In the first study (Example 3) treatment status with cholinesterase inhibitors and/or memantine was found to be a significant covariate in the primary analysis model. Exploratory analyses showed that this was due to significantly lower rates of progression on clinical and brain atrophy endpoints in patients receiving any of the LMTM doses as monotherapy, including 4 mg twice a day, which did not appear to be explicable by cohort differences in severity at baseline.

The results of the Example 3 study raised the possibility LMTM might be most effective as a monotherapy and that the minimum effective dose might be substantially lower for LMTM than that previously expected for MTC (see e.g. WO2009/044127).

We therefore modified the primary analyses and treatment comparisons in the study described in this Example (prior to database lock and unblinding) to investigate whether the monotherapy differences could be confirmed as observational cohort comparisons defined as primary outcomes with strong control of family-wise type I error in the second independent study. The monotherapy cohort comparisons which were of particular interest in light of the earlier study were: (A) 100 mg twice a day a monotherapy compared with the controls as originally randomised, and (B) 4 mg twice a day as monotherapy compared with the same dose as add-on to standard AD treatments.

Both primary Comparisons A and B met the required statistical threshold of p<0.025 for both co-primary clinical outcomes (ADAS-cog and ADCS-ADL), as well as for volumetric MRI and glucose uptake biomarker outcomes. Specifically, patients receiving LMTM as monotherapy at either of the two doses tested had consistently better outcomes than patients receiving the same doses as add-on to cholinesterase inhibitors and/or memantine.

This confirmation of the same pattern of results in this second, independent, study argues against either the present findings or those reported as post hoc findings from the earlier mild/moderate AD study of Example 3 being the result of chance in small subgroups, although the monotherapy subgroups remain small in the present study (155 or 20% in total in the mITT analyses).

It is also unlikely that the earlier findings of Example 3 are explicable by inclusion of non-western geographies, since the present study was conducted in north America, western Europe and Australia. A clinical placebo effect in patients coming into a trial setting after previously not receiving active treatment cannot explain the same pattern of results seen in both the MRI brain atrophy and $^{18}$F-FDG-PET functional data as seen in the clinical data. A difference in withdrawal rates between patients taking or not taking standard AD treatments is also unlikely, since the overall retention rates over 18 months were similar in monotherapy (65%) and add-on (69%) treatment groups.

The pattern of atrophy at baseline in patients receiving LMTM as monotherapy was typical of mild AD and significantly different from a cohort of well characterised normal elderly controls. The annualised rate of whole brain atrophy in these patients over the first 6 months was also similar to that reported for mild AD and significantly different from normal elderly controls. Likewise glucose uptake in inferior temporal gyrus was comparable in monotherapy patients to that reported for mild AD and significantly different from MCI or normal elderly controls. In addition to meeting clinical diagnostic criteria for mild AD, the baseline imaging data therefore confirm that the patients not prescribed cholinesterase inhibitors or memantine can be taken as typical of mild AD.

Patients not receiving standard AD treatments were somewhat less impaired at study entry on the ADAS-cog, ADCS-ADL, MMSE scales, as well as in ventricular, temporoparietal and hippocampal atrophy, and temporal lobe glucose uptake. It is therefore possible that this difference in severity at baseline might have accounted for significant differences in progression. However, baseline severity was included as an additive term in the primary analysis models and was therefore corrected for. We further tested whether baseline severity or other patient characteristics could explain differences in rate of progression by undertaking sensitivity analyses with additional rate-correction terms in the analysis model. If differences in baseline characteristics explain the differences seen over 18 months, then the significant differences in favour of LMTM as monotherapy would be expected to disappear when corrected for baseline effects, as they did in a similar analysis examining differences in rate of progression according to AD treatment status in patients with MMSE 20-26 in the currently available ADNI data set (unpublished observation). Rate-correction for differences in clinical severity at baseline, APO ε4 frequency, vascular pathology load, hippocampal atrophy, temporoparietal atrophy and glucose uptake in the temporal lobe did not eliminate the significant differences in favour of LMTM monotherapy for ADAS-cog, ADCS-ADL or lateral ventricular volume. We further examined whether the differences in favour of LMTM as monotherapy depend on inclusion of patients receiving a cholinesterase inhibitor and memantine in combination, which could be taken to reflect a potential prescriber perception of risk of more rapid decline. Removing them had minimal effect on the estimates or significance of the treatment differences. It therefore appears unlikely that the relatively minor differences in severity or the other characteristics at baseline explain the significant outcome differences in favour of LMTM monotherapy over 18 months.

An analysis that is free of between-cohort confounding effects is the within-cohort comparison of annualised rate of whole brain atrophy at study entry and after 9 months of treatment with LMTM. We found that in patients receiving LMTM as monotherapy there was a significant delayed reduction in the annualised rate of whole brain atrophy. As noted above, monotherapy patients entered the study with an initial whole brain atrophy rate typical of mild AD and significantly different from that reported for normal elderly controls. After receiving LMTM as monotherapy for 9 months, the rate was reduced to that reported for normal elderly controls and significantly different from mild AD. These changes were not seen in the patients receiving LMTM as add-on therapy, who continued to decline as expected for mild AD. Similarly, the decline in temporal lobe glucose uptake in patients receiving LMTM as monotherapy was significantly less than reported for mild AD.

Decline on the ADAS-cog scale in patients receiving LMTM in combination with a cholinesterase inhibitor was found to vary inversely with atrophy in the nucleus basalis and nucleus accumbens relative to whole brain volume. A similar effect was also seen for cortical glucose uptake. The corresponding effect of basal forebrain atrophy was weak or absent for the LMTM/memantine combination and was also absent for LMTM monotherapy. Both of these basal forebrain nuclei are known to be affected by tau aggregation pathology. The role of nucleus basalis in determining treatment response may help to provide some insight into a possible mechanism underlying the negative interaction with cholinesterase inhibitors. Ascending cholinergic projections originating predominantly from nucleus basalis provide both direct activation and indirect inhibitory modulation of cortical pyramidal cells (Huang M, Felix A R, Flood D G, Bhuvaneswaran C. Hilt D, Koenig G, Meltzer H Y (2014) The novel a7 nicotinic acetylcholine receptor agonist EVP-6124 enhances dopamine, acetylcholine, and glutamate efflux in rat cortex and nucleus accumbens. *Psychopharmacology* 231, 4541-4551.; Picciotto Marina R, Higley Michael J, Mineur Yann S (2012) Acetylcholine as a Neuromodulator. Cholinergic Signaling Shapes Nervous System Function and Behavior. *Neuron* 76, 116-129). Memantine also increases release of acetyl choline in nucleus accumbens (Shearman E, Rossi S. Szasz B, Juranyi Z, Fallon S, Pomara N, Sershen H, Lajtha A (2006) Changes in cerebral neurotransmitters and metabolites induced by acute donepezil and memantine administrations: A microdialysis study. *Brain Res Bull* 69, 204-213) which modulates cortical activity indirectly. Long-term inhibition of cholinesterase activity combined with loss of inhibitory modulation may therefore result in chronic hyperactivation of pyramidal cells in cortex (and in CA 1-3 of hippocampus) which are the principal sites of neurofibrillary degeneration in AD (Lewis D A, Campbell M J, Terry R D, Morrison J H (1987) Laminar and regional distributions of neurofibrillary tantles and neuritic plaques in Alzheimer's disease: a quantitative study of visual and auditory cortices. *J Neurosci* 7, 1799-1808). It is therefore possible that the relative severity of basal forebrain pathology together with chronic choline esterase inhibition may determine the degree of hyperactivation of cortical pyramidal cells and that this impairs the action of MT even at high dose. We show that whereas the treatment response to LMTM as add-on to approved treatments for AD varies according to the severity of relative basal forebrain atrophy, the effect of LMTM as monotherapy does not. The difference in treatment response between LMTM monotherapy and add-on therapy cannot therefore be attributed simply to cohort differences between patients prescribed or not prescribed such treatments. It also cannot be attributed to relative lack of pathology, since patients with the greatest basal forebrain atrophy responded significantly better to monotherapy than to combination treatment.

The potential for LMTM to be active at the low dose of 4 mg twice a day and the lack of dose-response are at first sight surprising given the results of an earlier Phase 2 placebo-controlled study using the oxidised form of the methylthioninium (MT) moiety as methylthioninium chloride (MTC) (Wischik, 2015). The stable reduced form of MT (as LMTM) was developed to overcome the absorption limitations observed for MTC. LMTM has 20-fold better red cell uptake than MTC in vivo and also better brain uptake. Recent studies in rodents dosed orally with LMTM to simulate the 4 mg twice a day dose in humans found brain levels of MT to be on 0.1-0.2 µM, similar to the steady state concentration estimated for the minimum effective dose of MTC. A concentration of approximately 0.05 µM appears to be adequate for a range of reported potentially beneficial effects of the MT moiety such as enhancement of autophagy and enhancement of mitochondrial function. The concentration required for dissolution of PHFs and oligomers in vitro is approximately $\frac{1}{10}^{th}$ that of aggregated tau, implying that a concentration of 0.05 µM may be adequate in vivo, given the brain concentrations of aggregated tau that have been reported. There is no dose-response for oligomer disaggregation in vitro, and higher doses of LMTM did not result in greater reduction in tau pathology in transgenic mouse models, at least in the range tested (Melis, 2015) Effects of oxidized and reduced forms of methylthioninium in two transgenic mouse tauopathy models. *Behav Pharmacol* 26, 353-368). This suggests that there may be a critical threshold for activity at the tau aggregation inhibitor target, and the effect of higher doses may plateau or may even become negative at brain concentrations above 1 µM (Melis, 2015). Several results suggest that 4 mg twice a day may serve better than 100 mg twice a day. The clinical differences in favour of 4 mg twice a day were seen at both CDR 0.5 and 1.0, but only at CDR 0.5 at the higher dose, and the glucose uptake difference in temporal cortex occurred earlier at the lower dose.

The lower dose of 4 mg twice a day had a better overall clinical profile than 100 mg twice a day. The withdrawal rate over 18 months for the 4 mg twice a day dose was less (25%, 94/296) than at 100 mg twice a day (46%, 182/399), and the adverse event profile was more benign with respect to the diarrhoea, dysuria and decreased haemoglobin. There is no increased risk of cerebral microhaemorrhages or oedema with LMTM even at the higher dose, since the ARIA rates observed in both Phase 3 studies reported herein were similar to those previously reported for placebo controls (Doody, 2014; Salloway, 2014).

The differences in favour of LMTM as monotherapy are based on observational cohort analyses, albeit defined a priori as statistically primary outcomes for the modified analysis we report here. This pattern of results has been seen now in both separate Phase 3 studies, implying that the effects are consistent across studies. The differences favouring monotherapy are also internally consistent across a range of clinical outcomes, and the clinical outcomes are consistent with the neuroimaging outcomes in both studies.

Allowing for differences in absorption between LMTM and MTC, the results are also consistent with the earlier Phase 2 placebo-controlled study supporting potential efficacy of the MT moiety as monotherapy, and underline the potential beneficial clinical and biological effects of LMTM as monotherapy at the safe and well-tolerated dose of around 4 mg twice a day.

REFERENCES FOR DISCUSSION OF BACKGROUND ART

Alzheimer A. Über eine eigenartige Erkrankung der Hirnrinde. *Allg Z Psych Psych-gerich Med* 1907: 64:146-8 [German].

Alzheimer's Disease International. World Alzheimer Report 2015: The global impact of dementia, an analysis of prevalence, incidence, cost and trends. *World Alzheimer Report* 2015.

Arriagada P W, Growdon J H, Hedley-White E T, Hyman B T. Neurofibrillary tangles but not senile plaques parallel duration and severity of Alzheimers disease. *Neurology* 1992; 42: 631-9.

Baddeley T, C. McCaffrey J, Storey J M D, et al. Complex disposition of methyfthioninium redox forms determines efficacy in tau aggregation inhibitor therapy for Alzheimer's disease. *J Pharmacol Exptl Therapeutics* 2015; 352: 110-8.

Braak H, Del Tredici K. The pathological process underlying Alzheimer's disease in individuals under thirty. *Acta Neuropathol* 2011; 121: 171-81.

Brier M R. Gordon B, Friedrichsen K, et al. Tau and Aβ imaging, CSF measures, and cognition in Alzheimer's disease. *Science Transl Med* 2016; 8: 338ra66.

DiSanto A R, Wagner J G. Pharmacokinetics of highly ionized drugs. II. Methylene blue-absorption, metabolism, and excretion in man and dog after oral administration. *J Pharmaceut Sci* 1972; 61: 1086-90.

Geerts H, Spiros A, Roberts P, Carr R. A strategy for developing new treatment paradigms for neuropsychiatric and neurocognitive symptoms in Alzheimer's disease. *Front Pharmacol* 2013; 4: 47.

Giannakopoulos P, Herrmann F R, Bussiere T, et al. Tangle and neuron numbers, but not amyloid load, predict cognitive status in Alzheimers disease. *Neurology* 2003; 60: 1495-500.

Harrington C R, Storey J M D, Clunas S, et al. Cellular models of aggregation-dependent template-directed proteolysis to characterize tau aggregation inhibitors for treatment of Alzheimers disease. *J Biol Chem* 2015; 290: 10862-75.

Huang Y, Mucke L. Alzheimer mechanisms and therapeutic strategies. *Cell* 2012; 148: 1204-22.

Josephs K A, Whitwell J L, Ahmed Z, et al. b-Amyloid burden is not associated with rates of brain atrophy. *Ann Neurol* 2008; 63: 204-12.

Lai R Y K, Harrington C R, Wischik C M. Absence of a role for phosphorylation in the tau pathology of Alzheimer's disease. *Biomolecules* 2016; 6: 19.

Maruyama M, Shimada H, Suhara T, et al. Imaging of tau pathology in a tauopathy mouse model and in Alzheimer patients compared to normal controls. *Neuron* 2013; 79:1094-108.

May J M, Qu Z-c, Cobb C E. Reduction and uptake of methylene blue by human erythrocytes. *Am J Physiol—Cell Physiol* 2004; 286: C1390-C8.

Melis V, Magbagbeolu M, Rickard J E, et al. Effects of oxidized and reduced forms of methylthioninium in two transgenic mouse tauopathy models. *Behav Pharmacol* 2015: 26: 353-68.

Mukaetova-Ladinska E B, Garcia-Sierra F. Hurt J, et al. Staging of cytoskeletal and b-amyloid changes in human isocortex reveals biphasic synaptic protein response during progression of Alzheimer's disease. *Am J Pathol* 2000; 157: 623-36.

Mullane K, Williams M. Alzheimer's therapeutics: Continued clinical failures question the validity of the amyloid hypothesis—but what lies beyond? *Biochem Pharmacol* 2013: 85: 289-305.

Peter C, Hongwan D, Kupfer A, Lauterburg B H. Pharmacokinetics and organ distribution of intravenous and oral methylene blue. *Eur J Clin Pharmacol* 2000; 56: 247-50.

Schneider A, Biemat J, von Bergen M, Mandelkow E, Mandelkow E-M. Phosphorylation that detaches tau protein from microtubules (Ser262, Ser214) also protects it against aggregation into Alzheimer paired helical filaments. *Biochemistry* 1999; 38: 3549-58.

Winblad B, Amouyel P, Andreu S, et al. Defeating Alzheimers disease and other dementias: a priority for European science and society. *Lancet Neurol* 2016; 15: 455-532.

Wischik C M, Crowther R A, Stewart M, Roth M. Subunit structure of paired helical filaments in Alzheimer's disease. *J Cell Biol* 1985; 100: 1905-12.

Wischik C M, Edwards P C, Lai R Y K, et al. Quantitative analysis of tau protein in paired helical filament preparations: implications for the role of tau protein phosphorylation in PHF assembly in Alzheimer's disease. *Neurobiol Aging* 1995; 16: 409-31.

Wischik C M, Edwards P C, Lai R Y K, Roth M, Harrington C R. Selective inhibition of Alzheimer disease-like tau aggregation by phenothiazines. *Proc Nat Acad Sci USA* 1996; 93:11213-8.

Wischik C M, Harrington C R, Storey J M D. Tau-aggregation inhibitor therapy for Alzheimer's disease. *Biochem Pharmacol* 2014; 88: 529-39.

Wischik C M, Novak M. Edwards P C, Klug A, Tichelaar W, Crowther R A. Structural characterization of the core of the paired helical filament of Alzheimer disease. *Proc Natl Acad Sci USA* 1988; 85: 4884-8.

Wischik C M, Novak M. Thøgersen H C, et al. Isolation of a fragment of tau derived from the core of the paired helical filament of Alzheimer's disease. *Proc Natl Acad Sci USA* 1988; 85: 4506-10.

Wischik C M, Staff R T, Wischik D J, et al. Tau aggregation inhibitor therapy: an exploratory phase 2 study in mild or moderate Alzheimer's disease. *J Alzheimer's Dis* 2015; 44: 705-20.

Wischik C M, Wischik D J, Storey J M D, Harrington C R. Rationale for tau aggregation inhibitor therapy in Alzheimer's disease and other tauopathies. In: Martinez A, ed. Emerging drugs and targets for Alzheimer's disease Volume 1: Beta-amyloid, tau protein and glucose metabolism. Cambridge: Royal Society of Chemistry; 2010: 210-32.

REFERENCES FOR PROTEINS INVOLVED IN DISEASES OF PROTEIN AGGREGATION

Abrahamson, M., Jonsdottir, S., Olafsson, I. & Grubb, A. (1992) Hereditary cystatin C amyloid angiopathy identification of the disease-causing mutation and specific diagnosis by polymerase chain reaction based analysis. *Human Genetics* 89, 377-380.

Andersen, P. (2006) Amyotrophic lateral sclerosis associated with mutations in the CuZn superoxide dismutase gene. *Current Neurology and Neuroscience Reports* 6, 37-46.

Arai, T., Hasegawa, M., Nonoka, T., Kametani, F., Yamashita, M., Hosokawa, M., Niizato, K., Tsuchiya, K., Kobayashi, Z., Ikeda, K., Yoshida, M., Onaya, M., Fujishiro. H. & Akiyama, H. (2010) Phosphorylated and cleaved TDP-43 in ALS, FTLD and other neurodegenerative disorders and in cellular models of TDP-43 proteinopathy. Neuropathology 30, 170-181.

Askanas, V., Engel, W. K. & Nogalska, A. (2009) Inclusion body myositis: a degenerative muscle disease associated with intra-muscle fiber multi-protein aggregates, proteasome inhibition, endoplasmic reticulum stress and decreased lysosomal degradation. Brain Pathology 19, 493-506.

Barmada, S. J., Skibinski, G., Korb, E., Rao, E. J., Wu, J. Y. & Finkbeiner, S. (2010) Cytoplasmic mislocalization of TDP-43 is toxic to neurons and enhanced by a mutation associated with familial amyotrophic lateral sclerosis. Journal of Neuroscience 30, 639-649.

Blair, I. P., Williams, K. L., Warraich, S. T., Dumall, J. C., Thoeng, A. D., Manavis, J., Blumbergs, P. C., Vucic, S., Kieman. M. C. & Nicholson, G. A. (2010) FUS mutations in amyotrophic lateral sclerosis: clinical, pathological, neurophysiological and genetic analysis. Journal of Neurology Neurosurgery and Psychiatry 81, 639-645.

Booth, D. R., Sunde, M., Bellotti, V., Robinson, C. V., Hutchinson, W. L., Fraser, P. E., Hawkins, P. N., Dobson, C. M., Radford, S. E., Blake. C. C. F. & Pepys. M. B. (1997) Instability, unfolding and aggregation of human lysozyme variants underlying amyloid fibrillogenesis. Nature 385, 787-793.

Byrne, S., Walsh. C., Lynch, C., Bede, P., Elamin, M., Kenna, K., McLaughlin, R. & Hardiman, O. (2011) Rate of familial amyotrophic lateral sclerosis: a systematic review and meta-analysis. Journal of Neurology, Neurosurgery & Psychiatry 82, 623-627.

Carrell, R. W. & Gooptu, B. (1998) Conformational changes and disease—serpins, prions and Alzheimer's. *Current Opinion in Structural Biology* 8, 799-809.

Chen-Plotkin, A. S., Lee, V. M. Y. & Trojanowski, J. Q. (2010) TAR DNA-binding protein 43 in neurodegenerative disease. Nature Reviews Neurology 6, 211-220.

Chiti, F., Webster, P., Taddei, N., Clark, A., Stafani, M., Ramponi, G. & Dobson, C. (1999) Designing conditions for in vitro formation of amyloid protofilaments and fibrils. *Proceedings of the National Academy of Sciences, USA* 96, 3590-3594.

Cox, L. E., Ferraiuolo, L., Goodall, E. F., Heath, P. R., Higginbottom, A., Mortiboys, H., Hollinger, H. C., Hartley. J. A., Brockington, A., Bumess, C. E., Morrison, K. E., Wharton, S. B., Grierson, A. J., Ince, P. G., Kirby, J. & Shaw, P. J. (2010) Mutations in CHMP2B in lower motor neuron predominant amyotrophic lateral sclerosis (ALS). PLOS One 5, e9872.

Czech, C., Tremp, G. & Pradier, L. (2000) Presenilins and Alzheimer's disease: biological functions and pathogenic mechanisms. *Progress in Neurobiology* 60, 363-384.

Davis, R. L., Shrimpton, A. E., Holohan, P. D., Bradshaw, C., Feiglin, D., Collins, G. H., Sonderegger, P., Kinter, J., Becker, L. M., Lacbawan, F., Krasnewich, D., Muenke, M., Lawrence, D. A., Yerby, M. S., Shaw, C.-M., Gooptu, B., Elliott, P. R., Finch, J. T., Carrell, R. W. & Lomas, D. A. (1999) Familial dementia caused by polymerization of mutant neuroserpin. Nature 401, 376-379.

DiFiglia, M., Sapp, E., Chase, K. O., Davies, S. W., Bates, G. P., Vonsattel, J. P. & Aronin, N. (1997) Aggregation of huntingtin in neuronal intranuclear inclusions and dystrophic neurites in brain. Science 277, 1990-1993.

Dische, F. E., Wemstedt, C., Westermark, G. T., Westermark, P., Pepys, M. B., Rennie, J. A., Gilbey, S. G. & Watkins, P. J. (1988) Insulin as an amyloid-fibril protein at sites of repeated insulin injections in a diabetic patient. *Diabetologia* 31, 158-161.

Elden, A. C., Kim, H.-J., Hart, M. P., Chen-Plotkin, A. S., Johnson, B. S., Fang, X., Armakola, M., Geser, F., Greene, R., Lu, M. M., Padmanabhan, A., Clay-Falcone, D., McCluskey, L., Elman, L., Juhr, D., Gruber. P. J., Rub, U., Auburger, G., Trojanowski, J. Q., Lee, V. M. Y., Van Deerlin, V. M., Bonini, N. M. & Gitler, A. D. (2010) Ataxin-2 intermediate-length polyglutamine expansions are associated with increased risk for ALS. Nature 466, 1069-1075.

Finsterer, J (2009) Mitochondrial disorders, cognitive impairment and dementia. *J. Neurol. Sci.* 283:143-148

Gasset, M., Bladwin, M. A., Lloyd, D. H., abriel, J.-M., Holtzman, D. M., Cohen, F. E., Fletterick, R. & Prusiner, S. B. (1992) Predicted a-helical region of the prion protein when synthesized as peptides form amyloid. *Proceedings of the National Academy of Sciences, USA* 89, 10940-10944.

Gendron, T. F., Josephs, K. A. & Petrucelli, L. (2010) Review: Transactive response DNA-binding protein 43 (TDP-43): mechanisms of neurodegeneration. Neuropathology and Applied Neurobiology 36, 97-112.

Geser, F., Lee, V. M.-Y. & Trojanowski, J. Q. (2010) Amyotrophic lateral sclerosis and frontotemporal lobar degeneration: A spectrum of TDP-43 proteinopathies. Neuropathology 30, 103-112.

Gitcho, M. A., Baloh, R. H., Chakraverty, S., Mayo, K., Norton, J. B., Levitch, D., Hatanpaa, K. J., White, C. L., III, Bigio, E. H., Caselli, R., Baker, M., AI-Lozi, M. T., Morris, J. C., Pestronk, A., Rademakers, R., Goate, A. M. & Caims, N. J. (2008) TDP-43 A315T mutation in familial motor neuron disease. Annals of Neurology 63, 535-538.

Glenner, G. G. & Wong, C. W. (1984) Alzheimer's disease: initial report of the purification and characterisation of a novel cerebrovascular amyloid protein. *Biochemical and Biophysical Research Communications* 120, 885-890.

Goate, A., Chartier-Harlin, M.-C., Mullen, M., Brown, J., Crawford, F., Fidani, L., Giuffra, L., Haynes, A., Irving, N., James, L., Mant, R., Newton, P., Rooke, K., Roques, P., Talbot. C., Pericak-Vance, M., Roses, A., Williamson, R., Rossor, M., Owen, M. & Hardy, J. (1991) Segregation of a missense mutation in the amyloid precursor protein gene with familial Alzheimer's disease. Nature 349, 704-706.

Gorevic, P. D., Casey, T. T., Stone, W. J., DiRaimondo, C. R., Prelli, F. C. & Frangione, B. (1985) b-2 Microglobulin is an amyloidogenic protein in man. *Journal of Clinical Investigation* 76, 2425-2429.

Gustavsson, A., Engström, U. & Westermark, P. (1991) Normal transthyretin and synthetic transthyretin fragments form amyloid-like fibrils in vitro. *Biochemical and Biophysical Research Communications* 175.1159-1164.

Higashi, S., Tsuchiya, Y., Araki, T., Wada, K. & Kabuta, T. (2010) TDP-43 physically interacts with amyotrophic lateral sclerosis-linked mutant CuZn superoxide dismutase. Neurochemistry International 57, 906-913.

Hutton, M., Lendon, C., Rizzu, P., Baker, M., Froelich, S., Houlden, H., Pickering-Brown, S., Chakraverty, S., Isaacs, A., Grover, A., Hackett, J., Adamson, J., Lincoln, S., Dickson, D., Davies. P., Petersen, R. C., Stevens, M., de Graaf, E., Wauters, E., van Baren, J., Hillebrand, M., Joosse, M., Kwon, J. M., Nowotny, P., Che, L. K., Norton, J., Morris, J. C., Reed, L. A., Trojanowski, J. Q., Basun, H., Lannfelt, L., Neystat, M., Fahn, S., Dark, F., Tannenberg, T., Dodd, P. R., Hayward, N., Kwok, J. B. J., Schofield, P. R., Andreadis, A., Snowden, J., Craufurd, D., Neary, D., Owen, F., Oostra, BA., Hardy, J., Goate, A., van Swieten, J., Mann, D., Lynch, T. & Heutink, P. (1998) Association of missense and 5'-splice-site mutations in tau with the inherited dementia FTDP-17. *Nature* 393, 702-705.

Igaz, L. M., Kwong, L. K., Chen-Plotkin, A., Winton, M. J., Unger, T. L., Xu, Y., Neumann, M., Trojanowski, J. Q. & Lee, V. M. Y. (2009) Expression of TDP-43 C-terminal fragments in vitro recapitulates pathological features of TDP-43 proteinopathies. Journal of Biological Chemistry 284, 8516-8524.

Jinwal, UK, Miyata, Y, Koren. J, III, Jones, JR. Trotter, J H et al. (2009) Chemical manipulation of Hsp70 ATPase activity regulates tau stability. *J. Neurosci.* 29:12079-12088

Johansson, B., Wemstedt, C. & Westermark, P. (1987) Atrial natriuretic peptide deposited as atrial amyloid fibrils. *Biochemical and Biophysical Research Communications* 148, 1087-1092.

Johnson, B. S., McCaffery, J. M., Lindquist, S. & Gitler, A. D. (2008) A yeast TDP-43 proteinopathy model: Exploring the molecular determinants of TDP-43 aggregation and cellular toxicity. Proceedings of the National Academy of Sciences 105, 6439-6444.

Johnson, B. S., Snead, D., Lee, J. J., McCaffery, J. M., Shorter, J. & Gitler, A. D. (2009) TDP-43 is intrinsically aggregation-prone, and amyotrophic lateral sclerosis-linked mutations accelerate aggregation and increase toxicity. Journal of Biological Chemistry 284, 20329-20339.

Johnson, J. O., Mandrioli, J., Benatar, M., Abramzon, Y., Van Deerlin, V. M., Trojanowski, J. Q., Gibbs, J. R., Brunetti, M., Gronka, S., Wuu, J., Ding, J., McCluskey, L., Martinez-Lage, M., Falcone, D., Hemandez, D. G., Arepalli, S., Chong, S., Schymick, J. C., Rothstein, J., Landi, F., Wang, Y.-D., Calvo, A., Mora, G., Sabatelli, M., Monsurrb, M. R., Battistini, S., Salvi, F., Spataro. R., Sola, P., Borghero, G., Galassi, G., Scholz, S. W., Taylor, J. P., Restagno, G., ChiO, A. & Traynor, B. J. (2010) Exome sequencing reveals VCP mutations as a cause of familial ALS. Neuron 68, 857-864.

Kabashi, E., Lin, L., Tradewell, M. L., Dion, P. A., Bercier, V., Bourgouin, P., Rochefort, D., Bel Hadj, S., Durham, H. D., Velde, C. V., Rouleau, G. A. & Drapeau, P. (2010) Gain and loss of function of ALS-related mutations of TARDBP (TDP-43) cause motor deficits in vivo. Human Molecular Genetics 19, 671-683.

Kabashi, E., Valdmanis, P. N., Dion, P., Spiegelman, D., McConkey, B. J., Velde, C. V., Bouchard, J.-P., Lacomblez, L., Pochigaeva, K., Salachas, F., Pradat, P.-F., Camu, W., Meininger. V., Dupre, N. & Rouleau, G. A. (2008) TARDBP mutations in individuals with sporadic and familial amyotrophic lateral sclerosis. Nature Genetics 40, 572-574.

Ling, S.-C., Albuquerque, C. P., Han, J. S., Lagier-Tourenne, C., Tokunaga, S., Zhou, H. & Cleveland, D. W. (2010) ALS-associated mutations in TDP-43 increase its stability and promote TDP-43 complexes with FUS/TLS. Proceedings of the National Academy of Sciences 107, 13318-13323.

Lomas. D. A., Evans, D. L., Finch, J. T. & Carrell, R. W. (1992) The mechanism of Z ai-antitrypsin accumulation in the liver. Nature 357, 605-607.

Love, S., Bridges, L. R. & Case, C. P. (1995) Neurofibrillary tangles in Niemann-Pick disease type C. Brain 118, 119-129.

Mackenzie, I. R. A., Bigio, E. H., Ince, P. G., Geser, F., Neumann, M., Caims, N.J., Kwong, L. K., Forman, M. S., Ravits, J., Stewart, H., Eisen, A., McClusky, L., Kretzschmar, H. A., Monoranu, C. M., Highley, J. R., Kirby, J., Siddique, T., Shaw, P. J., Lee, V. M. Y. & Trojanowski, J. Q. (2007) Pathological TDP-43 distinguishes sporadic amyotrophic lateral sclerosis from amyotrophic lateral sclerosis with SOD1 mutations. Annals of Neurology 61, 427-434.

Mackenzie, I. R. A., Rademakers, R. & Neumann, M. (2010) TDP-43 and FUS in amyotrophic lateral sclerosis and frontotemporal dementia. The Lancet Neurology 9, 995-1007.

Maury, C. P. & Baumann, M. (1990) Isolation and characterization of cardiac amyloid in familial amyloid polyneuropathy type IV (Finnish): relation of the amyloid protein to variant gelsolin. *Biochimica et Biophysica Acta* 1096, 84-86.

Neary, D., Snowden, J. S., Gustafson, L., Passant, U., Stuss, D., Black, S., Freedman, M., Kertesz, A., Robert, P. H., Albert, M., Boone, K., Miller, B. L., Cummings, J. & Benson, D. F. (1998) Frontotemporal lobar degeneration: a consensus on clinical diagnostic criteria. Neurology 51, 1546-1554.

Neumann, M. (2009) Molecular neuropathology of TDP-43 proteinopathies. International Journal of Molecular Sciences 10, 232-246.

Neumann, M., Sampathu, D. M., Kwong, L. K., Truax, A. C., Micsenyi, M. C., Chou, T. T., Bruce, J., Schuck, T., Grossman, M., Clark, C. M., McCluskey, L. F., Miller, B. L., Masliah, E., Mackenzie, I. R., Feldman, H., Feiden, W., Kretzschmar, H. A., Trojanowski, J. Q. & Lee, V. M. Y. (2006) Ubiquitinated TDP-43 in frontotemporal lobar degeneration and amyotrophic lateral sclerosis. Science 314, 130-133.

Nonaka, T., Kametani, F., Arai, T., Akiyama, H. & Hasegawa, M. (2009) Truncation and pathogenic mutations facilitate the formation of intracellular aggregates of TDP-43. Human Molecular Genetics 18, 3353-3364.

Ohmi, K., Kudo, L. C., Ryazantsev, S., Zhao, H.-Z., Karsten, S. L. & Neufeld, E. F. (2009) Sanfilippo syndrome type B, a lysosomal storage disease, is also a tauopathy. Proceedings of the National Academy of Sciences 106, 8332-8337.

Orr, H. T. & Zoghbi, H. Y. (2007) Trinucleotide repeat disorders. *Annual Review of Neuroscience* 30, 575-621.

Paulson, H. L. (1999) Human genetics '99: trinucleotide repeats. *American Joumalof Human Genetics* 64, 339-345.

Pepys, M. B., Hawkins, P. N., Booth, D. R., Vigushin, D. M., Tennent, G. A., Soutar, A. K., Totty, N., Nguyen, O., Blake, C. C. F., Terry, C. J., Feest, T. G., Zalin, A. M. & Hsuan, J. J. (1993) Human lysozyme gene mutations cause hereditary systemic amyloidosis. *Nature* 362, 553-557.

Polymeropoulos, M. H., Lavedan, C., Leroy, E., Ide, S. E., Dehejia, A., Dutra, A., Pike, B., Root, H., Rubenstein, J., Boyer, R., Stenroos, E. S., Chandrasekharappa, S., Athanassiadou, A., Papaetropoulos, T., Johnson, W. G., Lazzarini, A. M., Duvoisin. R. C., Di lorio, G., Golbe, L. I. & Nussbaum, R. L. (1997) Mutation in the a-synuclein gene identified in families with Parkinson's disease. *Science* 276, 2045-2047.

Prusiner, S. B., Scott, M. R., DeArmond, S. J. & Cohen, F. E. (1998) Prion protein biology. *Cell* 93, 337-348.

Seetharaman, S. V., Prudencio, M., Karch, C., Holloway, S. P., Borchelt, D. R. & Hart, P. J. (2009) Immature copper-zinc superoxide dismutase and familial amyotrophic lateral sclerosis. *Experimental Biology and Medicine* 234, 1140-1154.

Seilhean, D., Cazeneuve, C., Thures, V., Russaouen, O., Millecamps, S., Salachas, F., Meininger, V., LeGuem, E. & Duyckaerts. C. (2009) Accumulation of TDP-43 and α-actin in an amyotrophic lateral sclerosis patient with the K171 ANG mutation Acta Neuropathologica 118, 561-573.

Shibata, N., Hirano, A., Kobayashi, M., Siddique, T., Deng. H. X., Hung, W. Y., Kato, T. & Asayama, K. (1996) Intense superoxide dismutase-1 immunoreactivity in intracytoplasmic hyaline inclusions of familial amyotrophic lateral sclerosis with posterior column involvement. *Journal of Neuropathology and Experimental Neurology* 55, 481-490.

Sletten, K., Westermark, P. & Natvig, J. B. (1976) Characterization of amyloid fibril proteins from medullary carcinoma of the thyroid. *Journal of Experimental Medicine* 143, 993-998.

Spillantini, M. G., Crowther, R. A., Jakes, R., Hasegawa, M. & Goedert, M. (1998) a-Synuclein in filamentous inclusions of Lewy bodies from Parkinson's disease and dementia with Lewy bodies. *Proceedings of the National Academy of Sciences, USA* 95, 6469-6473.

Sreedharan, J., Blair, I. P., Tripathi, V. B., Hu, X., Vance. C., Rogelj, B., Ackerley, S., Dumall, J. C., Williams, K. L., Buratti, E., Baralle, F., de Belleroche, J., Mitchell, J. D., Leigh, P. N., AI-Chalabi, A., Miller, C. C., Nicholson, G. & Shaw, C. E. (2008) TDP-43 mutations in familial and sporadic amyotrophic lateral sclerosis. *Science* 319, 1668-1672.

Uemichi, T., Liuepnicks, J. j. & Benson, M. D. (1994) Hereditary renal amyloidosis with a novel variant fibrinogen. *Journal of Clinical Investigation* 93, 731-736.

van Bebber, F., Paquet, D., Hruscha, A., Schmid, B. & Haass, C. (2010) Methylene blue fails to inhibit Tau and polyglutamine protein dependent toxicity in zebrafish. *Neurobiology of Disease* 39, 265-271.

Vance, C., Rogelj, B., Hortobagyi, T., De Vos, K. J., Nishimura, A. L., Sreedharan, J., Hu. X., Smith, B., Ruddy, D., Wright, P., Ganesalingam, J., Williams, K. L., Tripathi, V., Al-Saraj, S., AI-Chalabi, A., Leigh, P. N., Blair, I. P., Nicholson, G., de Belleroche, J., Gallo, J.-M., Miller, C. C. & Shaw, C. E. (2009) Mutations in FUS, an RNA processing protein, cause familial amyotrophic lateral sclerosis type 6. *Science* 323, 1208-1211.

Westermark, P., Engstrom, U., Johnson, K. H., Westermark, G. T. & Betsholtz, C. (1990) Islet amyloid polypeptide: pinpointing amino acid residues linked to amyloid fibril formation. *Proceedings of the National Academy of Sciences, USA* 87, 5036-5040.

Westermark, P., Johnson, K. H. & Pitkanen, P. (1985) Systemic amyloidosis: A review with emphasis on pathogenesis. *Applied Physiology* 3, 55-68.

Westermark, P., Johnson, K. H., O'Brien. T. D. & Betsholtz. C. (1992) Islet amyloid polypeptide—a novel controversy in diabetes research. *Diabetologia* 35, 297-303.

Wijesekera, L. & Leigh, P. N. (2009) Amyotrophic lateral sclerosis. *Orphanet Journal of Rare Diseases* 4, 3.

Wischik, C. M., Novak, M., Thegersen, H. C., Edwards, P. C., Runswick, M. J., Jakes, R., Walker, J. E., Milstein, C., M., R. & Klug, A. (1988) Isolation of a fragment of tau derived from the core of the paired helical filament of Alzheimer's disease. *Proceedings of the National Academy of Sciences, USA* 85, 4506-4510.

Yamashita, M., Nonaka, T., Arai, T., Kametani, F., Buchman, V. L., Ninkina, N., Bachurin, S. O., Akiyama, H., Goedert, M. & Hasegawa, M. (2009) Methylene blue and dimebon inhibit aggregation of TDP-43 in cellular models. *FEBS Letters* 583, 2419-2424.

Zhang, Y.-J., Xu, Y.-F., Cook, C., Gendron, T. F., Roettges, P., Link, C. D., Lin, W.-L., Tong, J., Castanedes-Casey, M., Ash, P., Gass, J., Rangachar, V., Buratti, E., Baralle, F., Golde, T. E., Dickson, D. W. & Petrucelli, L. (2009) Aberrant cleavage of TDP-43 enhances aggregation and cellular toxicity. Proceedings of the National Academy of Sciences 106, 7607-7612.

REFERENCES FOR EXAMPLES 3 AND 4

Alusik S, Kalatova D, Paluch Z. Serotonin syndrome. *Neuroendocrinol Left* 2014; 35: 265-73.

Baddeley T, C., McCaffrey J, Storey J M D, et al. Complex disposition of methylthioninium redox forms determines efficacy in tau aggregation inhibitor therapy for Alzheimer's disease. *J Pharmacol Exptl Therapeutics* 2015; 352: 110-8.

Doody R S, Thomas R G, Farlow M, et al. Phase 3 trials of solanezumab for mild-to-moderate Alzheimer's disease. *New Eng J Med* 2014; 370: 311-21.

Fox N C, Freeborough P A. Brain atrophy progression measured from registered serial MRI: Validation and application to Alzheimers disease. *J Magnetic Reson Imaging* 1997; 7: 1069-75.

Frisoni G B, Fox N C, Jack C R, Scheltens P, Thompson P M. The clinical use of structural MRI in Alzheimer disease. *Nature Reviews Neurology* 2010; 6: 67-77.

Harrington C R, Storey J M D, Clunas S, et al. Cellular models of aggregation-dependent template-directed proteolysis to characterize tau aggregation inhibitors for treatment of Alzheimer's disease. *J Biol Chem* 2015; 290: 10862-75.

May J M, Qu Z-c, Cobb C E. Reduction and uptake of methylene blue by human erythrocytes. *Am J Physiol—Cell Physiol* 2004; 286: C1390-C8.

Melis V, Magbagbeolu M, Rickard J E, et al. Effects of oxidized and reduced forms of methylthioninium in two transgenic mouse tauopathy models. *Behav Pharmacol* 2015; 26: 353-68.

Mohamed L A, Keller J N, Kaddoumi A. Role of P-glycoprotein in mediating rivastigmine effect on amyloid-β brain load and related pathology in Alzheimer's disease mouse model. *Biochim Biophys Acta* 2016; 1862: 778-87.

Mohamed L A, Qosa H. Kaddoumi A. Age-related decline in brain and hepatic clearance of amyloid-beta is rectified by the cholinesterase inhibitors donepezil and rivastigmine in rats. *ACS Chem Neurosci* 2015; 6: 725-36.

Murray A D, Staff R T, Shenkin S D, Deary I J, Starr J M, Whalley U. Brain white matter hyperintensities: relative importance of vascular risk factors in nondemented elderly people. *Radiology* 2005: 237: 251-7.

Nestor S M, Rupsingh R, Borrie M, et al. Ventricular enlargement as a possible measure of Alzheimer's disease progression validated using the Alzheimer's disease neuroimaging initiative database. *Brain* 2008; 131: 2443-54.

Ramsay R R, Dunford C, Gillman P K. Methylene blue and serotonin toxicity: inhibition of monoamine oxidase A (MAO A) confirms a theoretical prediction. *Br J Pharmacol* 2007; 152: 946-51.

Ridha B H, Anderson V M, Bames J, et al. Volumetric MRI and cognitive measures in Alzheimer disease—Comparison of markers of progression. *J Neurol* 2008; 255: 567-74.

Salloway S. Sperling R. Fox N C, et al. Two phase 3 trials of bapineuzumab in mild-to-moderate Alzheimer's disease. *New Eng J Med* 2014; 370: 322-33.

Westfall P H. Multiple testing of general contrasts using logical constraints and correlations. *J Am Stat Assoc* 1997; 92: 299-306.

Wischik C M, Staff R T, Wischik D J, et al. Tau aggregation inhibitor therapy: an exploratory phase 2 study in mild or moderate Alzheimer's disease. *J Alzheimer's Dis* 2015; 44: 705-20.

The invention claimed is:

1. A method of therapeutic treatment of a disorder of protein aggregation which is mild cognitive impairment or Alzheimer's disease in a subject,
    which method comprises orally administering to said subject a methylthioninium (MT)-containing compound,
    wherein said administration provides a total daily dose of between 0.5 and 20 mg of MT to the subject per day, wherein the MT-containing compound is characterized by a purity of greater than 97% and wherein the MT-containing compound is methylthioninium chloride (MTC), or a hydrate thereof.

2. The method as claimed in claim 1 wherein said therapeutic treatment with the MT-containing compound comprises a total daily dose of MT from any of 0.5, 1, 1.5, 2, 2.5, 3, 3.5, 4 mg to 5, or 6 mg.

3. The method as claimed in claim 1 wherein said therapeutic treatment with the MT-containing compound comprises a total daily dose of MT of 0.5, 1, 1.5, 2, 2.5, 3, 3.5, 4, 5, or 6 mg.

4. The method as claimed in claim 1 wherein said therapeutic treatment comprises a total daily dose of the MT-containing compound administered as a split dose twice a day or three times a day.

5. The method as claimed in claim 1 wherein the MT-containing compound is MTC pentahydrate.

6. The method as claimed in claim 1 wherein the MT-containing compound is characterized by a purity of greater than 98%.

7. The method as claimed in claim 1, wherein the MT-containing compound is characterized by a purity of greater than 98% and one or more of the following:
    (i) less than 1% Azure B as impurity;
    (ii) less than 0.13% MVB (Methylene Violet Bernstein) as impurity;
    (iii) less than 0.15% Azure A as impurity;
    (iv) less than 0.15% Azure C as impurity; or
    (v) an elementals purity better than less than 100 µg/g Aluminium (Al); less than 1 µg/g Cadmium (Cd); less than 100 µg/g Chromium (Cr); less than 300 µg/g Copper (Cu); less than 10 µg/g Tin (Sn); less than 200 µg/g Iron (Fe); less than 10 µg/g Manganese (Mn); less than 1 µg/g Mercury (Hg); less than 10 µg/g Molybdenum (Mo); less than 10 µg/g Nickel (Ni); less than 10 µg/g Lead (Pb); and less than 100 µg/g Zinc (Zn).

8. The method as claimed in claim 1, wherein the MT-containing compound is characterized by a purity of greater than 98% and less than 1% Azure B as impurity.

9. The method as claimed in claim 1, wherein the MT-containing compound is characterized by a purity of greater than 98% and an elementals purity better than less than 100 µg/g Aluminium (Al); less than 1 µg/g Cadmium (Cd); less than 100 µg/g Chromium (Cr); less than 300 µg/g Copper (Cu); less than 10 µg/g Tin (Sn); less than 200 µg/g Iron (Fe); less than 10 µg/g Manganese (Mn); less than 1 µg/g Mercury (Hg); less than 10 µg/g Molybdenum (Mo); less than 10 µg/g Nickel (Ni); less than 10 µg/g Lead (Pb); and less than 100 µg/g Zinc (Zn).

10. The method as claimed in claim 1, wherein the MT-containing compound is characterized by:
    (i) at least 98% purity;
    (ii) less than 1% Azure B as impurity; and
    (iii) an elementals purity better than the European Pharmacopeia limits of less than 100 µg/g Aluminium (Al); less than 1 µg/g Cadmium (Cd); less than 100 µg/g Chromium (Cr); less than 300 µg/g Copper (Cu); less than 10 µg/g Tin (Sn); less than 200 µg/g Iron (Fe); less than 10 µg/g Manganese (Mn); less than 1 µg/g Mercury (Hg); less than 10 µg/g Molybdenum (Mo); less than 10 µg/g Nickel (Ni); less than 10 µg/g Lead (Pb); and less than 100 µg/g Zinc (Zn).

11. A method of prophylactic treatment of a disorder of protein aggregation which is mild cognitive impairment or Alzheimer's disease in a subject,
    which method comprises orally administering to said subject a methylthioninium (MT)-containing compound,
    wherein said administration provides a total daily dose of between 0.5 and 20 mg of MT to the subject per day, wherein the MT-containing compound is characterized by a purity of greater than 97% and wherein the MT-containing compound is methylthioinium chloride (MTC), or a hydrate thereof.

12. The method as claimed in claim 11 wherein the subject has not historically received treatment with an acetylcholinesterase inhibitor or an N-methyl-D-aspartate receptor antagonist.

13. The method as claimed in claim 11 wherein the disorder is mild cognitive impairment.

14. The method as claimed in claim 11 wherein the disorder is Alzheimer's disease.

15. The method as claimed in claim 11, wherein the MT-containing compound is administered in the form of a dosage unit,
    wherein the amount of MT in the dosage unit is 4 mg.

16. The method as claimed in claim 1 wherein the subject has not historically received treatment with an acetylcholinesterase inhibitor or an N-methyl-D-aspartate receptor antagonist.

17. The method as claimed in claim 1 wherein said therapeutic treatment comprises a total daily dose of the MT-containing compound administered as a single dose.

18. The method as claimed in claim 5 wherein said therapeutic treatment comprises a total daily dose of MTC pentahydrate of 5 to 10 mg/day.

19. The method as claimed in claim 1 wherein the disorder is mild cognitive impairment.

20. The method as claimed in claim 1 wherein the disorder is Alzheimer's disease.

21. The method as claimed in claim 1, wherein the MT-containing compound is administered in the form of a dosage unit,
    wherein the amount of MT in the dosage unit is 4 mg.

22. The method as claimed in claim 11 wherein said prophylactic treatment with the MT-containing compound comprises a total daily dose of MT from any of 0.5, 1, 1.5, 2, 2.5, 3, 3.5, 4 mg to 5, or 6 mg.

23. The method as claimed in claim 22 wherein said prophylactic treatment with the MT-containing compound comprises a total daily dose of MT of 0.5, 1, 1.5, 2, 2.5, 3, 3.5, 4, 5, or 6 mg.

24. The method as claimed in claim 11 wherein said prophylactic treatment comprises a total daily dose of the MT-containing compound administered as a split dose twice a day or three times a day.

25. The method as claimed in claim 11 wherein said prophylactic treatment comprises a total daily dose of the MT-containing compound administered as a single dose.

26. The method as claimed in claim 11 wherein the MT-containing compound is MTC pentahydrate.

27. The method as claimed in claim 26 wherein said prophylactic treatment comprises a total daily dose of MTC pentahydrate of 5 to 10 mg/day.

28. The method as claimed in claim 11 wherein the MT-containing compound is characterized by a purity of greater than 98%.

29. The method as claimed in claim 11, wherein the MT-containing compound is characterized by a purity of greater than 98% and one or more of the following:
   (i) less than 1% Azure B as impurity;
   (ii) less than 0.13% MVB (Methylene Violet Bernstein) as impurity;
   (iii) less than 0.15% Azure A as impurity;
   (iv) less than 0.15% Azure C as impurity; or
   (v) an elementals purity better than less than 100 µg/g Aluminium (Al); less than 1 µg/g Cadmium (Cd); less than 100 µg/g Chromium (Cr); less than 300 µg/g Copper (Cu); less than 10 µg/g Tin (Sn); less than 200 µg/g Iron (Fe); less than 10 µg/g Manganese (Mn); less than 1 µg/g Mercury (Hg); less than 10 µg/g Molybdenum (Mo); less than 10 µg/g Nickel (Ni); less than 10 µg/g Lead (Pb); and less than 100 µg/g Zinc (Zn).

30. The method as claimed in claim 11, wherein the MT-containing compound is characterized by a purity of greater than 98% and less than 1% Azure B as impurity.

31. The method as claimed in claim 11, wherein the MT-containing compound is characterized by a purity of greater than 98% and an elementals purity better than less than 100 µg/g Aluminium (Al); less than 1 µg/g Cadmium (Cd); less than 100 µg/g Chromium (Cr); less than 300 µg/g Copper (Cu); less than 10 µg/g Tin (Sn); less than 200 µg/g Iron (Fe); less than 10 µg/g Manganese (Mn); less than 1 µg/g Mercury (Hg); less than 10 µg/g Molybdenum (Mo); less than 10 µg/g Nickel (Ni); less than 10 µg/g Lead (Pb); and less than 100 µg/g Zinc (Zn).

32. The method as claimed in claim 11, wherein the MT-containing compound is characterized by:
   (i) at least 98% purity;
   (ii) less than 1% Azure B as impurity; and
   (iii) an elementals purity better than the European Pharmacopeia limits of less than 100 µg/g Aluminium (Al); less than 1 µg/g Cadmium (Cd); less than 100 µg/g Chromium (Cr); less than 300 µg/g Copper (Cu); less than 10 µg/g Tin (Sn); less than 200 µg/g Iron (Fe); less than 10 µg/g Manganese (Mn); less than 1 µg/g Mercury (Hg); less than 10 µg/g Molybdenum (Mo); less than 10 µg/g Nickel (Ni); less than 10 µg/g Lead (Pb); and less than 100 µg/g Zinc (Zn).

* * * * *